United States Patent
Luo et al.

(10) Patent No.: US 10,023,873 B2
(45) Date of Patent: Jul. 17, 2018

(54) METHODS AND COMPOSITIONS FOR TRANSGENIC PLANTS WITH ENHANCED COLD TOLERANCE, ABILITY TO FLOWER WITHOUT VERNALIZATION REQUIREMENT AND IMPACTED FERTILITY

(71) Applicant: Clemson University, Anderson, SC (US)

(72) Inventors: Hong Luo, Clemson, SC (US); Shauangrong Yuan, Pendleton, SC (US); Zhigang Li, Clemson, SC (US); Qian Hu, Clemson, SC (US)

(73) Assignee: Clemson University, Anderson, SC (US)

( * ) Notice: Subject to any disclaimer, the term of this patent is extended or adjusted under 35 U.S.C. 154(b) by 47 days.

(21) Appl. No.: 14/883,350

(22) Filed: Oct. 14, 2015

(65) Prior Publication Data

US 2016/0108411 A1    Apr. 21, 2016

Related U.S. Application Data

(60) Provisional application No. 62/063,779, filed on Oct. 14, 2014.

(51) Int. Cl.
| | |
|---|---|
| A01H 5/10 | (2018.01) |
| A01H 5/00 | (2018.01) |
| A01H 1/00 | (2006.01) |
| C12N 15/82 | (2006.01) |
| C12N 15/00 | (2006.01) |

(52) U.S. Cl.
CPC ....... *C12N 15/827* (2013.01); *C12N 15/8273* (2013.01); *C12N 15/8289* (2013.01)

(58) Field of Classification Search
None
See application file for complete search history.

(56) References Cited

U.S. PATENT DOCUMENTS

2006/0123505 A1* 6/2006 Kikuchi ............... C07K 14/415
                                                              800/278
2012/0278929 A1* 11/2012 Baum ................. C12N 15/8285
                                                              800/265

OTHER PUBLICATIONS

Ashraf et al. "Roles of glycine betaine and proline in improving plant abiotic stress resistance" *Environmental and Experimental Botany* 59(2):206-216 (2007) (Abstract only).
Chen et al. "Expression of a cloned sweet potato catalase SPCAT1 alleviates ethephon-mediated leaf senescence and $H_2O_2$ elevation" *Journal of Plant Physiology* 169(1):86-97 (2012) (Abstract only).
Kwon et al. "Molecular cloning, characterization and expression analysis of a catalase cDNA from hot pepper (*Capsicum annumm* L.)" *Plant Science* 160(5):961-969 (2001) (Abstract only).
Li et al. "Overexpression of tomato SpMPK3 gene in *Arabidopsis* enhances the osmotic tolerance" *Biochemical and Biophysical Research Communications* 443(2):357-362 (2014) (Abstract only).
Nuruzzaman et al. "Genome-wide analysis of NAC transcription factor family in rice" *Gene* 465(1-2):30-44 (2010) (Abstract only).
Pignocchi et al. "Apoplastic ascorbate metabolism and its role in the regulation of cell signalling" *Current Opinion in Plant Biology* 6(4):379-389 (2003) (Abstract only).
Véry et al. "Cation channels in the *Arabidopsis* plasma membrane" *Trends in Plant Science* 7(4):168-175 (2002) (Abstract only).
Wang et al. "Enhanced drought tolerance of transgenic rice plants expressing a pea manganese superoxide dismutase" *Journal of Plant Physiology* 162:465-472 (2005).
Yuan et al. "Constitutive Expression of Rice MicroRNA528 Alters Plant Development and Enhances Tolerance to Salinity Stress and Nitrogen Starvation in Creeping Bentgrass" *Plant Physiology* 169:576-593 (2015).
Abràmoff et al. "Image Processing with ImageJ" *Biophotonics International* 11:36-43 (2004).
Ali et al. "Effect of salinity on chlorophyll concentration, leaf area, yield and yield components of rice genotypes grown under saline environment" *International Journal of Environmental Science & Technology* 1(3):221-225 (2004).
An et al. "Sequencing-Based Approaches Reveal Low Ambient Temperature-Responsive and Tissue-Specific MicroRNAs in *Phalaenopsis* Orchid" *PLoS One* 6(5):e18937 (2011).
Bates et al. "Rapid determination of free proline for water-stress studies" *Plant and Soil* 39:205-207 (1973).
Baxter et al. "A Coastal Cline in Sodium Accumulation in *Arabidopsis thaliana* Is Driven by Natural Variation of the Sodium Transporter AtHKT1;1" *PLoS Genetics* 6(11):e1001193 (2010).
Becker et al. "Differences in gene expression between natural and artificially induced leaf senescence" *Planta* 189:74-79 (1993).
Bhardwaj et al. "A Genome-Wide Perspective of miRNAome in Response to High Temperature, Salinity and Drought Stresses in *Brassica juncea* (Czern) L." *PLoS One* 9(3):e92456 (2014).
Buchanan-Wollaston et al. "Comparative transcriptome analysis reveals significant differences in gene expression and signalling pathways between developmental and dark/starvation-induced senescence in *Arabidopsis*" *The Plant Journal* 42:567-585 (2005).
Chapin et al. "Growth response of barley and tomato to nitrogen stress and its control by abscisic acid, water relations and photosynthesis" *Planta* 173:352-366 (1988).
Crété et al. "Nitrite reductase expression is regulated at the post-transcriptional level by the nitrogen source in *Nicotiana plumbaginifolia* and *Arabidopsis thaliana*" *The Plant Journal* 11(4):625-634 (1997).
Cui et al. "The miR156-SPL9-DFR pathway coordinates the relationship between development and abiotic stress tolerance in plants" *The Plant Journal* 80:1108-1117 (2014).

(Continued)

*Primary Examiner* — Phoenix Bui
(74) *Attorney, Agent, or Firm* — Myers Bigel, P.A.

(57) ABSTRACT

The present invention provides transgenic plants having increased tolerance to cold and altered flowering characteristics. Also provided are methods and compositions for producing said transgenic plants.

8 Claims, 30 Drawing Sheets

(56) References Cited

OTHER PUBLICATIONS

Dai et al. "psRNATarget: a plant small RNA target analysis server" *Nucleic Acids Research* 39:W155-W159 (2011).
Debernardi et al. "Functional Specialization of the Plant miR396 Regulatory Network through Distinct MicroRNA-Target Interactions" *PLoS Genetics* 8(1):e1002419 (2012).
Ding et al. "Differential expression of miRNAs in response to salt stress in maize roots" *Annals of Botany* 103:29-38 (2009).
Du et al. "Comprehensive Functional Analysis of the Catalase Gene Family in *Arabidopsis thaliana*" *Journal of Integrative Plant Biology* 50(10):1318-1326 (2008).
Fei et al. "Overexpression of a soybean cytosolic glutamine synthetase gene linked to organ-specific promoters in pea plants grown in different concentrations of nitrate" *Planta* 216:467-474 (2003).
Ferrario-Mery et al. "Overexpression of Nitrate Reductase in Tobacco Delays Drought-Induced Decreases in Nitrate Reductase Activity and mRNA" *Plant Physiology* 117:293-302 (1998).
Ferreira et al. "microRNAs Associated with Drought Response in the Bioenergy Crop Sugarcane (*Saccharum* spp.)" *PLoS One* 7(10):e46703 (2012).
Fraisier et al. "Constitutive expression of a putative high-affinity nitrate transporter in *Nicotiana plumbaginifolia*: evidence for post-transcriptional regulation by a reduced nitrogen source" *The Plant Journal* 23(4):489-496 (2000).
Gambale et al. "Properties of Shaker-type Potassium Channels in Higher Plants" *The Journal of Membrane Biology* 210:1-19 (2006).
Gao et al. "Over-expression of osa-MIR396c decreases salt and alkali stress tolerance" *Planta* 231:991-1001 (2010).
Gen Bank Accession No. AK062523 "Oryza sativa Japonica Group cDNA clone:001-104-D07, full insert sequence" *NCBI* (2 pages) (Dec. 4, 2008).
Giannopolitis et al. "Superoxide Dismutases: I. Occurrence in Higher Plants" *Plant Physiology* 59:309-314 (1977).
Golldack et al. "Plant tolerance to drought and salinity: stress regulating transcription factors and their functional significance in the cellular transcriptional network" *Plant Cell Reports* 30:1383-1391 (2011).
Gupta et al. "Differential regulation of microRNAs in response to osmatic, salt and cold stresses in wheat" *Molecular Biology Reports* 41:4623-4629 (2014).
Hackenberg et al. "A Transgenic Transcription Factor (TaDREB3) in Barley Affects the Expression of MicroRNAs and Other Small Non-Coding RNAs" *PLoS ONE* 7(8):e42030 (2012).
Haynes, R. J. "A comparison of two modified Kjeldahl digestion techniques for multi-element plant analysis with conventional wet and dry ashing methods" *Communications in Soil Science and Plant Analysis* 11(5):459-467 (1980).
Huijser et al. "The control of developmental phase transitions in plants" *Development* 138:4117-4129 (2011).
Kandlbinder et al. "The antioxidant status of photosynthesizing leaves under nutrient deficiency: redox regulation, gene expression and antioxidant activity in *Arabidopsis thaliana*" *Physiologia Plantarum* 120:63-73 (2004).
Kikuchi et al. "Collection, Mapping, and Annotation of Over 28,000 cDNA Clones from *japonica* Rice" *Science* 301(5631):376-379 (2003).
Kim et al. "Cold Shock Domain Protein 3 is involved in salt and drought stress tolerance in *Arabidopsis*" *FEBS Open Bio* 3:438-442 (2013).
Koussevitzky et al. "Ascorbate Peroxidase 1 Plays a Key Role in the Response of *Arabidopsis thaliana* to Stress Combination" *The Journal of Biological Chemistry* 283(49):34197-34203 (2008).
Koyama et al. "TCP Transcription Factors Regulate the Activities of Asymmetric Leaves1 and miR164, as Well as the Auxin Response, during Differentiation of Leaves in *Arabidopsis*" *The Plant Cell* 22:3574-3588 (2010).
Kozomara et al. "miRBase: annotating high confidence microRNAs using deep sequencing data" *Nucleic Acids Research* 42:D68-D73 (2014).

Lebaudy et al. "$K^+$ channel activity in plants: Genes, regulations and functions" *FEBS Letters* 581:2357-2366 (2007).
Leshem et al. "Suppression of *Arabidopsis* vesicle-SNARE expression inhibited fusion of $H_2O_2$-containing vesicles with tonoplast and increased salt tolerance" *Proceedings of the National Academy of Sciences USA* 103:18008-18013 (2006).
Li et al. "Heterologous expression of *Arabidopsis* $H^+$-pyrophosphatase enhances salt tolerance in transgenic creeping bentgrass (*Agrostis stolonifera* L.)" *Plant, Cell and Environment* 33:272-289 (2010).
Li et al. "Spatial-temporal analysis of zinc homeostasis reveals the response mechanisms to acute zinc deficiency in *Sorghum bicolor*" *New Phytologist* 200:1102-1115 (2013).
Liang et al. "Identification of Nitrogen Starvation-Responsive MicroRNAs in *Arabidopsis thaliana*" *PLoS ONE* 7(11):e48951 (2012).
Limami et al. "Does root glutamine synthetase control plant biomass production in *Lotus japonicus* L.?" *Planta* 209:495-502 (1999).
Liu et al. "Loss of Function of OsDCL1 Affects MicroRNA Accumulation and Causes Developmental Defects in Rice" *Plant Physiology* 139:296-305 (2005).
Livak et al. "Analysis of Relative Gene Expression Data Using Real-Time Quantitative PCR and the $2^{\Delta\Delta C_T}$ Method" *Methods* 25:402-408 (2001).
Lu et al. "Overexpression of *Arabidopsis* Molybdenum Cofactor Sulfurase Gene Confers Drought Tolerance in Maize (*Zea mays* L.)" *PLoS ONE* 8(1):e52126 (2013).
Luo et al. "Mitochondrial DNA polymorphism and phylogenetic relationships in *Hevea brasiliensis*" *Molecular Breeding* 1:51-63 (1995).
Luo et al. "Phylogenetic relationships within *Hevea brasiliensis* as deduced from a polymorphic mitochondrial DNA region" *Theoretical and Applied Genetics* 91:876-884 (1995).
Luo et al. "*Agrobacterium tumefaciens*-mediated creeping bentgrass (*Agrostis stolonifera* L.) transformation using phosphinothricin selection results in a high frequency of single-copy transgene integration" *Plant Cell Reports* 22:645-652 (2004).
Maathuis et al. "$K^+$Nutrition and $Na^+$Toxicity: The Basis of Cellular $K^{+/Na+}$ Ratios" *Annals of Botany* 84:123-133 (1999).
Marshall et al. "Rationally Tuning the Reduction Potential of a Single Cupredoxin Beyond the Natural Range" *Nature* 462(7269):113-116 (2009).
Masclaux-Daubresse et al. "Nitrogen uptake, assimilation and remobilization in plants: challenges for sustainable and productive agriculture" *Annals of Botany* 105:1141-1157 (2010).
Mäser et al. "Phylogenetic Relationships within Cation Transporter Families of *Arabidopsis*" *Plant Physiology* 126:1646-1667 (2001).
Mhamdi et al. "Catalase function in plants: a focus on *Arabidopsis* mutants as stress-mimic models" *Journal of Experimental Botany* 61(15):4197-4220 (2010).
Mian et al. "Over-expression of an Na+- and K+-permeable HKT transporter in barley improves salt tolerance" *The Plant Journal* 68:468-479 (2011).
Munns, R. "Physiological processes limiting plant growth in saline soils: some dogmas and hypotheses" *Plant, Cell and Environment* 16:15-24 (1993).
Munns, R. "Comparative physiology of salt and water stress" *Plant, Cell and Environment* 25:239-250 (2002).
Nischal et al. "Identification and Comparative Analysis of MicroRNAs Associated with Low-N Tolerance in Rice Genotypes" *PLoS ONE* 7(12):e50261 (2012).
Pandey et al. "A Comprehensive Genome-Wide Study on Tissue-Specific and Abiotic Stress-Specific miRNAs in *Triticum aestivum*" *PLoS ONE* 9(4):e95800 (2014).
Pathak et al. "Molecular physiology of plant nitrogen use efficiency and biotechnological options for its enhancement" *Current Science* 94(11):1394-1403 (2008).
Pignocchi et al. "The Function of Ascorbate Oxidase in Tobacco" *Plant Physiology* 132:1631-1641 (2003).
Rizhsky et al. "When Defense Pathways Collide. The Response of *Arabidopsis* to a Combination of Drought and Heat Stress" *Plant Physiology* 134:1683-1696 (2004).

(56) References Cited

OTHER PUBLICATIONS

Rodriguez et al. "Control of cell proliferation in *Arabidopsis thaliana* by microRNA miR396" *Development* 137:103-112 (2010).
Sanmartin et al. "Over-expression of ascorbate oxidase in the apoplast of transgenic tobacco results in altered ascorbate and glutathione redox states and increased sensitivity to ozone" *Planta* 216:918-928 (2003).
Satoh et al. "Gene Organization in Rice Revealed by Full-Length cDNA Mapping and Gene Expression Analysis through Microarray" *PLoS ONE* 2(11):e1235 (2007).
Sharma et al. "Differential expression of microRNAs by arsenate and arsenite stress in natural accessions of rice" *Metallomics* 7:174-187 (2015).
Shinozaki et al. "Gene networks involved in drought stress response and tolerance" *Journal of Experimental Botany* 58(2):221-227 (2007).
Solomon et al. "Electronic Structures of Metal Sites in Proteins and Models: Contributions to Function in Blue Copper Proteins" *Chemical Reviews* 104:419-458 (2004).
Takahashi et al. "Nitrite Reductase Gene Enrichment Improves Assimilation of $NO_2$ in *Arabidopsis*" *Plant Physiology* 126:731-741 (2001).
Thiebaut et al. "Genome-wide identification of microRNA and siRNA responsive to endophytic beneficial diazotrophic bacteria in maize" *BMC Genomics* 15:766 (2014).
Turan et al. "Salinity tolerance in plants: Breeding and genetic engineering" *Australian Journal of Crop Science* 6(9):1337-1348 (2012).
Varkonyi-Gasic et al. "Protocol: a highly sensitive RT-PCR method for detection and quantification of microRNAs" *Plant Methods* 3:1-12 (2007).
Véry et al. "Molecular Mechanisms and Regulation of $K^+$ Transport in Higher Plants" *Annual Review of Plant Biology* 54:575-603 (2003).
Wu et al. "Rice MicroRNA Effector Complexes and Targets" *The Plant Cell* 21:3421-3435 (2009).
Wu et al. "The sequential action of miR156 and miR172 regulates developmental timing in *Arabidopsis*" *Cell* 138(4):750-759 (2009).
Xiao et al. "Functional analysis of the rice AP3 homologue OsMADS16 by RNA interference" *Plant Molecular Biology* 52:957-966 (2003).
Xie et al. "Deep sequencing reveals important roles of microRNAs in response to drought and salinity stress in cotton" *Journal of Experimental Botany* 66(3):789-804 (2015).
Xu et al. "Genome-Wide Identification of MicroRNAs in Response to Low Nitrate Availability in Maize Leaves and Roots" *PLoS ONE* 6(11):e28009 (2011).
Yan et al. "Comparative expression profiling of miRNAs between the cytoplasmic male sterile line MeixiangA and its maintainer line MeixiangB during rice anther development" *Planta* 241:109-123 (2015).
Yang et al. "The Role of a Potassium Transporter OsHAK5 in Potassium Acquisition and Transport from Roots to Shoots in Rice at Low Potassium Supply Levels" *Plant Physiology* 166:945-959 (2014).
Yeo, Anthony "Molecular biology of salt tolerance in the context of whole-plant physiology" *Journal of Experimental Botany* 49(323):915-929 (1998).
Yuan et al. "Heterologous expression of a rice miR395 gene in *Nicotiana tabacum* impairs sulfate homeostasis" *Scientific Reports* 6(28791):1-14 (2016).
Zanca et al. "Identification and expression analysis of microRNAs and targets in the biofuel crop sugarcane" *BMC Plant Biology* 10(260):1-13 (2010).
Zhang et al. "Submergence-responsive MicroRNAs are Potentially Involved in the Regulation of Morphological and Metabolic Adaptations in Maize Root Cells" *Annals of Botany* 102:509-519 (2008).
Zhou et al. "Constitutive Expression of a miR319 Gene Alters Plant Development and Enhances Salt and Drought Tolerance in Transgenic Creeping Bentgrass" *Plant Physiology* 161:1375-1391 (2013).
Zhou et al. "MicroRNA-mediated gene regulation: potential applications for plant genetic engineering" *Plant Molecular Biology* 83:59-75 (2013).
Zhou et al. "Role of microRNA319 in creeping bentgrass salinity and drought stress response" *Plant Signaling & Behavior* 9:e28700 (2014).
Zhu et al. "Salt and Drought Stress Signal Transduction in Plants" *Annual Review of Plant Biology* 53:247-273 (2002).

* cited by examiner

METHODS AND COMPOSITIONS FOR TRANSGENIC PLANTS WITH ENHANCED COLD TOLERANCE, ABILITY TO FLOWER WITHOUT VERNALIZATION REQUIREMENT AND IMPACTED FERTILITY

STATEMENT OF PRIORITY

This application claims the benefit, under 35 U.S.C. § 119(e), of U.S. Provisional Application Ser. No. 62/063,779, filed Oct. 14, 2014, the entire contents of which are incorporated by reference herein.

STATEMENT OF GOVERNMENT SUPPORT

This invention was made with government support under grant #2010-33522-21656 awarded by the United States Department of Agriculture National Institute of Food and Agriculture. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 9662-62_ST25.txt, 22,677 bytes in size, generated on Apr. 12, 2016 and filed via EFS-Web, is provided in lieu of a paper copy. This Sequence Listing is hereby incorporated by reference into the specification for its disclosures.

FIELD OF INVENTION

The present invention relates to methods and compositions for producing transgenic plants with enhanced resistance to cold and other environmental stresses and the ability to flower by bypassing the vernalization requirement, as well as impaired pollen fertility.

BACKGROUND

With the significant advances made in the area of genomics, genetic regulators related to plant stress tolerance have been identified, which may have the potential to be utilized in crop improvement through genetic engineering. One example of such a genetic regulator is microRNA (miRNA). MicroRNAs are a class of noncoding small RNAs which originate from pri-miRNA transcripts that are encoded by miRNA genes. The pri-miRNA transcripts are processed into smaller 19-24 nucleotide RNAs, which can regulate gene expression, for example, through silencing reactions by translational inhibition or cleavage.

MiR396 is an evolutionarily conserved miRNA family which is involved in both flowering development and abiotic stress responses. It contains two family members (miR396a-b) in *Arabidopsis*, and six family members (miR396a-f) in rice. Its targets are genes encoding for growth-regulating factor (GRF), which are transcription factors involved in plant growth and development.

Flowering is a crucial phase to determine the plant reproduction success. Optimal flowering time provides favorable environmental conditions for seed development. Many crop species require prolonged exposure to cold (e.g., winter cold) or vernalization to promote their vegetative-to-reproductive stage transition. Vernalization largely limits crop growth region as well as flowering time due to varied winter temperature from place to place and from year to year. In this context, it is highly valuable to develop new strategies to control flowering, including breaking the vernalization requirement.

The present invention overcomes previous shortcomings in the art by providing methods and compositions for transgenic plants with increased cold tolerance and the ability to flower by bypassing vernalization as well as impaired pollen fertility.

SUMMARY OF THE INVENTION

In one aspect, the present invention provides a transgenic plant having increased cold tolerance, altered flowering characteristics (i.e., flowering that bypasses vernalization), deformed pollen (male sterility) and altered development, comprising a recombinant nucleic acid molecule, said recombinant nucleic acid molecule comprising a nucleotide sequence encoding miR396c operatively associated with a promoter, wherein overexpression of the nucleotide sequence encoding miR396c confers increased cold tolerance, flowering bypassing the vernalization requirement, defective pollen development (male sterility) and altered plant development as compared with a plant that does not comprise said recombinant nucleic acid molecule comprising the nucleotide sequence encoding miR396c operatively associated with a promoter.

In one aspect, the present invention provides a method of producing a transgenic plant having increased cold tolerance and altered flowering characteristics (i.e., flowering bypassing vernalization requirement), defective pollen and altered plant development, comprising: a) transforming a plant cell with a recombinant nucleic acid molecule, said recombinant nucleic acid molecule comprising a nucleotide sequence encoding miR396c or other members of the miRNA 396 gene family operatively associated with a promoter; and b) regenerating a transgenic plant from the transformed plant cell, thereby producing a transgenic plant having increased cold tolerance and altered flowering characteristics (i.e., flowering bypassing vernalization requirement), defective pollen and altered plant development as compared with a plant that is not transformed with said recombinant nucleic acid molecule.

In a further aspect, the present invention provides a nucleic acid construct comprising, in the following order from 5' to 3': a) a first promoter; b) a nucleotide sequence encoding miR396c; c) a first termination sequence; d) a second promoter; e) a nucleotide sequence encoding a selectable marker operably associated with the promoter of (d); and f) a second termination sequence.

In an additional aspect, the present invention provides a method of producing a transgenic plant having increased cold tolerance and altered flowering characteristics (i.e., flowering bypassing vernalization requirement), defective pollen and altered plant development, comprising: a) transforming a cell of a plant with the nucleic acid construct of this invention; and b) regenerating the transgenic plant from the transformed plant cell, wherein the plant has increased cold tolerance and altered flowering characteristics (i.e., flowering bypassing vernalization requirement), defective (e.g., nonfunctional) pollen and altered plant development as compared with a plant that is not transformed with said nucleic acid construct.

These and other aspects of the invention are set forth in more detail in the description of the invention below.

VRN2, and (panel c) VRN3 from creeping bentgrass, Brachypodium, wheat, barley, rice and *Arabidopsis* were built with the neighbor joining method. Bootstrap values were derived from 1000 replications. Alignment of (panel d) type II subfamily of MADS domain and K-box (SEQ ID NOS: 2-7), (panel e) CCT domain (SEQ ID NOS:8-14), and (panel f) PEBP (phosphatidylethanolamine) domain (SEQ ID NOS: 15-20) among different plant species, including creeping bentgrass, *Brachypodium*, wheat, barley, rice and *Arabidopsis*. Species abbreviations: As=*Agrostis stolonifera*, Bd=*Brachypodium distachyon*, Ta=*Triticum aestivum*, Tm=*Triticum monococcum*, Hv=*Hordeum vulgare*, Os=*Oryza sativa*, and At=*Arabidopsis thaliana*. Similarities of conserved domains between creeping bentgrass and each of the orthologs are listed at the end of the alignment.

Figure 15:
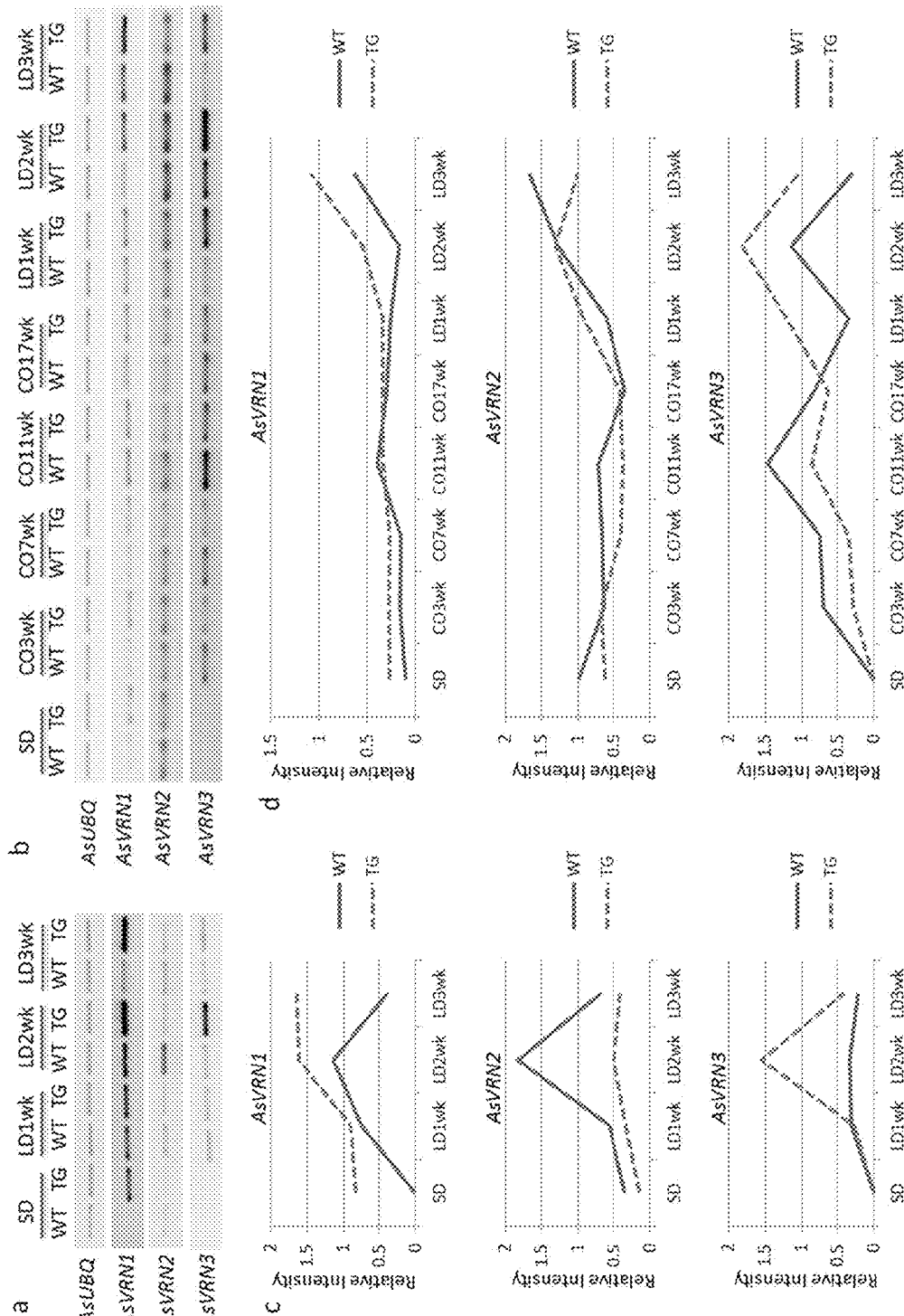

FIG. 15. Expression profiles of AsVRN1, AsVRN2, and AsVRN3 in SD-LD and SD-cold-LD conditions. (panel a) Semi-quantitative RT-PCR analysis of AsVRN1, AsVRN2, and AsVRN3 gene expression in WT and TG plants under SD and LD conditions without vernalization. (panel b) Semi-quantitative RT-PCR analysis of AsVRN1, AsVRN2, and AsVRN3 gene expression in WT and TG plants under SD, cold and LD conditions. AsUBQ was used as an endogenous control. Analyses of band intensity on electrophoresis gel are presented as relative ratio of AsVRN1, AsVRN2, and AsVRN3 to AsUBQ under SD and LD conditions (panel c) without vernalization, and (panel d) with prolonged cold treatment. The band intensity was quantified using ImageJ.

Figure 16:
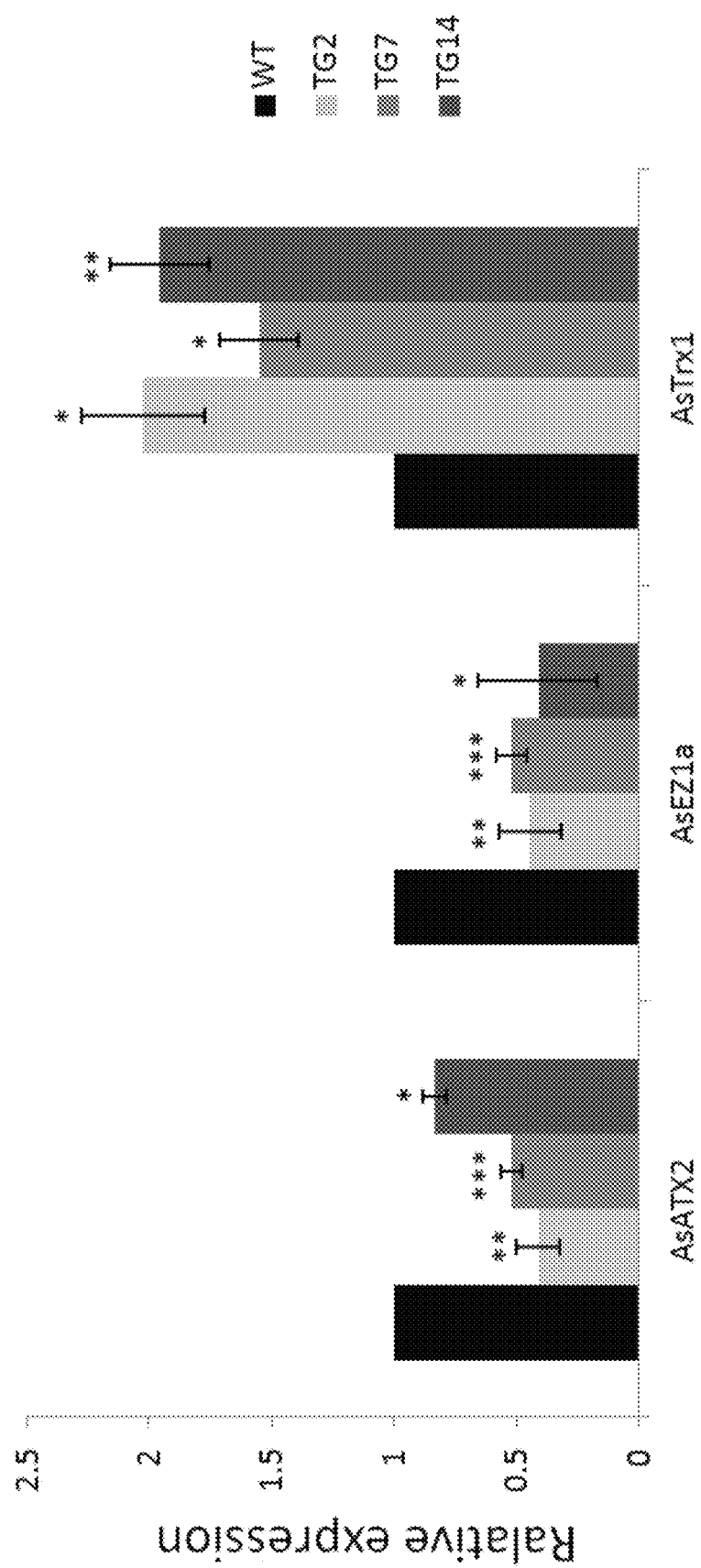

FIG. 16. Expression levels of methyltransferases AsATX2, AsEZ1a, and AsTrx1 in WT and TG plants under SD conditions. Real-time RT-PCR analysis of AsATX2, AsEZ1a, and AsTrx1 expression in WT and three transgenic plants under SD conditions. AsUBQ was used as an endogenous control. Data are presented as means of three technical replicates, and error bars represent ±SE.

Figure 17:
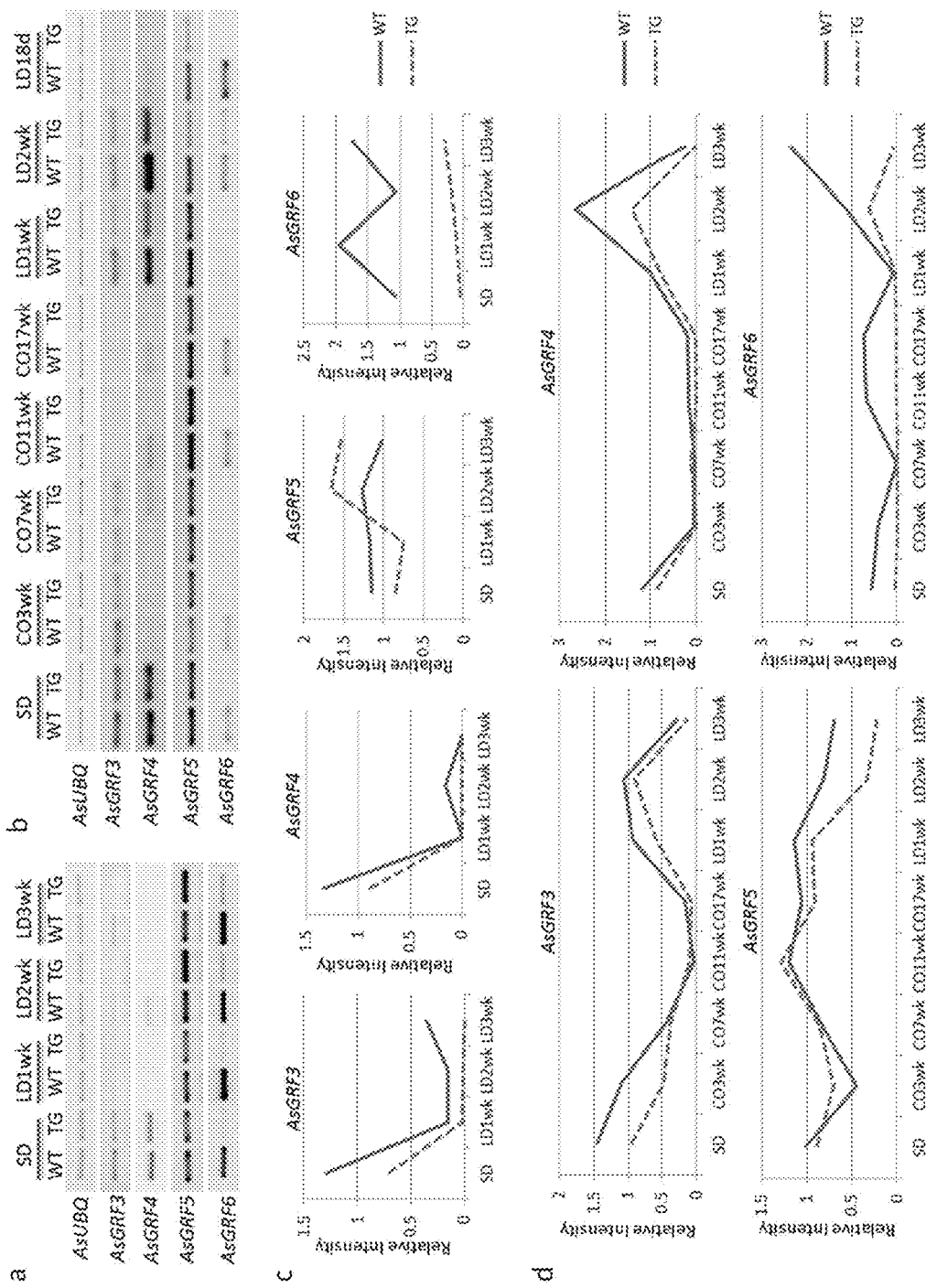

FIG. 17. Expression profiles of miR396c potential targets AsGRF3, AsGRF4, AsGRF5, and AsGRF6 in SD-LD and SD-cold-LD conditions. (panel a) Semi-quantitative RT-PCR analysis of AsGRF3, AsGRF4, AsGRF5, and AsGRF6 gene expression profiles in WT and TG plants under SD-LD and (panel b) SD-cold-LD conditions. (panel c) Analyses of band intensity on electrophoresis gel are presented as relative ratio of AsGRF3, AsGRF4, AsGRF5, and AsGRF6 to AsUBQ under SD-LD conditions and (panel d) SD-cold-LD conditions. The band intensity was quantified using ImageJ.

Figure 18:
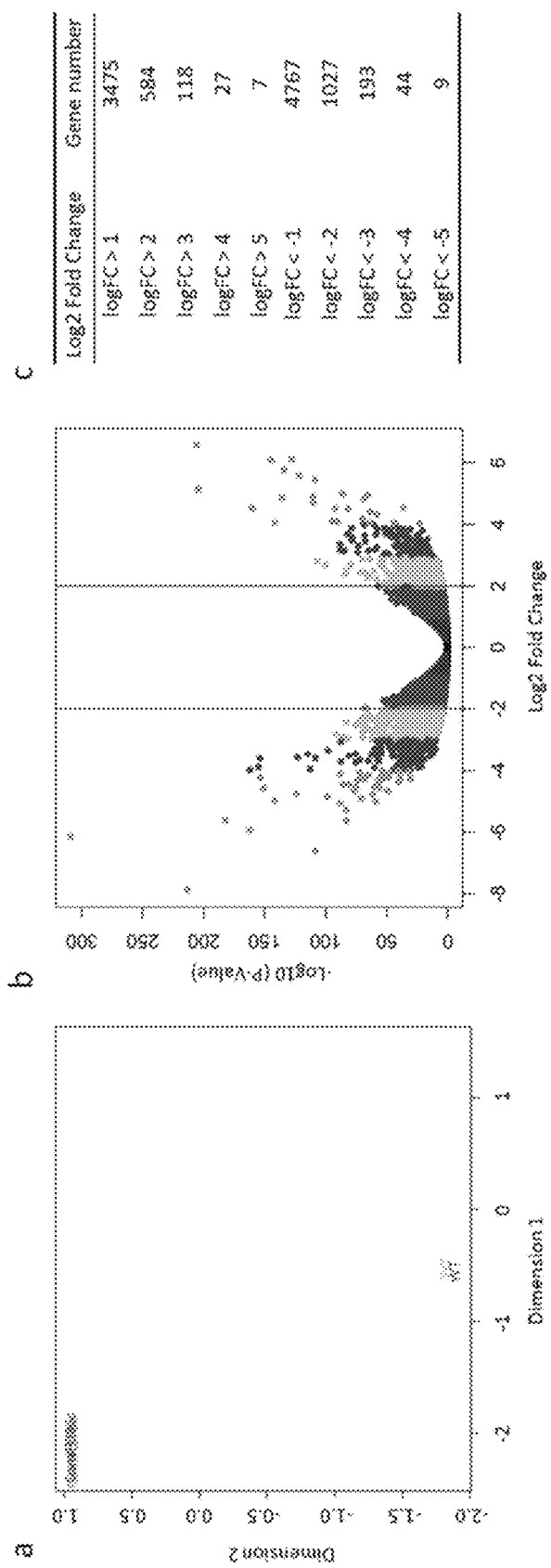

FIG. 18. Comparison of RNA-seq data sets between WT and TG plants during LD 3-week without vernalization. (panel a) MDS plot of WT and Os-miR396c TG RNA-seq libraries with two biological replicates. (panel b) Volcano plot shows $\log_2$ FC of TG vs. WT data sets during 3-week LD induction without vernalization. (c) A table shows $\log_2$ FC values and corresponding gene number.

Figure 19:
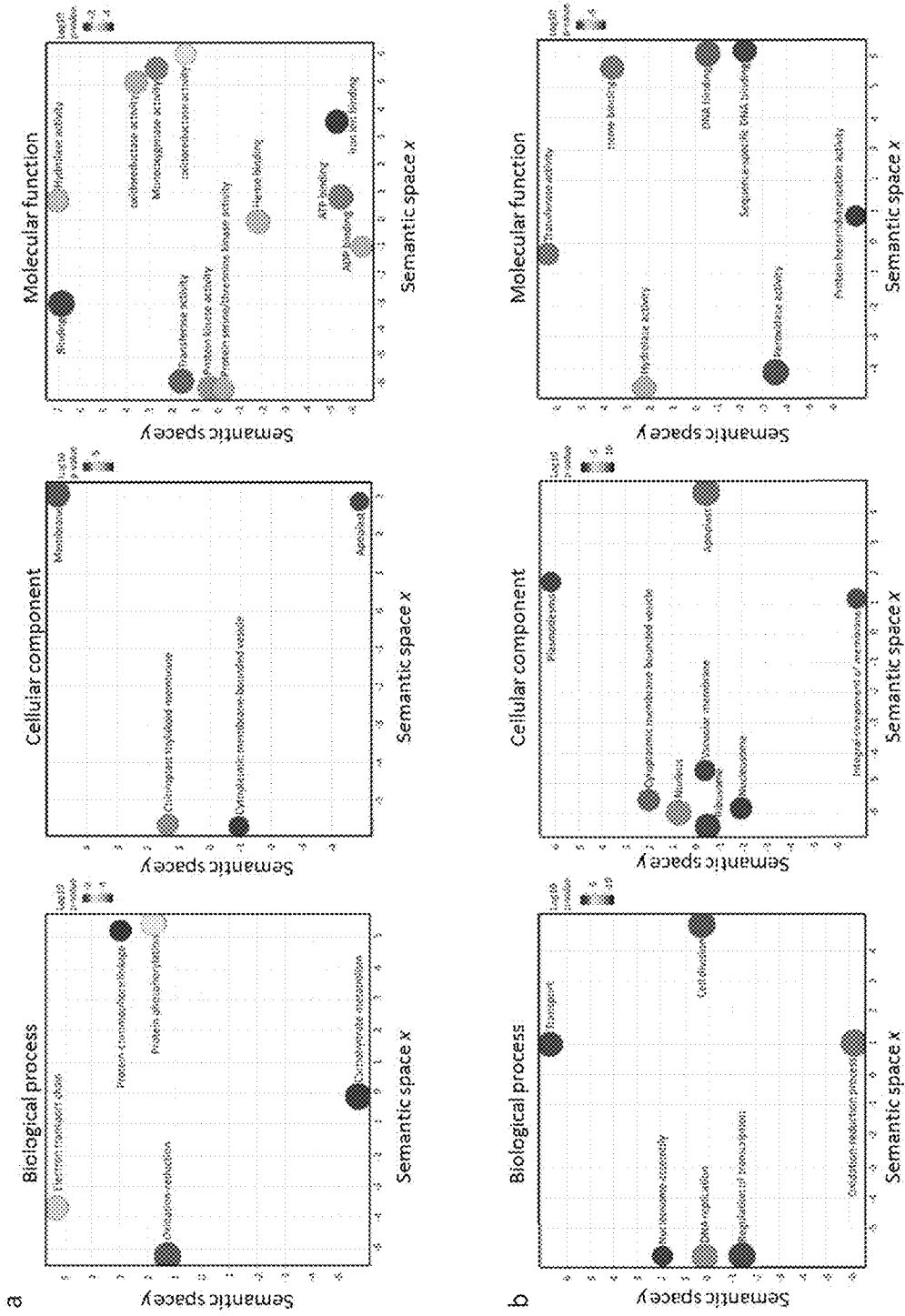

FIG. 19. GO enrichment analysis. Significantly enriched GO terms for (panel a) up-regulated ($\log_2$ FC>2) and (panel b) down-regulated ($\log_2$ FC<−2) TG vs. WT data sets were listed in three GO categories, including biological process, cellular component, and molecular function. Each bubble represents a GO term. The closer the bubbles rest, the more related the GO terms are. The bubble color represents the significance of the enrichment. Bubbles with more general GO terms are larger.

Figure 20:
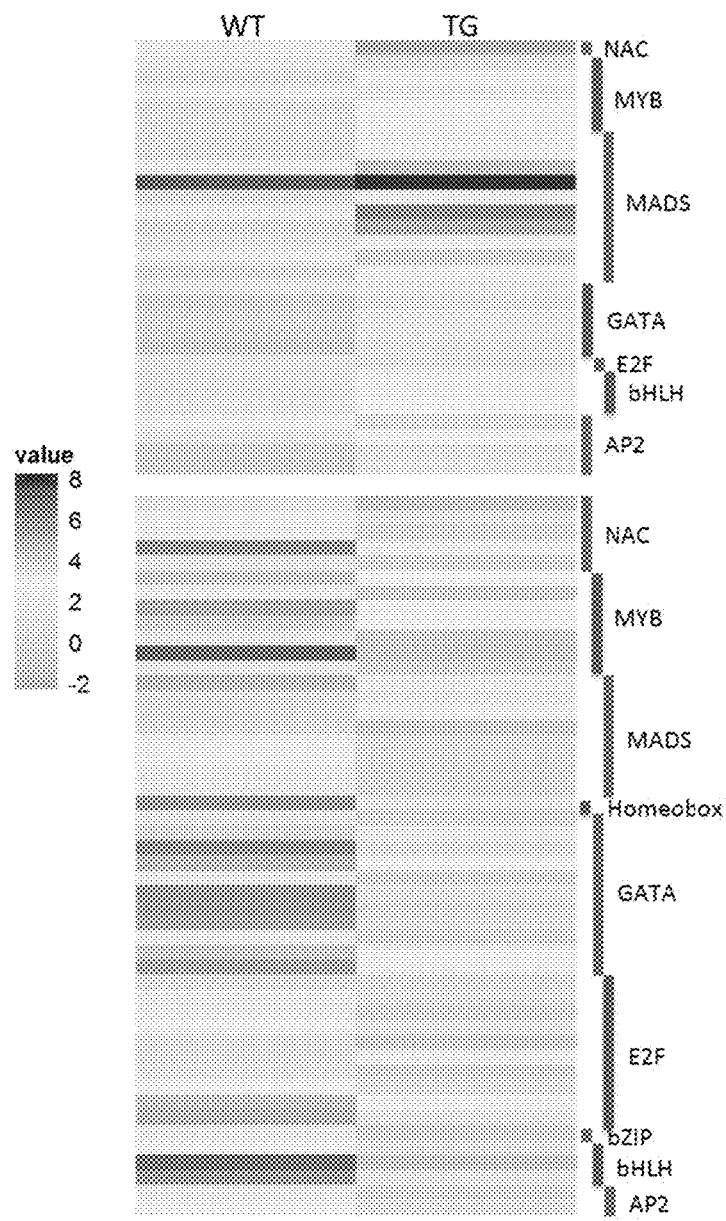

FIG. 20. Differential expression of transcription factor genes during 3-week LD induction. Various transcription factor families with differential expression ($\log_2$ FC>1 and $\log_2$ FC<−1 in upper and lower panel, respectively) is shown in the heatmap. The color scale represents the $\log_e$-transformation of the read count value.

Figure 21:
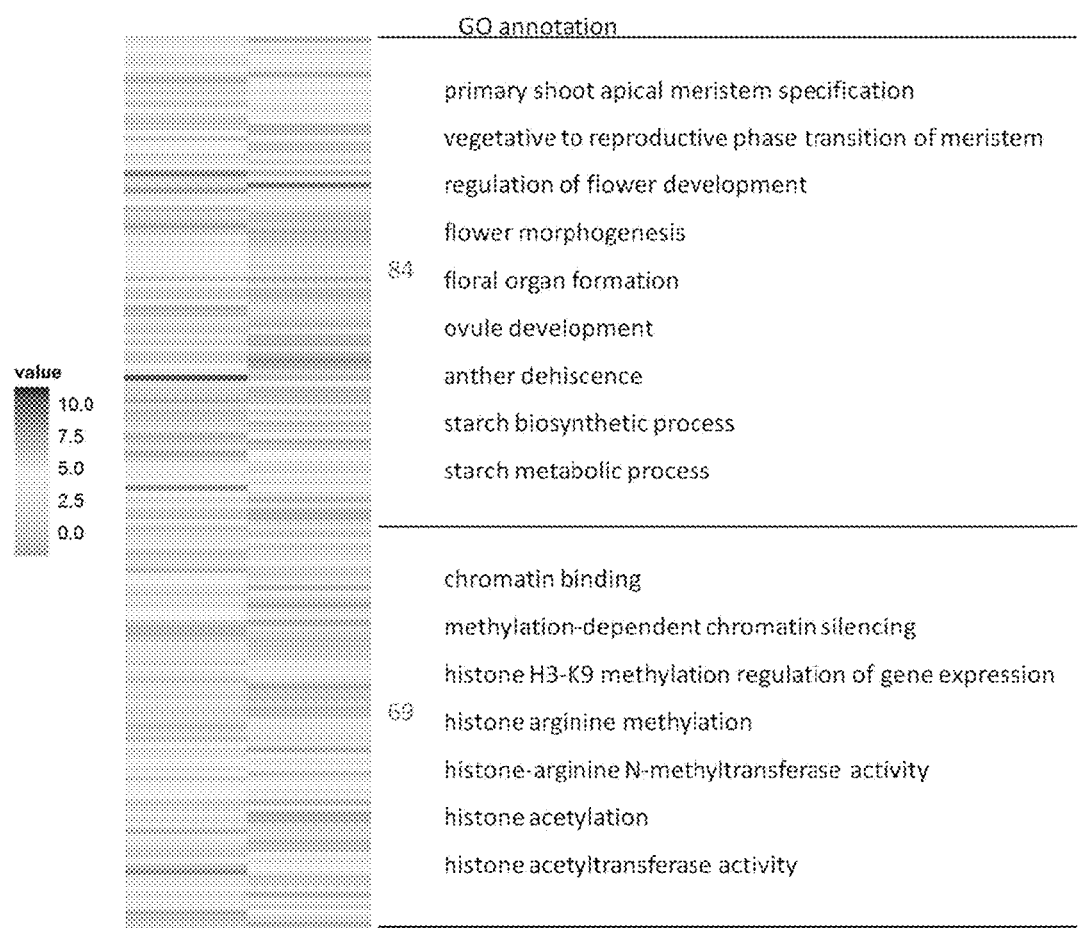

FIG. 21. Differential expression of flower development and chromatin modification related genes. Significantly enriched GO terms ($\log_2$ FC>1 or $\log_2$ FC<−1, FDR<0.05), which related to flower development and chromatin modification, for TG vs. WT data sets were listed. The corresponding DEGs of each enriched GO term were selected to generate the heatmap. The color gradient shows the $\log_2$-transformation of the read count value.

Figure 22:
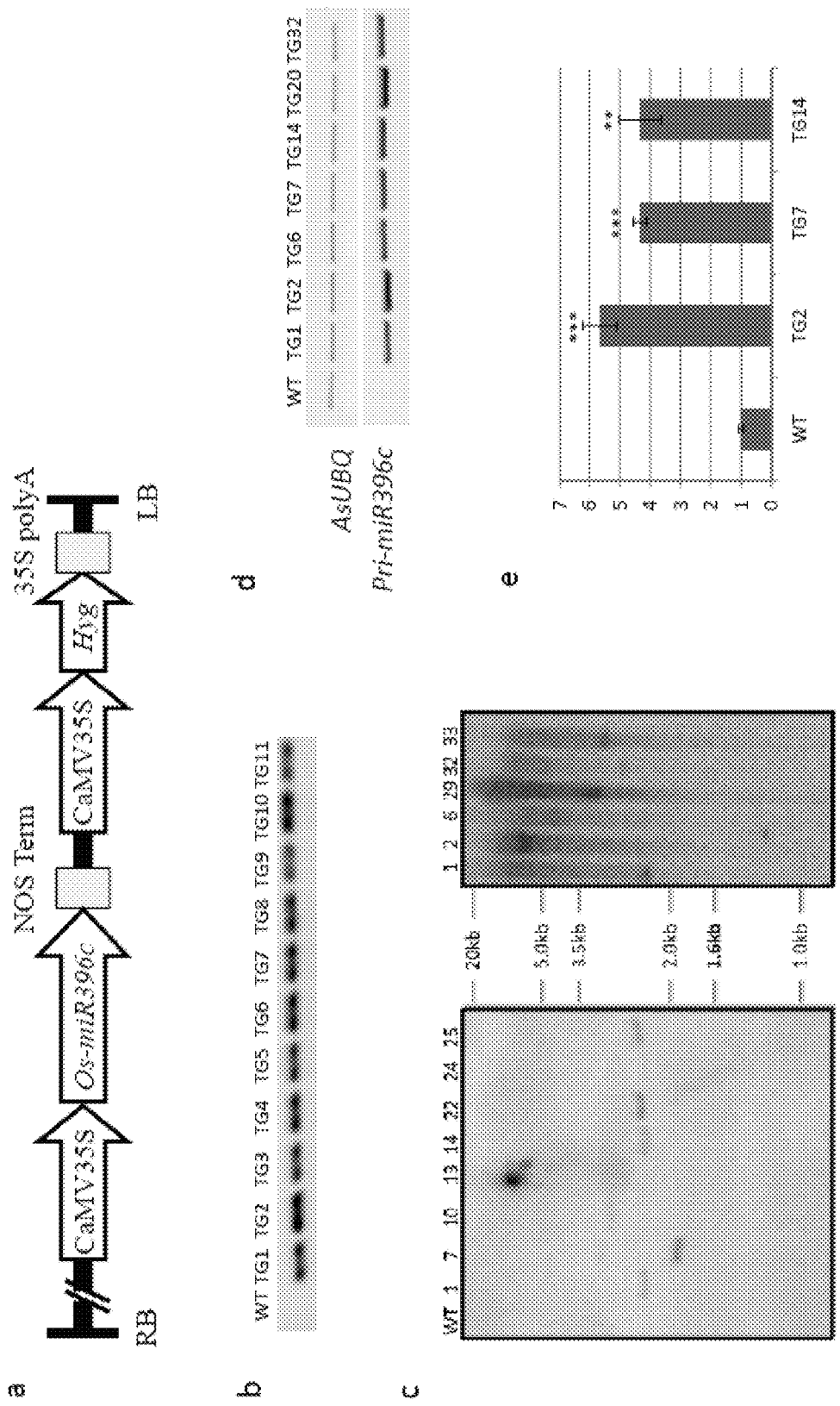

FIG. 22. Generation and molecular analysis of transgenic creeping bentgrass overexpressing Osa-miR396c. (panel a) The schematic diagram of Osa-miR396c gene overexpression construct, p35S-Osa-miR396c/p35S-Hyg. Osa-miR396c gene is under the control of Cauliflower Mosaic Virus (CaMV) 35S promoter and linked to the hygromycin resistance gene, Hyg, driven by CaMV 35S promoter. RB: right border; LB: left border. (panel b) Examples of PCR analysis to amplify Hyg gene using genomic DNA of WT and TG creeping bentgrass to determine the integration of Osa-miR396c gene in the host genome. (panel c) Southern blot analysis to detect different miR396c-expressing transgenic lines. (panel d) Semi-quantitative RT-PCR analysis to compare the expression levels of primary Osa-miR396c in WT and TG plants. (panel e) Stem-loop RT-qPCR analysis to detect the expression of mature Osa-miR396c in TG and WT plants. The relative changes in gene expression were calculated based on 2-ΔΔCT method. AsUBQ was used as an endogenous control. Data are presented as means of three technical replicates, and error bars represent ±SE. Asterisks ( or *) indicate a significant difference of expression levels between WT and each transgenic line at P<0.01 or 0.001 by Student's t-test.

Figure 23:
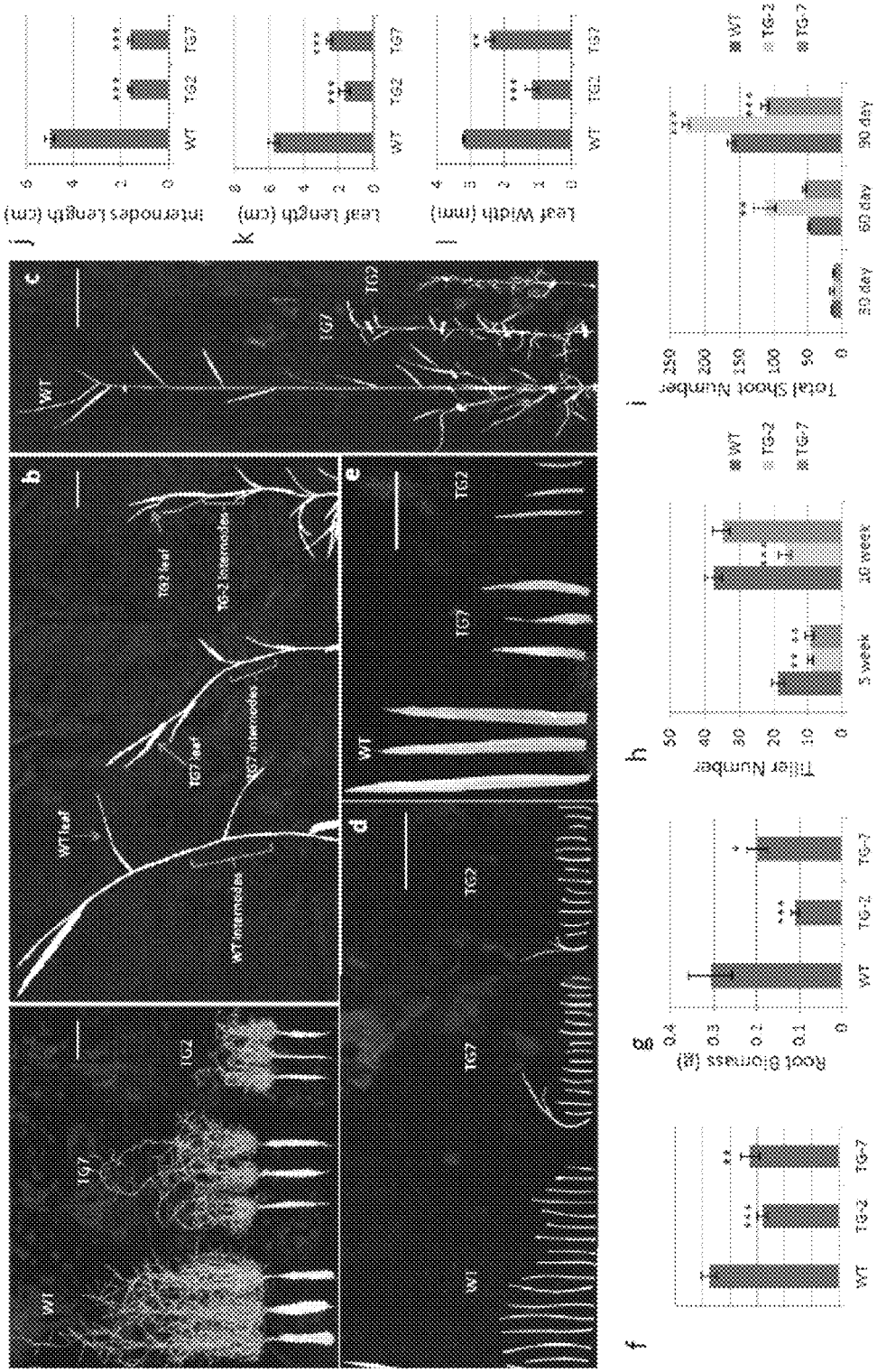

FIG. 23. Plant tillering and development. (panel a) Ten-week-old WT and TG plants initiated from a single tiller. Scale bar, 10 cm. (panel b) Representative leaves and internodes of WT and TG plants initiated from single tillers. Scale bar, 2 cm. (panel c) Close up of the longest tillers from WT and TG plants, respectively. Scale bar, 5 cm. (panel d) All internodes from the representative longest tiller were sliced from top to bottom and arranged from left to right. Scale bar, 5 cm. (panel e) Top three fully developed leaves from the representative tillers of WT and TG plants. Scale bar, 2 cm. (panel f) Shoot dry weight of WT and TG plants at 10 weeks after initiation from a single tiller (n=4). (panel g) Root dry weight of WT and TG plants at 10 weeks after initiation from a single tiller (n=4). (panel h) Tiller number in WT and TG plants at five and ten weeks after initiation from a single tiller (n=5). (panel i) Total shoot number including both tillers and lateral shoots in WT and TG plants at 30, 60, and 90 days after initiation from a single tiller (n=5). (panel j) A panel average length of top eight internodes from WT and TG tillers (n=6). (panel k) Leaf length and (panel l) leaf width from the representative WT and two transgenic lines (n=3). Data are presented as means, and error bars represent ±SE. Asterisks (*, , or *) indicate a significant difference between WT and each transgenic line at P<0.05, 0.01, or 0.001 by Student's t-test.

Figure 24:
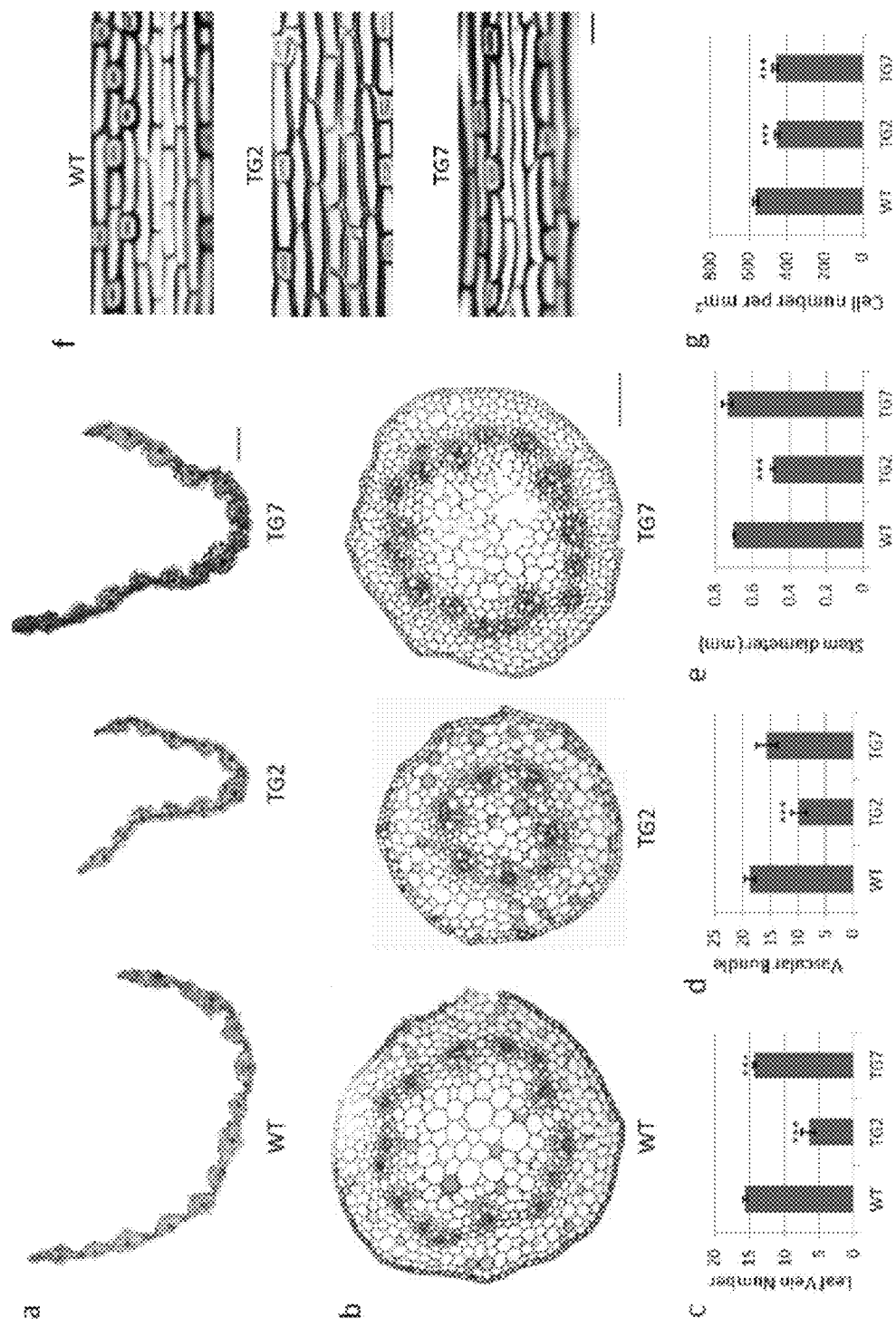

FIG. 24. Histological analysis of leaf and stem of WT and TG plants. (panel a) Cross-section images of WT and TG leaves. Scale bar, 100 μm. (panel b) Cross-section images of WT and TG stems. Scale bar, 100 μm. (c) Statistical analysis of leaf vein number between representative WT and TG plants (n=5). (panel d) Statistical analysis of the number of vascular bundles between representative WT and TG stems (n=5). (panel e) Statistical analysis of stem diameter between WT and two transgenic lines (n=5). (panel f) The representative leaf epidermis of WT and two transgenic lines. Scale bar, 50 μm. (panel g) The number of leaf epidermis cells between WT and two transgenic lines (n=5). Data are presented as means, and error bars represent ±SE. Asterisks (***) indicate a significant difference between WT and each transgenic line at P<0.001 by Student's t-test.

Figure 25:
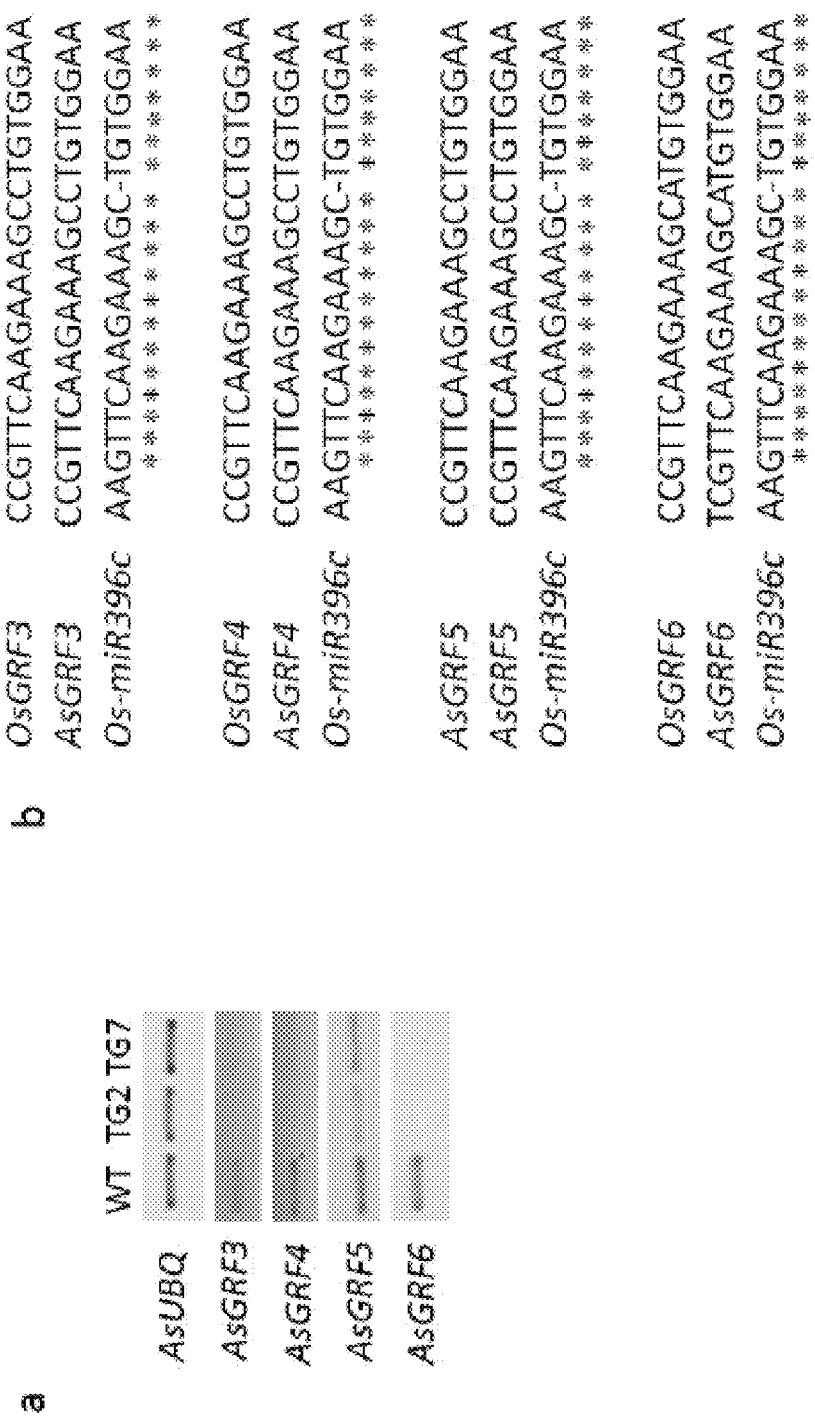

FIG. 25. Identification of putative miR396c target sequences in creeping bentgrass. (panel a) Semi-quantitative RT-PCR analysis of AsGRF3, AsGRF4, AsGRF5, and AsGRF6 expression in WT and TG plants. AsUBQ5 was used as an endogenous control. (panel b) A comparison of miR396c target sites (SEQ ID NO:21) in the putative targets AsGRF3, AsGRF4, AsGRF5, and AsGRF6 between rice (SEQ ID NOS:22 and 24) and creeping bentgrass (SEQ ID NOS: 23 and 25). Asterisks indicate the identical RNA sequences.

Figure 26:
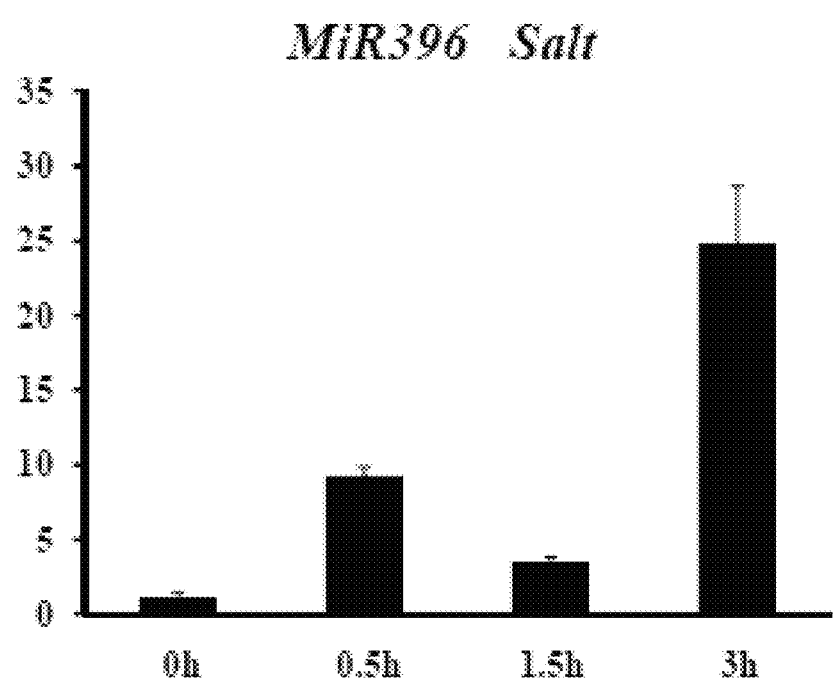

FIG. 26. Expression profile for miR396 in creeping bentgrass under salt stress.

Figure 27:
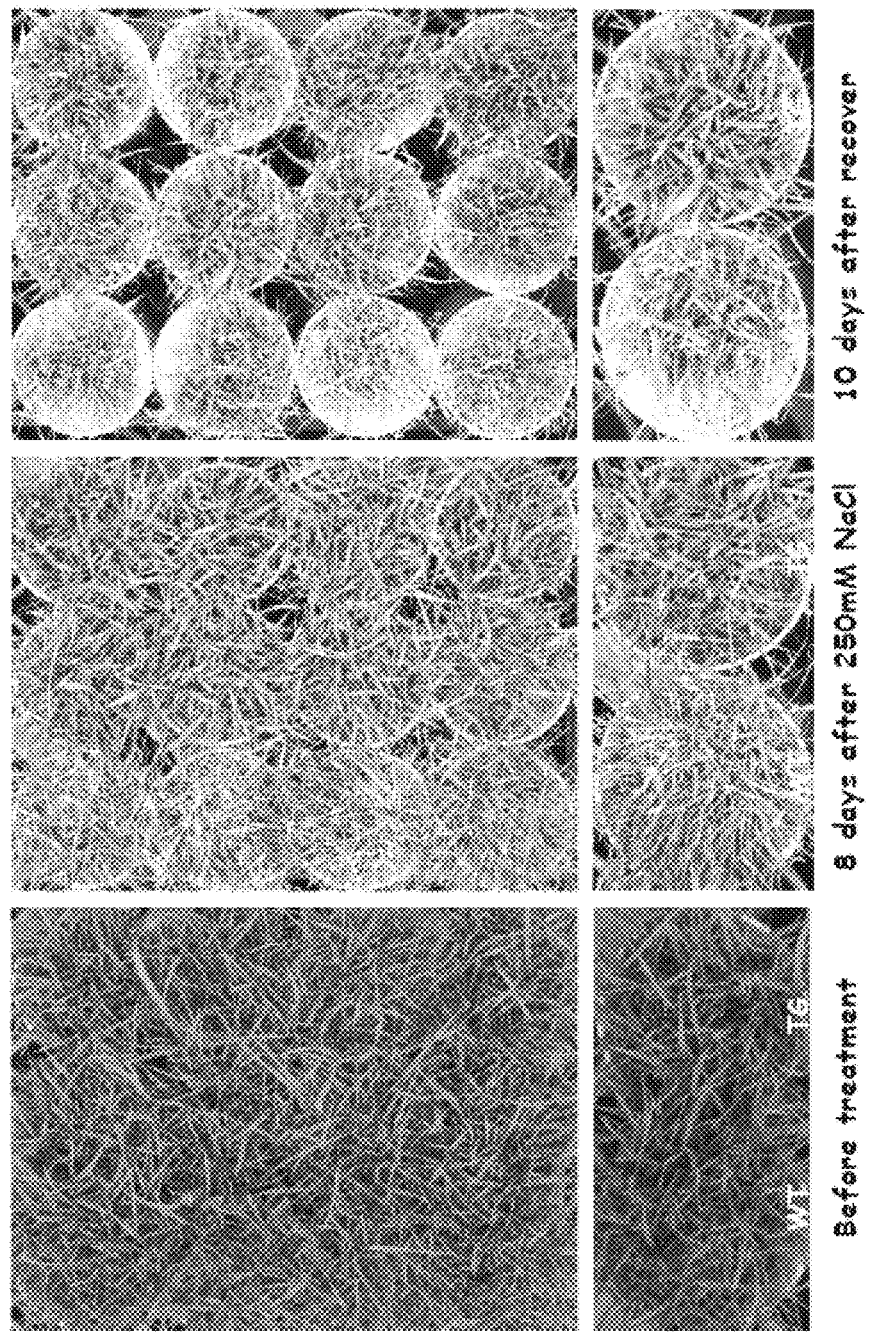
Figure 28:
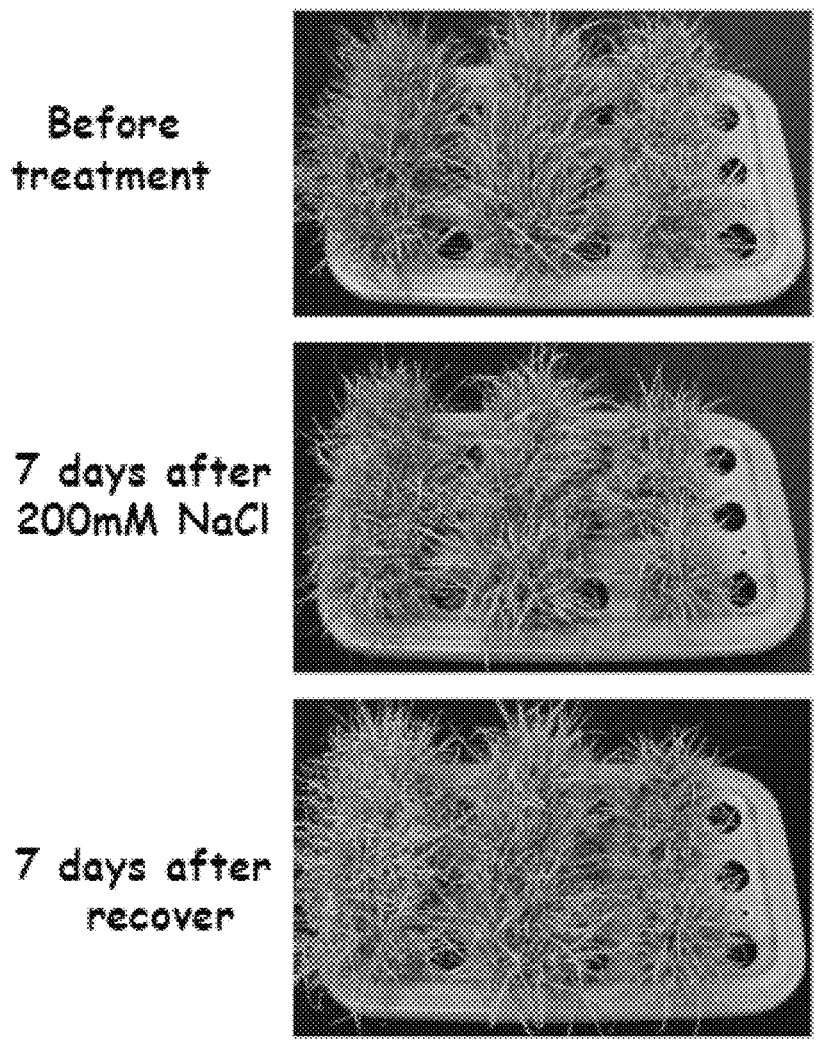

FIGS. 27 and 28. Overexpression of rice miR396 leads to enhanced salt tolerance in transgenic turfgrass plants.

Figure 29:
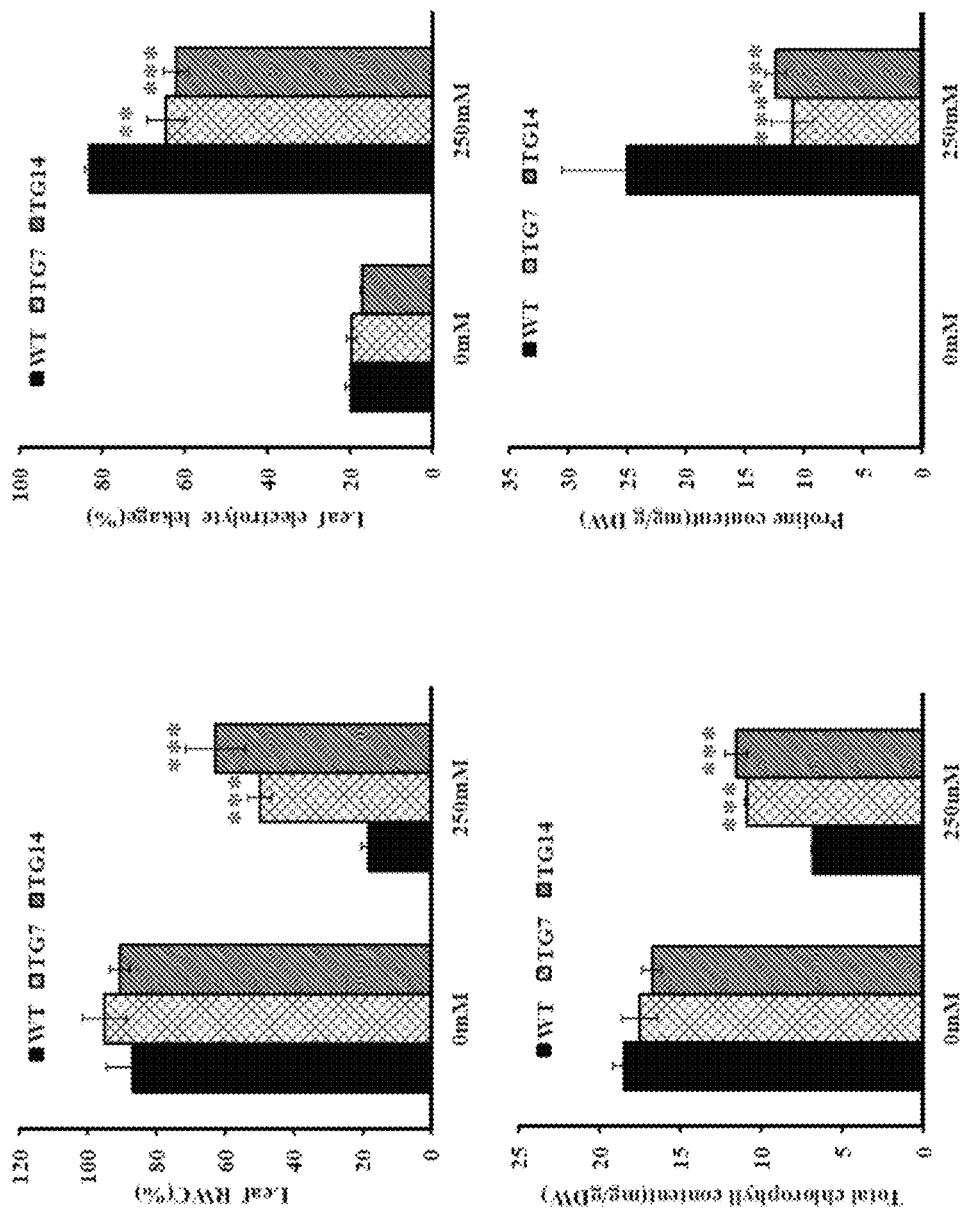

FIG. 29. Comparison of leaf RWC, leaf electrolyte leakage, total chlorophyll content, and proline content in two TG lines with WT creeping bentgrass.

Figure 30:
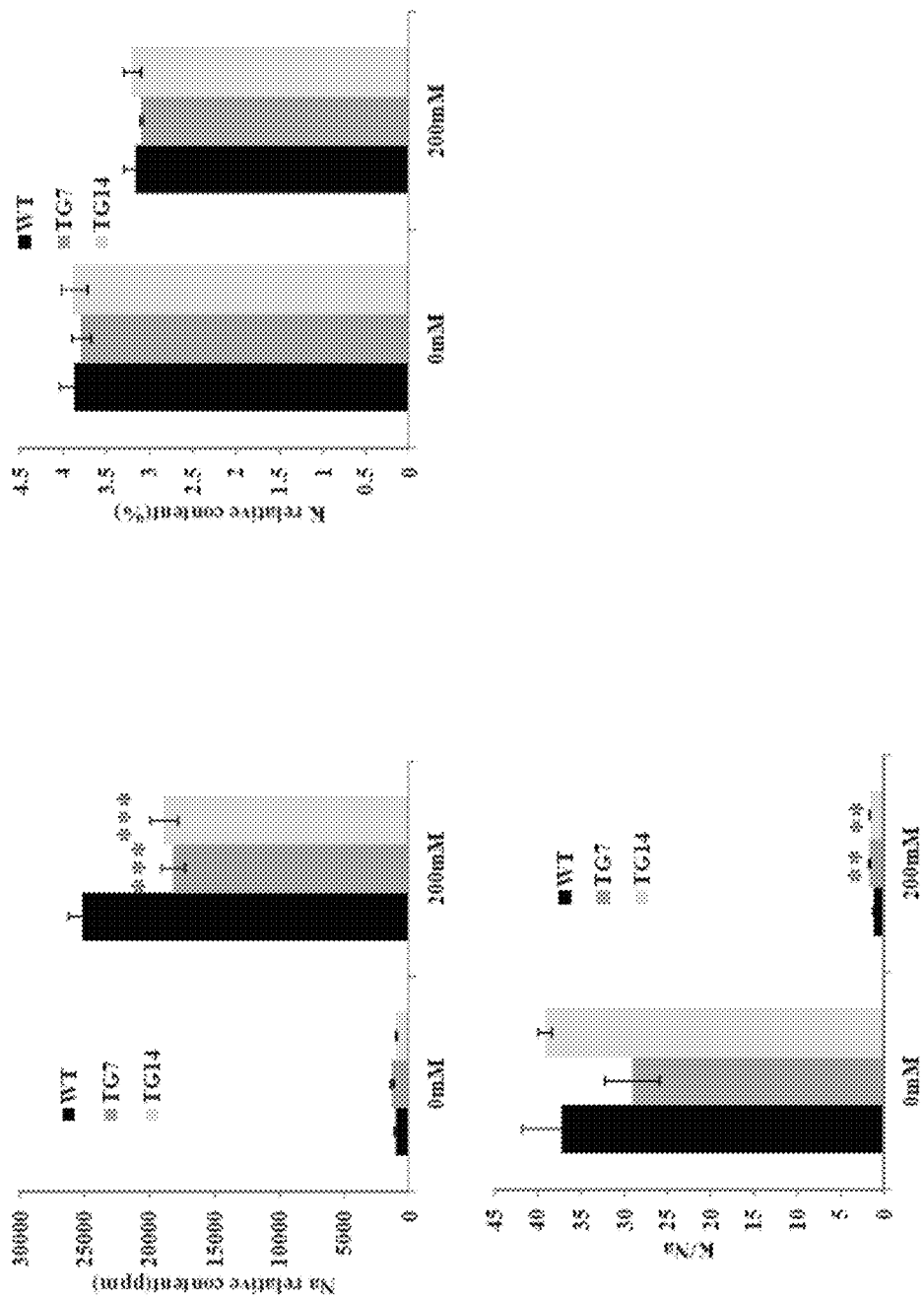

FIG. 30. Sodium and potassium content in wild-type and transgenic creeping bentgrass under normal conditions and under salt stress.

DETAILED DESCRIPTION OF THE INVENTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety The present invention is based in part on the unexpected discovery that the microRNA, miR396c, when overexpressed in a transgenic plant results in the plant having increased tolerance to cold and the ability to flower without vernalization, as compared to a plant that is not transformed with miR396c and therefore does not overexpress miR396c. The level of expression (e.g., overexpression) of a recombinant nucleic acid molecule comprising miR396c is as compared to the level of expression of an endogenous miR396c in a non-transgenic wild-type plant.

Thus, in one embodiment, the present invention provides a transgenic plant having increased cold tolerance, altered flowering characteristics (i.e., flowering bypassing vernalization requirement) defective pollen (e.g., male sterility) and/or altered plant development, comprising a recombinant nucleic acid molecule, said recombinant nucleic acid molecule comprising a nucleotide sequence encoding miR396c operatively associated with a promoter, wherein overexpression of the nucleotide sequence encoding miR396c confers increased cold tolerance, flowering bypassing vernalization requirement, defective pollen (e.g., male sterility) and/or altered plant development as compared with a plant that does not comprise said recombinant nucleic acid molecule comprising a nucleotide sequence encoding miR396c operatively associated with a promoter.

As used herein, the term "vernalization" refers to the acquisition of a plant's ability to flower or germinate in the spring by exposure to the prolonged cold of winter. Many temperate plants have a vernalization requirement and must experience a period of low winter temperature to initiate or accelerate the flowering process, or, as the case with many fruit tree species, to actually break dormancy, prior to flowering. Many plant species, including some ecotypes of *Arabidopsis thaliana* and winter cereals such as wheat, must go through a prolonged period of cold before flowering occurs. This ensures that reproductive development and seed production occurs at the optimum environmentally favorable time, normally following the passing of winter. The needed cold is often expressed in chill hours.

Following vernalization, plants have acquired the competence to flower, although they may require additional seasonal cues or weeks of growth before they will actually flower. One of the most important influences that temperature has on the floral transition is the vernalization response. Vernalization activates a plant hormone called florigen present in the leaves which induces flowering at the end of the chilling treatment. Some plant species do not flower without vernalization. Many biennial species have a vernalization period, which can vary in period and temperature. Typical vernalization temperatures are between 5 and 10 degrees Celsius (40 and 50 degrees Fahrenheit).

In some embodiments of the transgenic plant of this invention, the nucleotide sequence encoding miR396c can comprise, consist essentially of or consist of, the nucleotide sequence of SEQ ID NO:1. (GenBank Accession No. AK062523.1). In some embodiments of the transgenic plant of this invention, wherein the promoter can be an actin promoter, a CaMV35S promoter or a ubiquitin promoter, including any combination thereof.

In some embodiments, the transgenic plant of this invention can be a monocot plant or a dicot plant. In some embodiments, the transgenic plant of this invention can be a perennial plant or an annual plant. In particular embodiments of this invention, the transgenic plant is a perennial monocot.

In some embodiments the plant of this invention can be any plant that requires vernalization for flowering. Nonlimiting examples of a plant of this invention include turf grass plant, winter wheat, rice, corn, cotton, soybean, wheat, and any other crop plant now known or later identified.

In further embodiments, the present invention provides a method of producing a transgenic plant having increased cold tolerance and altered flowering characteristics (e.g., flowering bypassing vernalization requirement) defective pollen (e.g., male sterility) and/or altered plant development, comprising: a) transforming a plant cell with a recombinant nucleic acid molecule, said recombinant nucleic acid molecule comprising a nucleotide sequence encoding miR396c or other members of the miRNA 396 (e.g., miR396a, miR396b, miR396d, miR396e, miR396f) gene family operatively associated with a promoter; and b) regenerating a transgenic plant from the transformed plant cell, thereby producing a transgenic plant having increased cold tolerance and altered flowering characteristics (i.e., flowering bypassing vernalization requirement) defective pollen and/or altered plant development as compared with a plant that is not transformed with said recombinant nucleic acid molecule. In some embodiments of the method described above, the nucleotide sequence encoding miR396c can comprise, consist essentially of or consist of the nucleotide sequence of SEQ ID NO:1. In some embodiments of the method described above, the promoter can be an actin promoter, a CaMV35S promoter, a ubiquitin promoter or any combination thereof.

Also provided herein is a transgenic plant having increased cold tolerance and altered flowering characteristics (i.e., flowering bypassing vernalization requirement) defective pollen and/or altered plant development produced by the methods of this invention.

Further provided herein is a crop comprising a plurality of transgenic plants of this invention, planted together in an agricultural field, a golf course, a residential lawn, a road side, an athletic field, and/or a recreational field, in any combination.

In some embodiments, the present invention provides a nucleic acid construct comprising, in the following order from 5' to 3': a) a first promoter; b) a nucleotide sequence encoding miR396c; c) a first termination sequence; d) a second promoter; e) a nucleotide sequence encoding a selectable marker operably associated with the promoter of (d); and f) a second termination sequence.

In a particular embodiment, the present invention provides a nucleic acid construct, comprising in the following order from 5' to 3': a) a first CaMV35S promoter; b) a nucleotide sequence encoding miR396c; c) a first nos sequence; d) a second CaMV35S promoter; e) a nucleotide sequence encoding hygromycin; and f) a second nos sequence.

Also provided herein is a transformed plant cell comprising the nucleic acid construct of this invention, as well as transgenic plant comprising the nucleic acid construct of this invention and/or the transformed plant cell of this invention. Also provided herein is a transgenic seed from the transgenic plant of this invention.

Further provided herein is a method of producing a transgenic plant having increased cold tolerance, altered flowering characteristics (e.g., flowering bypassing vernalization requirement), defective pollen and/or altered plant development, comprising: a) transforming a cell of a plant with the nucleic acid construct of this invention; and b) regenerating the transgenic plant from the transformed plant cell, wherein the plant has increased cold tolerance, altered flowering characteristics (i.e., flowering bypassing vernalization requirement), defective pollen (e.g., as described in the Examples section herein, and/or altered plant development (e.g., as described in the Examples section herein), as compared with a plant that is not transformed with the nucleic acid construct of this invention. Additionally provided is a transgenic plant produced by the method described above, as well as a crop comprising a plurality of plants produced by the methods described herein, planted together in an agricultural field, a gold course, a residential lawn, a road side, an athletic field and/or a recreational field.

Any nucleotide sequence encoding a member of the miR396 microRNA family is suitable for the compositions and methods of the invention. Non-limiting examples include the nucleotide sequences encoding miR396a of *Arabidopsis*, miR396b of *Arabidopsis*, miR396a of rice (*Oryza*), miR296b of rice, miR396c of rice, miR396d of rice, miR396e of rice, miR396f of rice, and/or any combination thereof, as well as any other nucleotide sequence encoding miR396 family members now known or later identified.

As would be understood by those of skill in the art, any portion of a nucleotide sequence encoding miR396 that can function as a microRNA is useful in the present invention. Accordingly, any portion of a miR396 nucleotide sequence that comprises the stem-loop structure of the miR396 nucleotide sequence can be used to prepare the recombinant nucleic acid molecules of the invention. In particular embodiments, the nucleotide sequence encoding miR396c can comprise, consist essentially of, or consist of the nucleotide sequence of SEQ ID NO:1.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the present invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of this invention has at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 100%) sequence identity to the nucleotide sequences of the present invention (e.g., SEQ ID NO:1).

To facilitate expression, the recombinant nucleic acid molecules and/or nucleotide sequences of this invention can be operatively associated with one or more promoters. Thus, in some embodiments, the miR396 nucleotide sequence of the invention is operatively associated with a promoter for expression or overexpression of the miR396 nucleotide sequence. As used herein, the level of overexpression of a recombinant nucleic acid molecule comprising miR396 is as compared to the level of expression of an endogenous miR396 in a non-transgenic wild-type plant.

As used herein, the term "promoter" refers to a region of a nucleotide sequence that provides signals for the expression of a nucleotide sequence operatively associated with the promoter. This may include sequences to which an RNA polymerase binds, but is not limited to such sequences and can include regions to which other regulatory proteins bind, together with regions involved in the control of protein translation and can also include coding sequences. Furthermore, a "promoter" of this invention is a promoter (e.g., a nucleotide sequence) capable of initiating transcription of a nucleic acid molecule in a cell of a plant.

The selection of promoters useable with the present invention can be made among many different types of promoters. Thus, the choice of promoter depends upon several factors, including, but not limited to, cell- or tissue-specific expression, desired expression level, efficiency, inducibility and/or selectability. For example, where expression in a specific tissue or organ is desired in addition to inducibility, a tissue-specific promoter can be used (e.g., a root specific promoter). In contrast, where expression in response to a stimulus is desired, a promoter inducible by other stimuli or chemicals can be used. Where continuous expression is desired throughout the cells of a plant, a constitutive promoter can be chosen.

Non-limiting examples of constitutive promoters include cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter.

Some non-limiting examples of tissue-specific promoters useable with the present invention include those encoding seed storage proteins (e.g., β-conglycinin, cruciferin, napin phaseolin, etc.), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Thus, the promoters associated with these tissue-specific nucleic acids can be used in the present invention.

Additional examples of tissue-specific promoters include, but are not limited to, the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants,* Hollaender ed., Plenum Press 1983; and Poulsen et al. (1986) *Mol. Gen. Genet.* 205:193-200)), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *petunia* chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Physiol* 1:1175-1183), and chalcone synthase promoters (Franken et al. (1991) *EMBO J.* 10:2605-2612). Particularly useful for seed-specific expression is the pea vicilin promoter (Czako et al. (1992) *Mol. Gen. Genet.* 235:33-40; as well as U.S. Pat. No. 5,625,136). Other useful promoters for expression in mature leaves are those that are switched on at the onset of senescence, such as the SAG promoter from *Arabidopsis* (Gan et al. (1995) *Science* 270:1986-1988).

In addition, promoters functional in plastids can be used. Non-limiting examples of such promoters include the bacteriophage T3 gene 9 5' UTR and other promoters disclosed in U.S. Pat. No. 7,579,516. Other promoters useful with the present invention include but are not limited to the S-E9 small subunit RuBP carboxylase promoter and the Kunitz trypsin inhibitor gene promoter (Kti3).

In some embodiments, inducible promoters can be used with the present invention. Examples of inducible promoters useable with the present invention include, but are not limited to, tetracycline repressor system promoters, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters. Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421) the benzene sulphonamide-inducible promoters (U.S. Pat. No. 5,364,780) and the glutathione S-transferase promoters. Likewise, one can use any appropriate inducible promoter described in Gatz (1996) *Current Opinion Biotechnol.* 7:168-172 and Gatz (1997) *Annu. Rev. Plant Physiol. Plant Mol. Biol.* 48:89-108.

Thus, any promoter known to those of skill in the art for expression of a nucleotide sequence in a plant can be used with the compositions and methods of the invention. In particular embodiments, the nucleotide sequence encoding miR396 (e.g., (miR296c) is operatively associated with an actin promoter, a CaMV35S promoter and/or a ubiquitin promoter.

In further embodiments, the present invention provides transgenic plant cells, transgenic plants, and/or transgenic plant parts comprising a recombinant nucleic acid of the invention (i.e., transgenic plants comprising a recombinant nucleic acid that comprises a nucleotide sequence encoding miR396c) and methods of producing such plants. The transgenic plant cell, plant and/or plant part of the invention can be stably transformed or transiently transformed.

Additionally, crops comprising a plurality of transgenic plants of the invention are provided. Nonlimiting examples of types of crops comprising a plurality of transgenic plants of the invention include an agricultural field, a golf course, a residential lawn, a road side, an athletic field, and/or a recreational field.

As used herein, "plant" means any plant and thus includes, for example, angiosperms, gymnosperms, bryophytes, ferns and/or fern allies. In some embodiments, the plant cell and/or plant of the invention can be a cell and/or plant of any plant species. Non-limiting examples of plants of the present invention include turf grasses, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin), radishes, dry bulb onions, rutabaga, eggplant, salsify, escarole, shallots, endive, garlic, spinach, green onions, squash, greens, beet (sugar beet and fodder beet), sweet potatoes, swiss chard, horseradish, tomatoes, turnips, and spices; a fruit and/or vine crop such as apples, apricots, cherries, nectarines, peaches, pears, plums, prunes, cherry, quince, almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pomes, melon, mango, papaya, and lychee, a field crop plant such as clover, alfalfa, evening primrose, meadow foam, corn/maize (field, sweet, popcorn), hops, jojoba, peanuts, rice, safflower, small grains (barley, oats, rye, wheat, etc.), sorghum, tobacco, kapok, a leguminous plant (beans, lentils, peas, soybeans), an oil plant (rape, mustard, poppy, olive, sunflower, coconut, castor oil plant, cocoa bean, groundnut), *Arabidopsis*, a fiber plant (cotton, flax, hemp, jute), lauraceae (cinnamon, camphor), or a plant such as coffee, sugar cane, tea, and natural rubber plants; and/or a bedding plant such as a flowering plant, a cactus, a succulent and/or an ornamental plant, as well as trees such as forest (broad-leaved trees and evergreens, such as conifers), fruit, ornamental, and nut-bearing trees, as well as shrubs and other nursery stock.

In particular embodiments, a plant cell and/or plant of the invention can be a turfgrass. As used herein, turfgrass includes, but is not limited to, *Sporobolus airiodes, Puccinellia distans, Paspalum notatum, Cynodon dactylon, Buchloe dactyloides, Cenchrus ciliaris, Hordeum californicum, Hordeum vulgare, Hordeum brachyantherum, Agrostis capillaries, Agrostis palustris, Agrostis exerata, Briza maxima, Poa annua, Poa ampla, Poa canbyi, Poa compressa, Poa pratensis, Poa scabrella, Poa trivialis, Poa secunda, Andropogon gerardii, Schizachyruim scoparium, Andropogon hallii, Bromus arizonicus, Bromus carinatus, Bromus biebersteinii, Bromus marginatus, Bromus rubens, Bromus inermis, Buchloe dactyloides, Axonopus fissifolius, Eremochloa ophiuroides, Muhlenbergia rigens, Sporobolus cryptandrus, Sporobolus heterolepis, Tripsacum dactyloides, Festuca arizonica, Festuca rubra* var. *commutate, Festuca rubra* var. *rubra, Festuca megalura, Festuca longifolia, Festuca idahoensis, Festuca elatior, Fescue rubra, Fescue ovina* var. *ovina, Festuca arundinacea, Alopecurus arundinaceaus, Alopecurus pratensis, Hilaria jamesii, Bouteloua eriopoda, Bouteloua gracilis, Bouteloua curtipendula, Deschampsia caespitosa, Oryzopsis hymenoides, Sorghastrum nutans, Eragrostis trichodes, Eragrostis curvula, Melica californica, Stipa comate, Stipa lepida, Stipa viridula, Stipa cernua, Stipa pukhra, Dactylis glomerata, Koeleria pyramidata, Calamovilfa longifolia, Agrostis alba, Phalaris arundinacea, Stenotaphrum secundatum, Spartina pectinata, Lolium multiflorum, Lolium perenne, Leptochloa dubia, Sitanion hystrix, Panicum virgatum, Aristida purpurea, Phleum pretense, Agropyron spicatum, Agropyron cristatum, Agropyron desertorum, Agropyron intermedium, Agropyron trichophorum, Agropyron trachycaulum, Agropyron riparium, Agropyron elongatum, Agropyron smithii, Elymus glaucus, Elymus Canadensis, Elymus triticoides, Elymus junceus, Zoysia japonica, Zoysia matrella,* and *Zoysia tenuifolia*. In some embodiments, a plant of the present invention can be creeping bent grass, *Agrostis palustris*.

As used herein, abiotic stress refers to outside, nonliving factors which can be harmful to plants. Non-limiting examples of abiotic stress include drought, high or excessive salinity, low or cold temperature, freezing, heat or high temperature, high light intensity, ozone and/or any combination thereof. In particular embodiments of the invention, the abiotic stress is cold temperature.

The terms "reduce," "reduced," "reducing" or "reduction" (and other grammatical variations thereof) as used herein means diminished, a decrease in, or a diminution in, for example, plant size, as a response to abiotic stress.

"Increase, "increased, or "increasing" (and other grammatical variations thereof) as used herein means an enhancement or augmentation of, for example, the growth of a plant, as a response to alleviating abiotic stress to which the plant is exposed.

Thus, an "increased tolerance to cold" or "enhanced tolerance to cold" as used herein refers to the ability of a plant or part thereof exposed to cold temperature and transformed with the recombinant nucleic acid molecules of the invention to withstand the effects of the cold temperature better than a control plant or part thereof (i.e., a plant or part thereof that has been exposed to the same cold temperature but has not been transformed with the recombinant nucleic acid molecules of the invention).

Increased tolerance to abiotic stress can be measured using a variety of parameters including, but not limited to, the size and number of plants or parts thereof, relative water content, electrolyte leakage, stomata conductance, photosynthetic rate, internal $CO_2$ concentration, transpiration rate and/or chlorophyll fluorescence. Thus, in some embodiments of this invention, a transformed plant or part thereof comprising a recombinant nucleic acid molecule of the invention, thereby having increased tolerance to the abiotic stress, would have, for example, greater growth as compared to a plant or part thereof exposed to the same stress but not having been transformed with the said recombinant nucleic acid molecule. An increased tolerance to abiotic stress can be an increase in tolerance of about 10%, 20%, 30%, 40%, 50%, 60%, 70%, 80%, 90%, 100%, or any range therein, as compared to a control plant.

The present invention further provides a product harvested from a transgenic plant and/or part thereof of the invention, wherein the product comprises said recombinant nucleic acid molecule. Nonlimiting examples of a harvested product include a seed, a leaf, a stem, a shoot, a fruit, flower, root, and/or extract. In some embodiments, a processed product produced from the harvested product is provided. Nonlimiting examples of a processed product include a protein, an extract, a medicinal product (e.g., artemicin as an antimalarial agent), a biofuel (e.g., ethanol), and/or a fragrance.

Definitions

As used in the description of the embodiments of the invention and the appended claims, the singular forms "a," "an," and "the" are intended to include the plural forms as well, unless the context clearly indicates otherwise.

As used herein, "and/or" refers to and encompasses any and all possible combinations of one or more of the associated listed items.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

The terms "comprise," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The terms "nucleotide sequence" "nucleic acid," "nucleic acid molecule," "oligonucleotide" and "polynucleotide" are used interchangeably herein to refer to a heteropolymer of nucleotides and encompass both RNA and DNA, including cDNA, genomic DNA, mRNA, synthetic (e.g., chemically synthesized) DNA or RNA and chimeras of RNA and DNA. The term nucleic acid refers to a chain of nucleotides without regard to length of the chain. A nucleic acid can be double-stranded or single-stranded. Where single-stranded, the nucleic acid can be a sense strand or an antisense strand. A nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. Nucleic acid sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). In some embodiments, a gene refers to only the coding region. A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and Sequence Analysis Primer (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," in the context of two nucleic acid molecules, nucleotide sequences or protein sequences, refers to two or more sequences or subsequences that have at least about 70%, least about 75%, at least about 80%, least about 85%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 50 residues to about 150 residues in length. Thus, in some embodiments of this invention, the substantial identity exists over a region of the sequences that is at least about 50, about 60, about 70, about 80, about 90, about 100, about 110, about 120, about 130, about 140, about 150, or more residues in length. In some particular embodiments, the sequences are substantially identical over at least about 150 residues. In a further embodiment, the sequences are substantially identical over the entire length of the coding regions. Furthermore, in representative embodiments, substantially identical nucleotide or protein sequences perform substantially the same function (e.g., conferring increased resistance to a nematode plant parasite, reducing the growth of a nematode plant parasite, reducing cyst development).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially identical when the two sequences hybridize to each other under stringent conditions. In some representative embodiments, two nucleotide sequences considered to be substantially identical hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the present invention. In one embodiment, a reference nucleotide sequence hybridizes to the "test" nucleotide sequence in 7% sodium dodecyl sulfate (SDS), 0.5 M $NaPO_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M $NaPO_4$, 1 mM EDTA at 50° C. with washing in 1×SSC, 0.1% SDS at 50° C. or in 7% sodium dodecyl sulfate (SDS), 0.5 M $NaPO_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M $NaPO_4$, 1 mM EDTA at 50° C. with washing in 0.1×SSC, 0.1% SDS at 50° C., or in 7% sodium dodecyl sulfate (SDS), 0.5 M $NaPO_4$, 1 mM EDTA at 50° C. with washing in 0.1×SSC, 0.1% SDS at 65° C.

An "isolated" nucleic acid molecule or nucleotide sequence or an "isolated" polypeptide is a nucleic acid molecule, nucleotide sequence or polypeptide that, by the hand of man, exists apart from its native environment and/or has a function that is different, modified, modulated and/or altered as compared to its function in its native environment and is therefore not a product of nature. An isolated nucleic acid molecule or isolated polypeptide may exist in a purified form or may exist in a non-native environment such as, for example, a recombinant host cell. Thus, for example, with respect to polynucleotides, the term isolated means that it is separated from the chromosome and/or cell in which it naturally occurs. A polynucleotide is also isolated if it is separated from the chromosome and/or cell in which it naturally occurs and is then inserted into a genetic context, a chromosome, a chromosome location, and/or a cell in which it does not naturally occur. The recombinant nucleic acid molecules and nucleotide sequences of the invention can be considered to be "isolated" as defined above.

Thus, an "isolated nucleic acid molecule" or "isolated nucleotide sequence" is a nucleic acid molecule or nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid molecule encoding an additional polypeptide or peptide sequence. An "isolated nucleic acid molecule" or "isolated nucleotide sequence" can also include a nucleotide sequence derived from and inserted into the same natural, original cell type, but which is present in a non-natural state, e.g., present in a different copy number, and/or under the control of different regulatory sequences than that found in the native state of the nucleic acid molecule.

The term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not necessarily mean that the preparation is technically pure (homogeneous), but it is sufficiently pure to provide the polypeptide or nucleic acid in a form in which it can be used for the intended purpose.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

As used herein, "heterologous" refers to a nucleic acid molecule or nucleotide sequence that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants.

In addition, a heterologous nucleotide sequence includes a nucleotide sequence derived from and inserted into the same natural, original cell type, but which is present in a non-natural state, e.g. present in a different copy number, and/or under the control of different regulatory sequences than that found in the native state of the nucleic acid molecule.

"Wild-type" nucleotide sequence or amino acid sequence refers to a naturally occurring ("native") or endogenous nucleotide sequence or amino acid sequence. Thus, for example, a "wild-type mRNA" is an mRNA that is naturally occurring in or endogenous to the organism. A "homologous" nucleotide sequence is a nucleotide sequence naturally associated with a host cell into which it is introduced.

By the term "express" or "expression" of a polynucleotide coding sequence, it is meant that the sequence is transcribed, and optionally translated.

"Nucleotide sequence of interest" refers to any nucleotide sequence which, when introduced into a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "nucleotide sequence of interest" may also be one that is transferred to plants for the production of commercially valuable enzymes or metabolites in the plant.

As used herein, the phrases "operably linked," "operatively linked," "operatively associated" or "in operative association" and the like, mean that elements of a nucleic acid construct such as an expression cassette or nucleic acid molecule are configured so as to perform their usual function. Thus, regulatory or control sequences (e.g., promoters) operatively associated with a nucleotide sequence are capable of effecting expression of the nucleotide sequence. For example, a promoter in operative association with a nucleotide sequence encoding miR396c would be capable of effecting the expression of that miR396c nucleotide sequence.

The control sequences need not be contiguous with the nucleotide sequence of interest, as long as they function to direct the expression thereof. Thus, for example, intervening untranslated, yet transcribed, sequences can be present between a promoter and a coding sequence, and the promoter sequence can still be considered "operably linked" to the coding sequence.

As used herein, the terms "transformed" and "transgenic" refer to any plant, plant cell, callus, plant tissue, or plant part that contains all or part of at least one recombinant (e.g., heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

The term "introducing" or "introduce" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, a transgenic plant cell, plant and/or plant part of the invention can be stably transformed or transiently transformed.

The term "plant part," as used herein, includes but is not limited to embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

"Transient transformation" in the context of a polynucleotide means that a polynucleotide is introduced into the cell and does not integrate into the genome of the cell.

As used herein, "stably introducing," "stably introduced," "stable transformation" or "stably transformed" in the context of a polynucleotide introduced into a cell, means that the introduced polynucleotide is stably integrated into the genome of the cell, and thus the cell is stably transformed with the polynucleotide. As such, the integrated polynucleotide is capable of being inherited by the progeny thereof, more particularly, by the progeny of multiple successive generations. "Genome" as used herein includes the nuclear and/or plastid genome, and therefore includes integration of a polynucleotide into, for example, the chloroplast genome. Stable transformation as used herein can also refer to a polynucleotide that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a plant). Stable transformation of a cell can be detected by, for example, a Northern blot hybridization assay of RNA of the cell with nucleic acid sequences which specifically hybridize with a nucleotide sequence of a nucleic acid molecule introduced into a plant or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods. Transformation can also be detected by direct sequencing and/or hybridization protocols well known in the art.

Transformation

Procedures for transforming plants are well known and routine in the art and are described throughout the literature. Non-limiting examples of methods for transformation of plants include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Mild et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

Thus, in some particular embodiments, the introducing into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethyleneglycol-mediated transformation, any other electrical, chemical, physical and/or biological mechanism that results in the introduction of nucleic acid into the plant, plant part and/or cell thereof, or a combination thereof.

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen & Willmitzer (1988) *Nucleic Acids Res.* 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos.

4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

Thus, in particular embodiments of the present invention, a plant cell can be transformed by any method known in the art and intact plants can be regenerated from these transformed cells using any of a variety of known techniques. Thus, a plant cell transformed with a nucleic acid molecule of the invention can be regenerated by methods well known in the art to produce a transformed plant or plant part of the invention. Plant regeneration from plant cells, plant tissue culture and/or cultured protoplasts is described, for example, in Evans et al. (*Handbook of Plant Cell Cultures*, Vol. 1, MacMillan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed, transgenic plants, plant cells and/or plant tissue culture are routine in the art and can be employed in the methods of the invention provided herein.

Likewise, the genetic properties engineered into the transgenic seeds and plants, plant parts, and/or plant cells of the present invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A nucleotide sequence therefore can be introduced into the plant, plant part and/or plant cell in any number of ways that are well known in the art. The methods of the invention do not depend on a particular method for introducing one or more nucleotide sequences into a plant, only that they gain access to the interior of at least one cell of the plant. Where more than one nucleotide sequence is to be introduced, the respective nucleotide sequences can be assembled as part of a single nucleic acid construct/molecule, or as separate nucleic acid constructs/molecules, and can be located on the same or different nucleic acid constructs/molecules. Accordingly, the nucleotide sequences can be introduced into a cell in a single transformation event, in separate transformation events, or, for example, in plants, as part of a breeding protocol.

In some embodiments of this invention, the introduced nucleic acid molecule may be maintained in the plant cell stably if it is incorporated into a non-chromosomal autonomous replicon or integrated into the plant chromosome(s). Alternatively, the introduced nucleic acid molecule may be present on an extra-chromosomal non-replicating vector and be transiently expressed or transiently active. Whether present in an extra-chromosomal non-replicating vector or a vector that is integrated into a chromosome, the nucleic acid molecule can be present in a plant expression cassette.

Nucleic Acid Constructs

A plant expression cassette or recombinant nucleic acid molecule can contain regulatory or control sequences that drive gene expression in plant cells that are operatively linked so that each sequence can fulfill its function, for example, termination of transcription by polyadenylation signals. Exemplary polyadenylation signals can be those originating from *Agrobacterium tumefaciens* t-DNA such as the gene known as octopine synthase of the Ti-plasmid pTiACH5 (Gielen et al. *EMBO J.* 3:835 (1984)) or functional equivalents thereof, but also all other terminators functionally active in plants are suitable.

Thus, some embodiments of the invention are directed to nucleic acid molecules and/or expression cassettes designed to express the nucleotide sequences and nucleic acid molecules of the invention. Accordingly, in some embodiments, "expression cassette" means a nucleic acid molecule having at least a regulatory or control sequence operatively linked to a nucleotide sequence encoding a miR396c. In this manner, for example, plant promoters in operable interaction or associated with the miR396c are provided in recombinant nucleic acid molecules and/or expression cassettes for expression in a plant, plant part and/or plant cell, thereby conferring increased tolerance to cold and flowering by bypassing the vernalization requirement.

As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. In addition to promoters, discussed above, regulatory sequences include, but are not limited to, enhancers, introns, Kozak sequences, translation leader sequences and polyadenylation signal sequences.

A number of non-translated leader sequences derived from viruses are known to enhance gene expression. Specifically, leader sequences from Tobacco Mosaic Virus (TMV, the "ω-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski et al. (1990) *Plant Mol. Biol.* 15:65-79). Other leader sequences known in the art include, but are not limited to, picornavirus leaders such as an encephalomyocarditis (EMCV) 5' non-coding region leader (Elroy-Stein et al. (1989) *Proc. Natl. Acad. Sci. USA* 86:6126-6130); polyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989) *Molecular Biology of RNA* 237-256); and MCMV leader (Lommel et al. (1991) *Virology* 81:382-385). See also, Della-Cioppa et al. (1987) *Plant Physiol.* 84:965-968.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operatively linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and the pea rbcs E9 terminator. These can be used in both monocotyledons and dicotyledons. In addition, a coding sequence's native transcription terminator can be used.

A signal sequence can be operatively linked to a nucleic acid molecule of the present invention to direct the nucleic acid molecule into a cellular compartment. In this manner, the expression cassette will comprise a nucleic acid molecule of the present invention operatively linked to a nucleotide sequence for the signal sequence. The signal sequence may be operatively linked at the N- or C-terminus of the nucleic acid molecule.

The expression cassette also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) 1 *Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hyg (hygromycin phosphotransferase) that confers resistance to hygromycin.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of this invention.

The present invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the present invention.

Examples

Example 1. Constitutive Expression of Os-MIR396c Alters Plant Development, Enhances Cold Tolerance, Bypasses Vernalization Requirement for Flowering and Results in Defective Pollen Development in Transgenic Creeping Bentgrass (*Agrostis stolonifera* L.)

In order to investigate miR396 function in perennial species and to analyze its molecular mechanisms, we generated an os-miR396c overexpression construct and introduced it into an economically important perennial crop, creeping bentgrass (*Agrostis stolonifera*). Transgenic creeping bentgrass displayed reduced leaf length and width, shorter internodes, less tiller number, reduced biomass, and more creeping in comparison with wild type (WT) controls. Under long-day growth conditions, transgenics flower within four weeks without vernalization, while WT controls require prolonged cold treatment. The transgenic spikelet is smaller and has fewer floralets than that of control. In addition, transgenics showed anther dehiscence defects and pollen sterility. During cold treatment, transgenics displayed greener and less wilted leaves than WT controls. RT-PCR analysis demonstrated that the expression levels of five putative targets from growth regulating factor family (GRFs) were repressed in transgenics. In addition, the expression profile of miR396's indirect targets involved in the vernalization pathway, floral development and male sterility, is under-detected via RT-PCR analysis and RNA-seq. These data indicate that miR396 is implicated in multiple plant physiological processes, indicating a role in developing new molecular strategies for enhanced crop yields via regulation of abiotic stress tolerance and flowering time.

Figure 1:
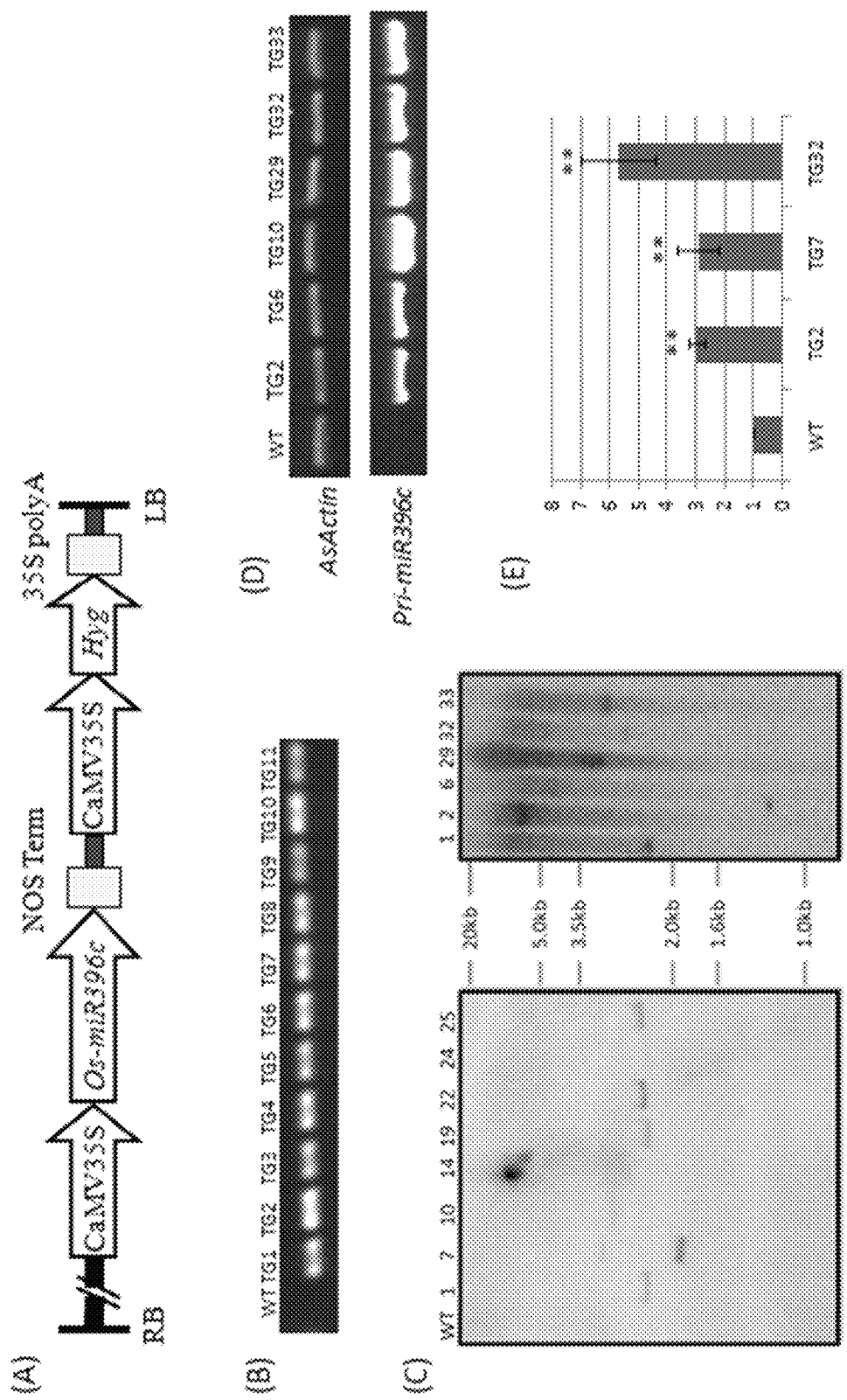
FIG. 1. Generation and molecular analysis of transgenic creeping bentgrass overexpressing Os-miR396c, a rice miRNA gene. (Panel A) schematic diagram of Os-miR396c gene overexpression construct, p35S-Os-miR396c/p35S-Hyg. Os-miR396c gene is under the control of Cauliflower Mosaic Virus (CaMV) 35S promoter and linked to the hygromycin resistance gene, Hyg, driven by CaMV 35S promoter. RB: right border; LB: left border. (Panel B) PCR analysis to amplify hyg gene in genomic DNA of transgenic (TG) and wild-type (WT) creeping bentgrass to determine the integration of Os-miR396c gene in the host genome. (Panel C) Example of Southern blot analysis of transgenic plants overexpressing Os-miR396c. (Panel D) RT-PCR analysis to detect the expression of primary Os-miR396c in the transcripts of TG and WT plants. (Panel E) stem-loop RT-qPCR analysis to detect the expression of mature Os-miR396c in the transcripts of TG and WT plants. The relative changes of gene expression were calculated based on $2^{-\Delta\Delta CT}$ method. AsActin was used as an endogenous control. Data are presented as average of three technical replicates, and error bars represent ±SE. Asterisks (**) indicate a significant difference of expression levels between WT and each transgenic line at P<0.01 by Student's t-test.

To study the role of miR396c involved in plant abiotic stress response and flowering time control in creeping bentgrass, we produced a miR396c overexpression construct, and introduced it into the genome of WT creeping bentgrass through *Agrobacterium tumefaciens* mediated transformation. The full length of Os-mi396c (GenBank® Accession No. AK062523.1) containing pre-miR396c stem-loop structure was amplified through PCR, and then cloned into the binary vector pZH01, generating the Os-miR396c overexpression gene construct, p35S-Os-miR396c/p35S-hyg. As shown in FIG. 1, panel A and FIG. 22, panel a, Osa-miR396c gene is under the control of Cauliflower Mosaic Virus (CaMV) 35S promoter and linked to the hygromycin resistance gene, Hyg, driven by CaMV 35S promoter. To select positive transgenic plants containing miR396c overexpression constructs, Hyg gene was amplified with genomic DNA of regenerated plants after transformation. FIG. 1, panel B and FIG. 22, panel b showed the examples of positive transgenic events. Through PCR analysis, we obtained 33 transgenic lines in total. All transgenics have smaller leaf area (shorter and finer) than WT plants. Among different events, TG-2 and TG-6 have extremely fine leaves. To determine individual transgenic events and copy number of pri-miR396c (pri-mi396c), southern blot analysis was conducted. FIG. 1, panel C and FIG. 22, panel c show examples of different transgenic events. To detect whether the primary sequence of Os-miR396c (pri-mi396c) had been integrated into the host genome at RNA level, we conducted semi-quantitative Reverse transcription (RT) PCR analysis to compare the expression levels of pri-miR396c between WT control and six transgenic lines. The result indicated that transcripts of pri-miR396c were significantly higher in three transgenic lines than in WT controls (FIG. 1, panel D). Additional transgenic lines with significantly higher levels of transcripts of pri-miR396c are shown in FIG. 22, panel d. To determine whether pri-miR396c can process into miR396c mature sequence successfully, quantitative stem-loop RT-PCR analysis was carried out. The expression levels of mature Os-miR396c in three transgenic lines, TG2, TG7 and TG32, were significantly high in comparison with WT plants (FIG. 1, panel E), as well as in TG14 (FIG. 22, panel e), suggesting that the primary sequence of Os-miR396c from rice can be processed properly in creeping bentgrass.

Transgenic Turfgrass Overexpressing miR396c Leads to Altered Plant Development

Studies were conducted to analyze the developmental differences between WT plants and eight transgenic events initiating from single tiller in cone-tainers filled with pure sand.

Figure 2:
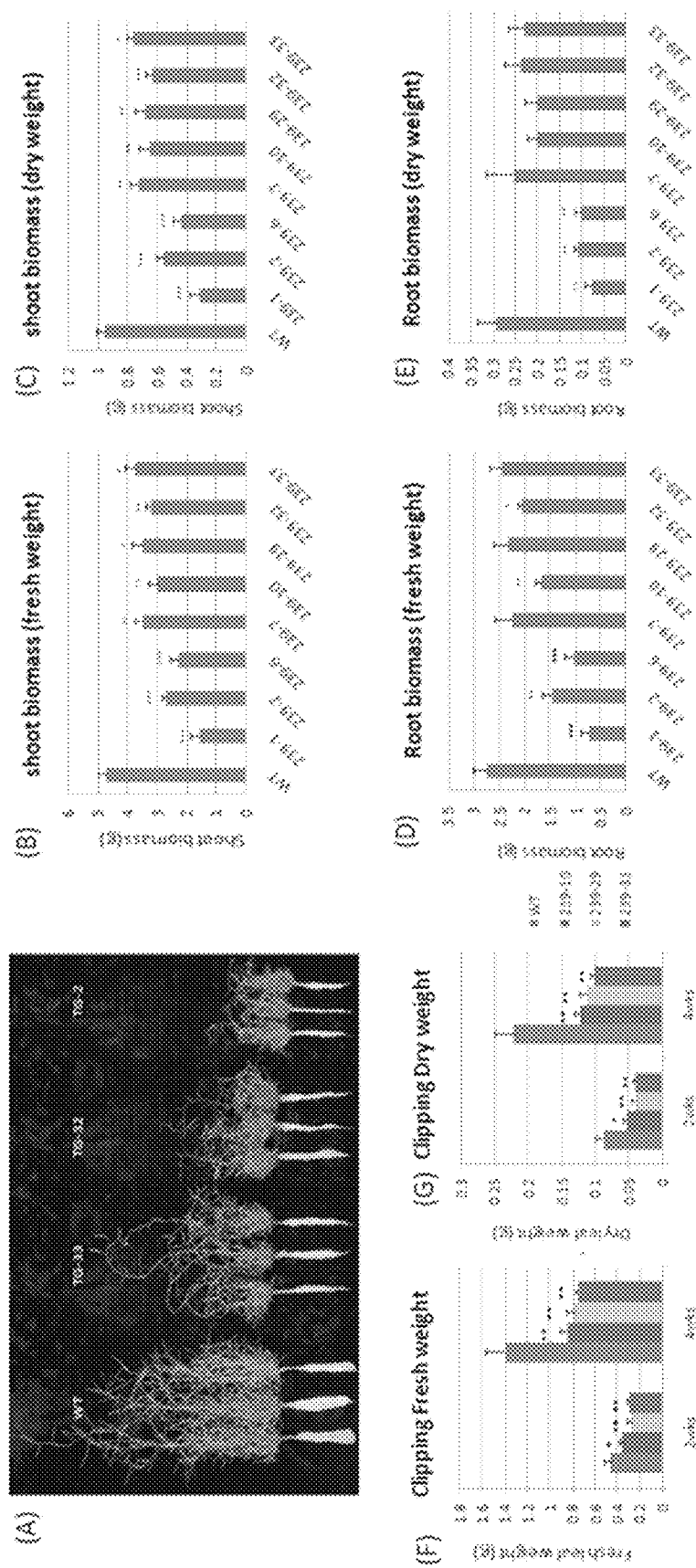
FIG. 2. Biomass accumulation of WT and transgenic creeping bentgrass plants. (Panel A) Ten-week-old WT and TG plants initiating from a single tiller. (Panel B) Statistical analysis of shoot fresh weight and (Panel C) dry weight between 10-week-old WT plants and eight different transgenic events (n=4). (Panel D) Statistical analysis of root fresh weight and (Panel E) dry weight between 10-week-old WT and transgenic plants (n=4). (Panel F) Fully developed WT and TG plants grown in small cone-tainers were mowed every two weeks with the same height. Clipping fresh weight and (Panel G) dry weight in WT and TG plants were measured every two weeks (n=4). Data are presented as average, and error bars represent ±SE. Asterisk (*, , or *) indicates a significant difference of shoot or root biomass between WT and each transgenic line at P<0.05, 0.01 or 0.001 by Student's t-test.

First, we compared the growth rate between WT and TG plants. FIG. 2, panel A shows that 10-week-old TG plants propagating from single tiller are shorter than WT control. Statistical analysis of root and shoot biomass accumulation indicates that all transgenics display less shoot biomass than WT plants, while having less or similar root biomass in comparison with WT controls (FIG. 2, panels B-E). To further confirm the growth rate difference between WT and three TG plants, we compared their fresh weight and dry weight of clipping collection. Fully developed WT and TG plants starting from the same amount of tillers were trimmed to the same height every two weeks. Clipping was collected and weighed at the end of the $2^{nd}$ and $4^{th}$ weeks. Statistical analysis indicates that transgenics accumulate significantly less clippings than that of WT controls (FIG. 2, panels F-G), which further confirms the growth rate result described above.

Figure 3:
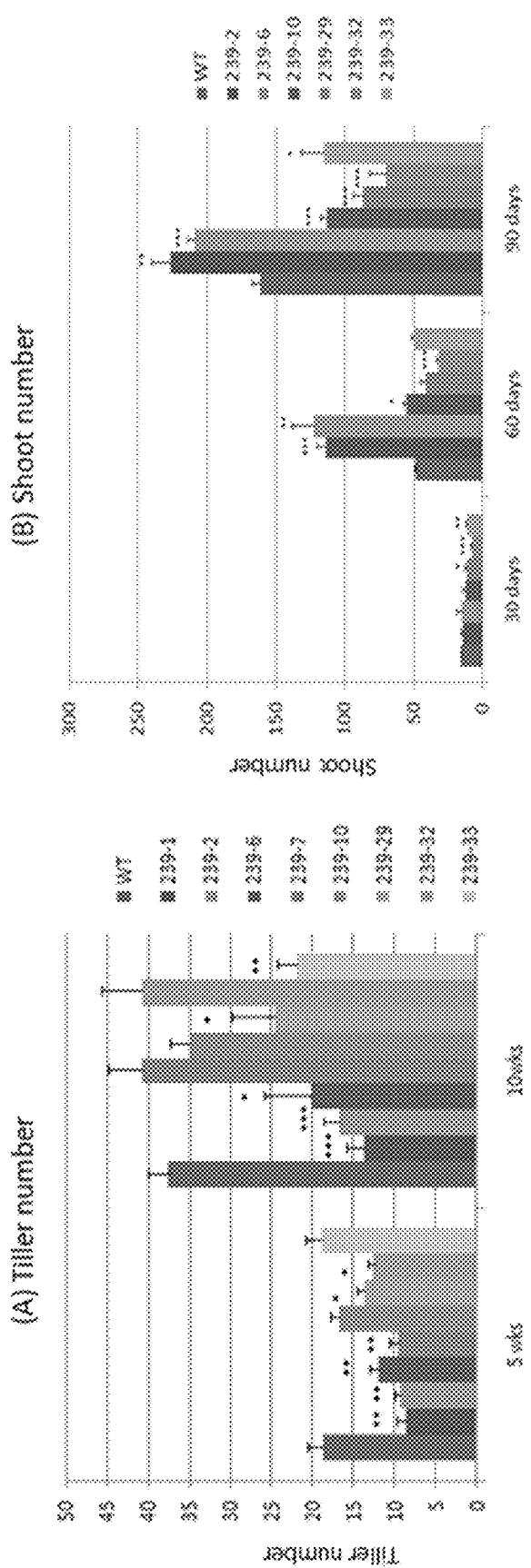
FIG. 3. Tillering of WT and transgenic creeping bentgrass plants. (Panel A) Tiller number in WT and TG plants at five- and ten-weeks after initiating from a single tiller (n=5). (Panel B) The number of total shoot including both tiller and lateral shoot growing out of each tiller in WT and TG plants at 30-, 60-, and 90-days after initiating from a single tiller (n=5). Data are presented as average, and error bars represent ±SE. Asterisk (*, , or *) indicates a significant difference of shoot or root biomass between WT and each transgenic line at P<0.05, 0.01 or 0.001 by Student's t-test.

Next, the difference of tillering was evaluated between WT and TG plants initiating from a single tiller (FIGS. 3 and 24). The number of tillers coming out of a crown was counted at both five- and ten-weeks. FIG. 3, panel A shows that TG-1, 2, 6, 29, and 33 plants have significantly less tiller number than that of controls, while TG-7, 10, and 32 have similar amount of tillers compared to that of WT at later developmental stage of ten weeks. In addition, the number of total shoots coming out of a crown as well as all internodes was counted at 30-, 60- and 90-day time points. At the later developmental stage (90-day), TG-10, 29, 32, 33 have less total shoots than WT plants, while TG-2 and TG-6 plants have significantly more total shoots than WT plants (FIG. 3, panel B), suggesting that transgenics with extremely fine leaves have more shoots coming out of internodes than that of WT controls.

Figure 4:
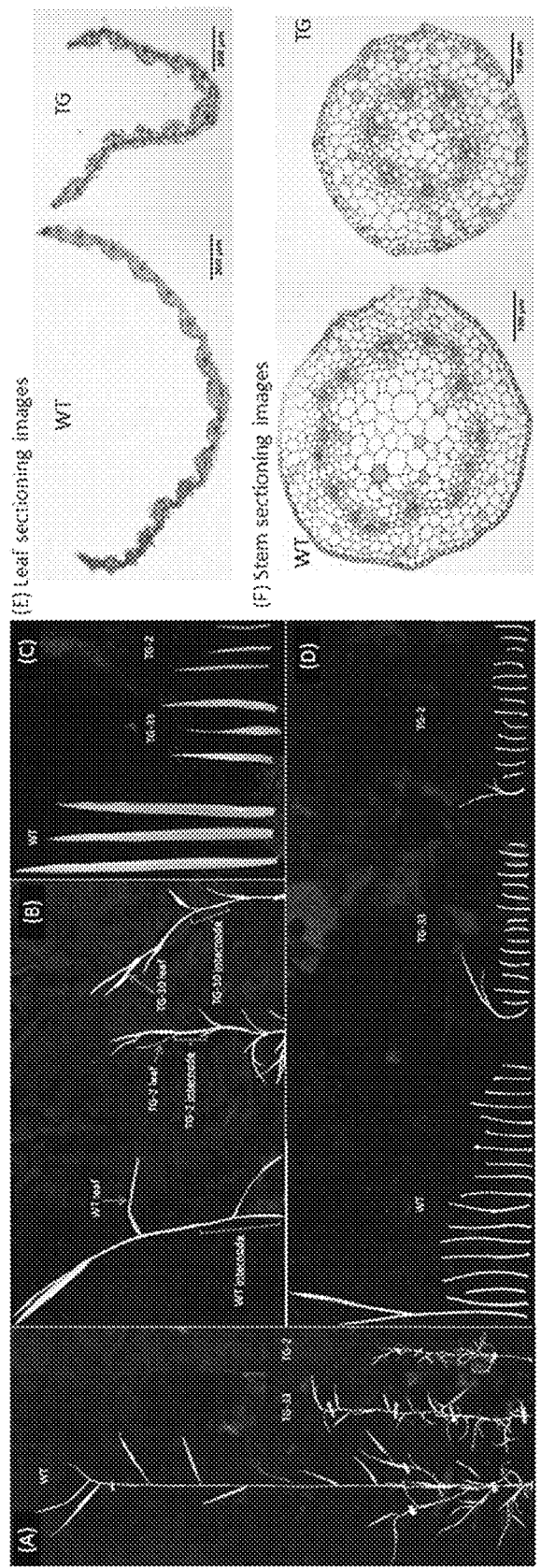
FIG. 4. Morphology change in transgenic turfgrass overexpressing Os-miR396c. (Panel A) The longest tiller of WT and two transgenic lines initiating from single tiller for ten weeks. (Panel B) Transgenic plants exhibit shorter internodes and smaller leaves in comparison to WT control. (Panel C) A closer look of the top first fully unfold leaves of WT and transgenic plants. (Panel D) All internodes of the longest tiller from (Panel A) were sliced from top to bottom and arranged from left to right. (Panel E) Sectioning image of representative WT and TG leaves. (Panel F) Sectioning image of representative WT and TG stems.

Morphologically, all transgenics display shorter tiller length than WT plants after 10 weeks growth initiating from a single tiller (FIG. 4, panel A). To investigate what leads to the short tiller length of transgenics, we compared the internode length of WT and TG plants. FIG. 4, panel D shows every internode from the longest representative tiller of WT and TG, suggesting that the shorter tiller length of transgenics is caused by shorter internode length. Besides shorter tiller length, transgenics exhibit shorter leaf width and length, and finer stem than those of WT plants (FIG. 4, panels B-D). To elucidate if reduced cell number, cell size, or a combination of these two parameters leads to smaller leaf and finer stem of transgenic plants, we conducted leaf and stem sections. The sectioning images of leaf and stem indicate that the finer leaf and stem are associated with reduced vein number and vascular bundle number separately (FIG. 4, panels E-F, FIG. 24, panels a-g). Statistical analysis of cell number in leaf and stem between WT and TG plants is useful to understand whether miR396c has the conserved function of reducing cell number in transgenic creeping bentgrass.

Figure 5:
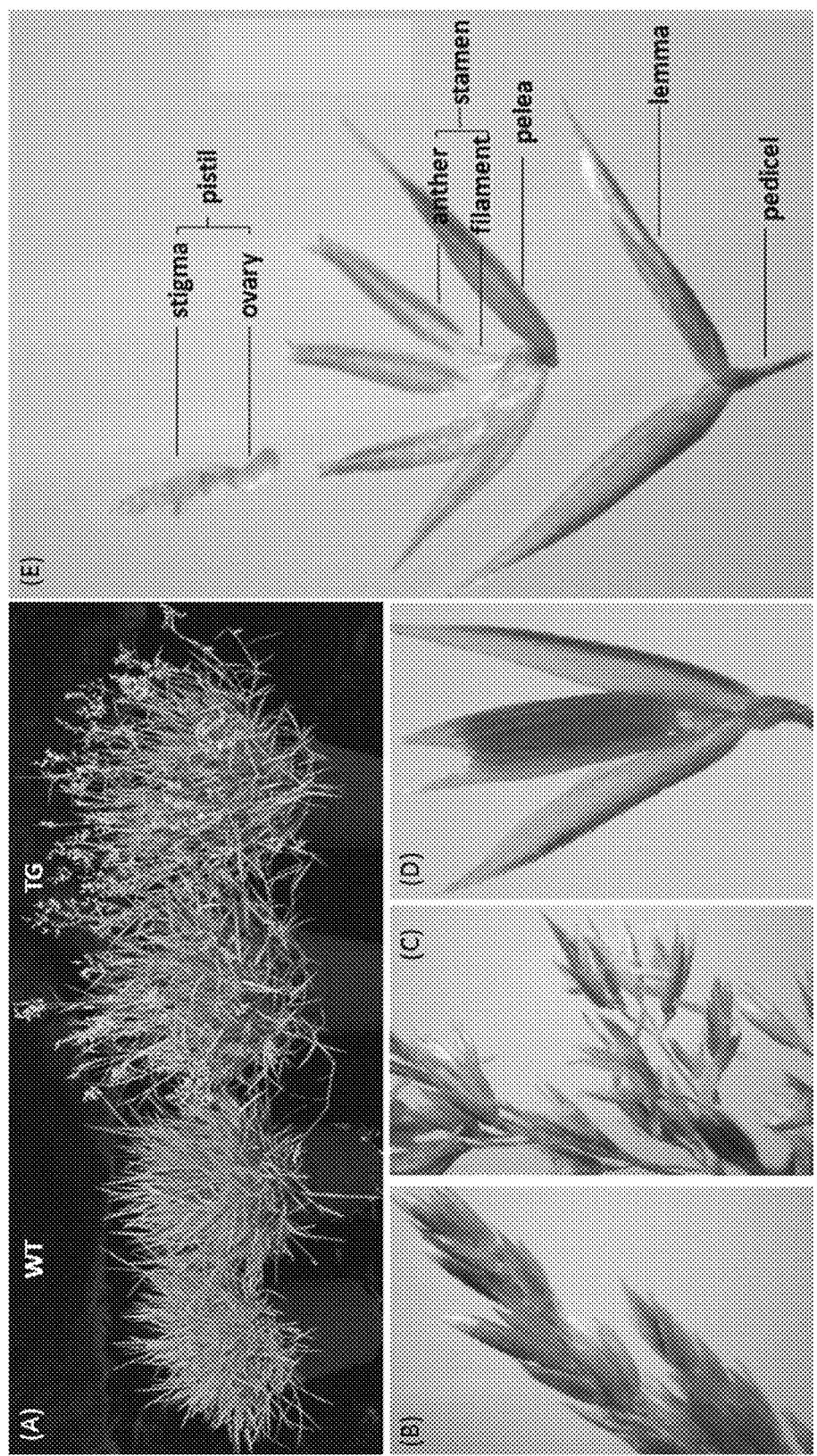
FIG. 5. TG plants flower bypassing vernalization requirement. (Panel A) WT and TG plant growth under long day conditions for four weeks without prolonged cold treatment. (Panel B) and (Panel C) Spikelet of TG plant. (Panel D) Floralet of TG plant. (Panel E) Anatomy of TG creeping bentgrass floralet.

Constitutive Expression of Os-miR396c in Creeping Bentgrass Bypasses Vernalization Requirement for Flowering WT creeping bentgrass requires at least 15 weeks of vernalization and long day conditions afterwards to induce flowering. It is interesting that all transgenic events can flower under long day induction only without vernalization requirement (FIG. 5, panels A-D). Investigation of the relationship between photoperiod length and flowering induction time shows that under 24h, 16h, and 13h light conditions, transgenic plants overexpressing Os-miR396c were flowering at the third and fourth week, and never flowering separately. Structurally, the transgenic floralet contains a pistil including two stigmas and an ovary, three stamens including anthers and filaments, a pelea, a lemma, and a pedicel as WT creeping bentgrass (FIG. 5, panel E).

MiR396c is Involved in Floral Organ Development

Figure 6:
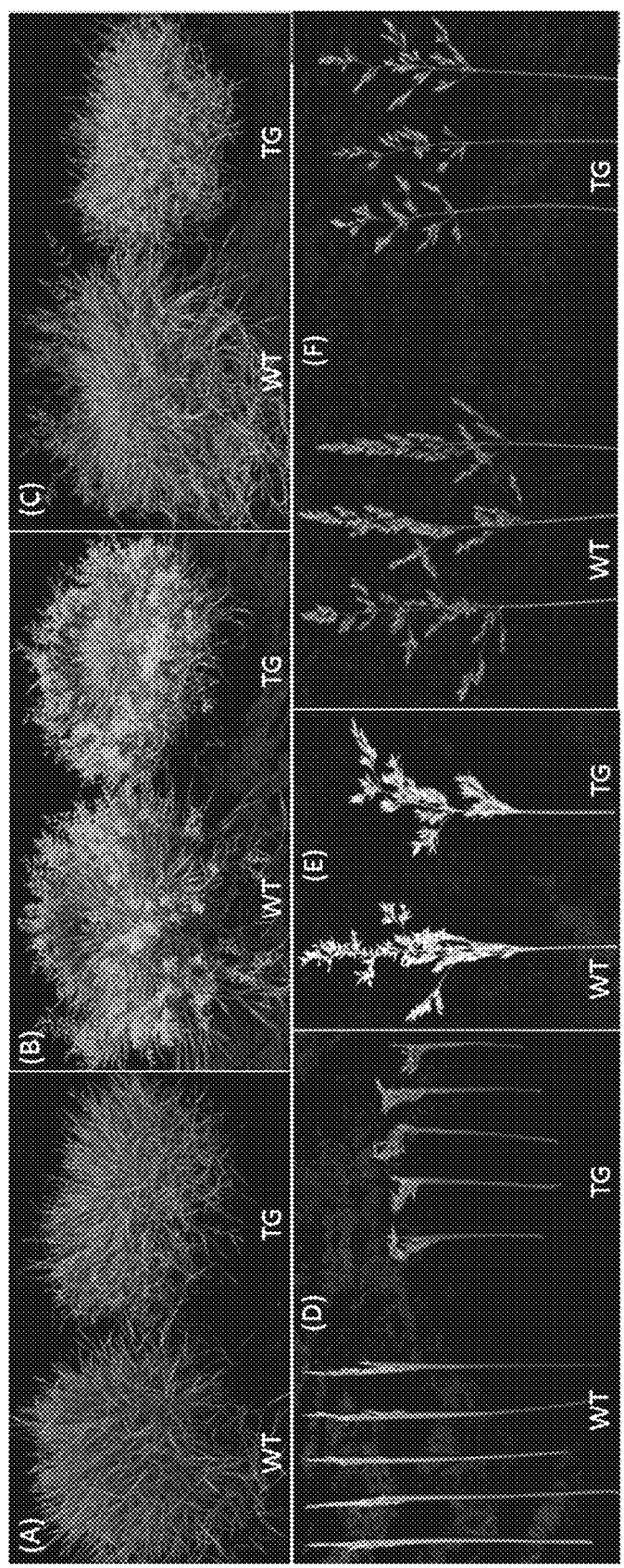
FIG. 6. Morphology change of TG spikes. (Panel A) WT and TG plants flower after 17-week vernalization and four-week long-day induction. (Panel B) Flowers of WT and TG after vernalization and six weeks of long-day induction. (Panel C) Flowers of WT and TG after vernalization and eight weeks of long-day induction. (Panel D) Close up of WT and TG spikes after four weeks of long-day induction. (Panel E) Close up of WT and TG spikes after six weeks of long day induction. (Panel F) Close up of WT and TG spikes after eight weeks of long-day induction.

To compare the flower development between WT and TG plants, both of them underwent a 17-week 5° C. cold treatment and short day conditions, followed by 25° C./17° C. (light/dark) long day conditions to induce flowering. WT and TG flowers were photographed at the $4^{th}$, $6^{th}$, and $8^{th}$ week after transferring to the 25° C./17° C. (light/dark) long day conditions. FIG. 6, panels A-D show that both WT and TG are in the initiation stage of flowering at the $4^{th}$ week, while spikes of transgenic plant are curly in comparison to that of controls. At the 6th week of long day induction, both WT and TG plants are in the anthesis stage. Transgenic spike is still curly compared to that of WT control (FIG. 6, panels B, E). Two weeks later, WT plants showed reddish to purple panicles, while that of transgenics still keep green (FIG. 6, panels C, F).

Figure 7:
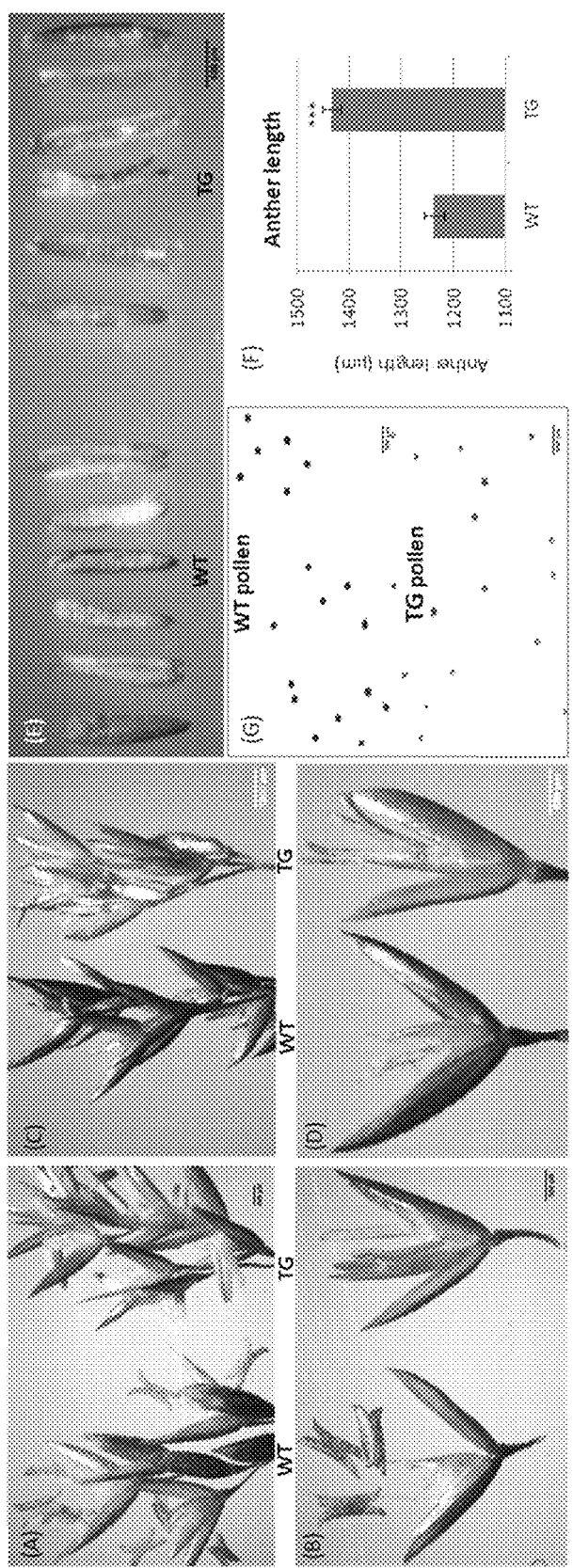
FIG. 7. Morphology change of TG Floralet. (Panel A) Floralets of WT and TG plants after five weeks of long-day induction. (Panel B) Close up of (Panel A). (Panel C) Floralets of WT and TG plants after eight weeks of long-day induction. (Panel D) Close up of (Panel C). (Panel E) Representative WT and TG anthers one day before dehiscence. (Panel F) Statistical analysis of anther length between WT and TG (n=6). Data are presented as average, and error bars represent ±SE. Asterisk (***) indicates a significant difference of shoot or root biomass between WT and each transgenic line at P<0.001 by Student's t-test. (Panel G) WT and TG pollen staining with $I_2KI$ for starch.

During the anthesis stage, we compared the floralet difference of WT and TG plants under a microscope. At the 5$^{th}$ and the 8$^{th}$ week after long day induction, transgenic plants exhibit a defect in anther dehiscence, and their anthers are hard to stick out completely (FIG. 7, panels A-D). In addition to the defect function of the transgenic anther, the length of anthers between WT and TG plants are different (FIG. 7, panel E). Statistical analysis indicates that TG anthers are significantly longer than that of WT controls (FIG. 7, panel F). Further, we examined the pollen fertility of transgenics. Since transgenic pollens cannot be released, we opened the fully developed WT and TG anthers one day before the dehiscence manually and stained pollens with I$_2$KI. FIG. 7, panel G shows that WT pollens are round and can be stained in dark color, while the transgenic plant has smaller pollen size than WT and cannot be stained successfully, indicating that pollens of transgenic plants are sterile.

Figure 8:
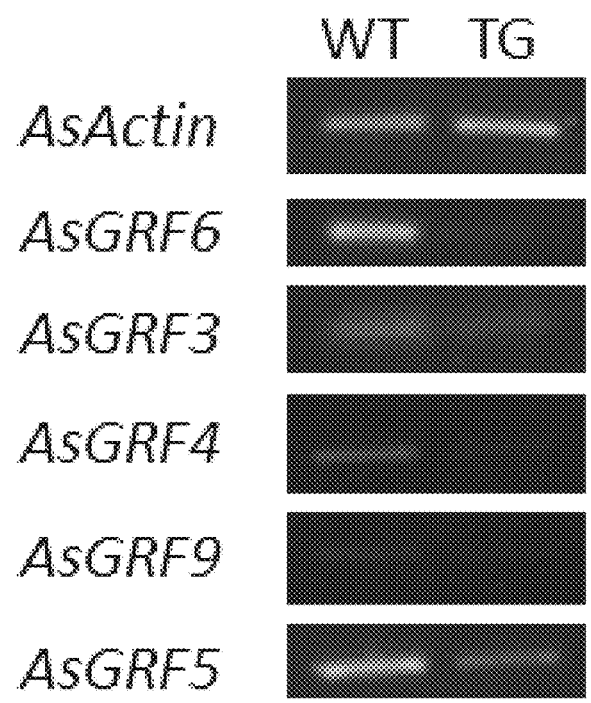
FIG. 8. RT-PCR analysis to identify creeping bentgrass miR396 target genes and their expression.

Identification and Expression Analysis of the Putative miR396 Target Genes in Transgenic Creeping Bentgrass In order to examine if the expression of miR396 targets, GRF genes, are impacted in transgenic creeping bentgrass plants, partial sequences of GRF orthologues in creeping bentgrass have been amplified. Five GRF genes show reduced expression level in transgenics compared to WT controls (FIG. 8).

Identification of miR396-Mediated Key Genes in Vernalization Pathway Via RT-PCR

Figure 9:
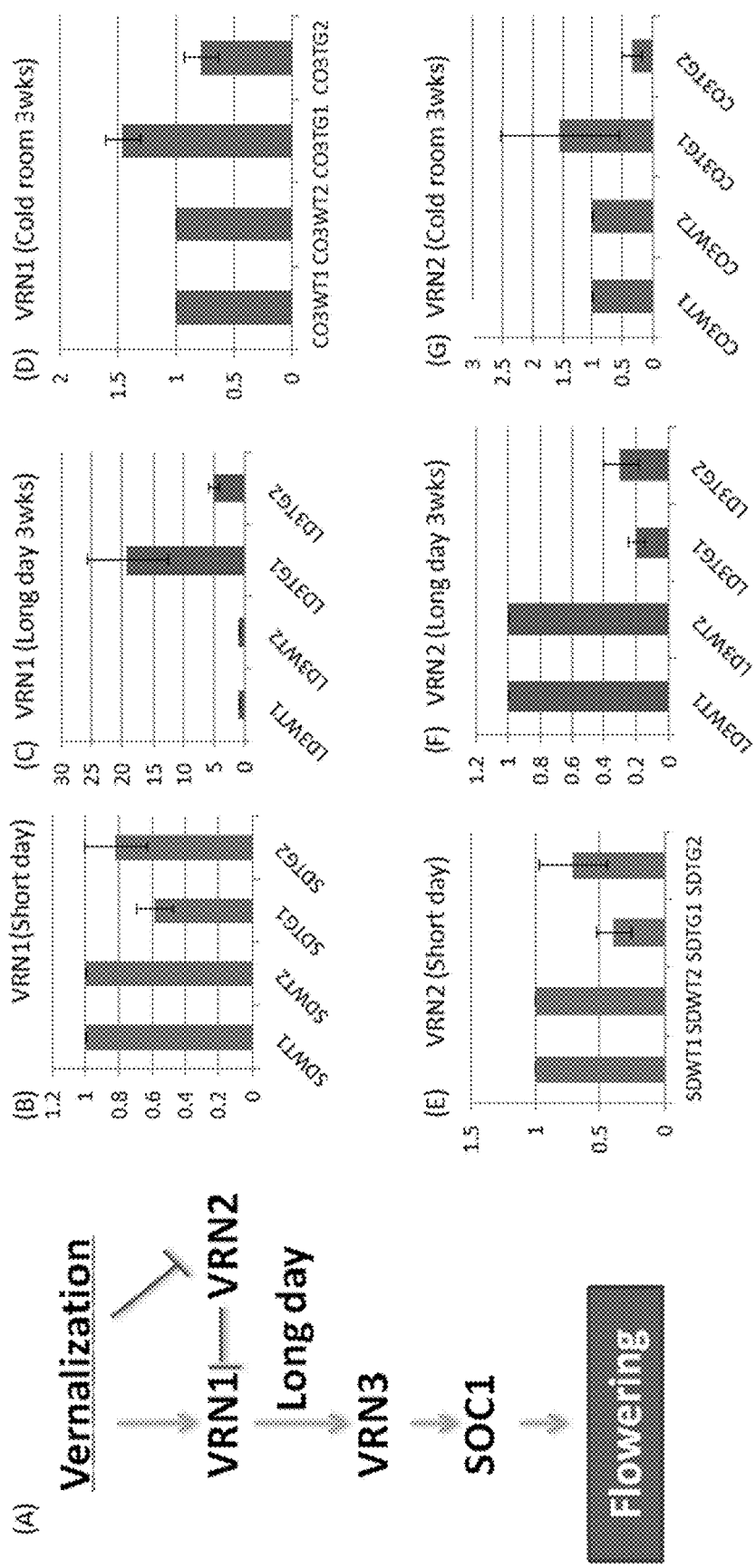
FIG. 9. Expression profile of vernalization pathway genes in WT and TG plants. (Panel A) Vernalization pathway in monocot crop species. VRN1 expression level of WT and TG plants under short day (Panel B), three-week long day (Panel C), and three-week cold treatment (Panel D). VRN2 expression level of WT and TG plants under short day (Panel E), three-week long day (Panel F), and three-week cold treatment (Panel G).

The molecular mechanism of vernalization pathway in both dicot and monocot plant species have gradually been uncovered. In *Arabidopsis*, the flowering activator FLOWERING LOCUS T (FT) is induced by long day (LD) conditions. FT protein is produced in the vascular tissue of leaves, and then transports to shoot apical meristem (SAM) along phloem to interact with FLOWERING LOCUS D (FD), which is produced in vegetative stages only in SAM. The interaction between FD and FT promotes the transition from vegetative to reproductive phase to induce APETALA1 (AP1) and FRUITFULL (FUL), both of which are floral meristem identity genes. Vernalization represses FLC to release the inhibition on FT. CO induces FT and SOC1 under LD conditions. In wheat, vernalization induces the expression level of VRN1, which represses the level of VRN2 and up-regulates FT ortholog VRN3, which is repressed by VRN2. Without repression, VRN3 then promotes VRN1 expression and floral development (FIG. 9, panel A). However, there is no information about vernalization signaling transduction in perennial turfgrass, for example, creeping bentgrass. To understand how transgenic creeping bentgrass overexpressing Os-miR396c overcomes the vernalization requirement, we examined the expression levels of all the key genes in the vernalization pathway of monocot plants. Real-time RT-PCR analysis indicates that while there is no significant difference between WT and TG VRN1 transcript level under short day and three-week cold treatment, VRN1 is strongly induced in long day three-week conditions (FIG. 9, panels B-D). VRN2 has a similar expression level between WT and TG plants under short day and three-week cold treatment. However, its level is decreased significantly under long day three-week induction (FIG. 9, panels E-G). Then, both up-regulated VRN1 and down-regulated VRN2 promote plant flowering. Previous study indicates that cold induces the expression level of VRN1 and represses the expression level of VRN2. Interestingly, our results indicates that constitutive expression of miR396c leads to the same regulation on the expression level of VRN1 and VRN2 as cold treatment, suggesting that overexpression of miR396c could substitute the prolonged cold induction.

TG Plants Show Enhanced Cold Stress Resistance

Figure 10:
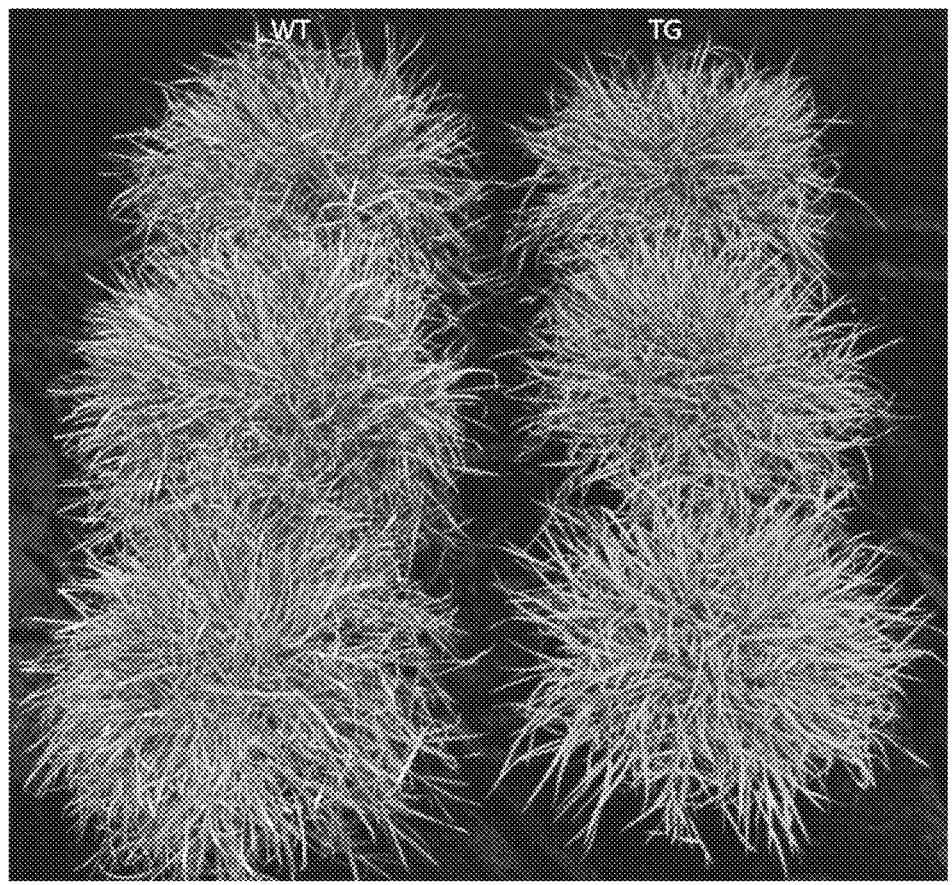
FIG. 10. 17-week cold treatment for WT and TG creeping bentgrass under short day conditions.

We applied cold treatment to WT controls and TG plants overexpressing Os-miR396c for 17 weeks. The results show that transgenics are greener and have less wilting leaves than that of WT controls (FIG. 10).

Cloning of the miR396c Gene and Plasmid Construction

The full length of Os-miR396c gene (GenBank® Accession No. AK062523.1) containing the pre-miR396c stem-loop structure was isolated by PCR from rice (*Oryza sativa*) cDNA. The Os-miR396c gene forward and reverse primer set was 5'-<u>TCTAGA</u>TTTT AACCCATCCAATGCCC-3' (SEQ ID NO:26) containing an XbaI recognition site and 5'-<u>GTCGAC</u>CTCTCTCTCTCTCTGCCTG-3' (SEQ ID NO:27) containing a SalI recognition site. PCR products were cloned into the binary vector pZH01, generating the Os-miR396c overexpression gene construct, p35S-Os-miR396c/p35S-hyg. The construct contains the cauliflower mosaic virus 35S (CaMV 35S) promoter driving Os-miR396c, which is linked to the CaMV 35S promoter driving the hyg gene for hygromycin resistance as a selectable marker. For subsequent plant transformation, the construct was transferred into *Agrobacterium tumefaciens* strain LBA4404.

Plant Materials and Transformation

Creeping bentgrass (*Agrostis stolonifera* L.) cultivar 'Penn A-4' (supplied by HybriGene) was used for plant transformation. Transgenic plants constitutively expressing Os-miR396c were produced via *Agrobacterium*-mediated transformation of embryonic callus induced from mature seeds.

Plant Propagation, Maintenance, and Abiotic Stress Treatments

The regenerated transgenic plants overexpressing Os-miR396c were transferred in commercial nutrient-rich soil (3-B Mix, Fafard) and initially maintained in the greenhouse with wild type (WT) controls at 27° C. during the light and 25° C. during the dark under long day conditions (16 h of light/8 h of dark).

To observe the developmental differences and to conduct abiotic stress tests, transgenics and WT plants were vegetatively propagated from tillers and grown in cone-tainers (4.0×20.3 cm, Dillen Products), small pots (9.8×7 cm, Dillen Products), middle pots (15×10.5 cm, Dillen Products), or big pots (33×44.7 cm, Dillen Products) using silica sand. The plants were maintained in the growth room in a 13-h-light/11-h-dark photoperiod at 350-450 µmol m$^{-2}$ s$^{-1}$ light intensity provided by AgroSun Gold 1000 W sodium/halide lamps (Maryland Hydroponics). Temperature and humidity were maintained at 25° C./17° C. (light/dark), and 30%/60% (light/dark), respectively. Plants were watered every other day with 0.2 g/L 20:10:20 water-soluble fertilizer (Peat-Lite Special; The Scotts Company) and mowed every week to achieve uniform growth.

Plant DNA, RNA Isolation and Expression Analysis

Plant genomic DNA was extracted from 30 mg of fresh leaves in 1.5 mL microcentrifuge tube using 2×cetyltrimethyl ammonium bromide (CTAB) buffer following Luo's protocol. Plant total RNA was isolated from 100 mg of fresh leaves using Trizol reagent (Invitrogen) following the manufacturer's protocol. First strand cDNA was synthesized from 2 ug of RNA with SuperScript III Reverse Transcriptase (Invitrogen) and oligo(dT) or gene specific primers. The semi-quantitative RT-PCR was conducted on 24 to 30 cycles based on its exponential phase. PCR products were separated by using 1.5% agarose gel electrophoresis and visualized as well as photographed with GelDoc-It (An Analytik Jena Company).

Real-time RT-PCR was performed with 12.54, of iQ SYBR-Green Supermix (Bio-Rad Laboratories) per 254, reaction system. The green fluorescence signal was monitored on Bio-Rad iQ5 real-time detection system by using iQ5 Optical System Software version 2.0 (Bio-Rad Laboratories). AsACT1 (JX644005) and AsUBQ5 (JX570760) were used as endogenous controls. The relative changes of gene expression were calculated based on $2^{-\Delta\Delta C_T}$ method, in which $\Delta\Delta C_T=[(C_T \text{ gene of interest}-C_T \text{ reference gene}) \text{ control sample}-(C_T \text{ gene of interest}-C_T \text{ reference gene}) \text{ treated sample}]$.

Stem-loop RT-qPCR was performed. The miR396c stem-loop RT primer and PCR forward primer are 5'-GTCTC-CTCTGGTGCAGGGTCCGAGGTATTCGCACCA-GAGGA GACAAGTTC-3' (SEQ ID NO:28) and 5'-TGGTGCAGGGTCCGAGGTATT-3' (SEQ ID NO:29), separately.

Plant Histology Analysis

WT and transgenic plants initiating from the same amount of tillers were propagated in the same middle pot (15×10.5 cm, Dillen Products). Four weeks later, from the top of tillers, the second and third internodes and fully expanded leaves were collected and immersed in formalin-acetic-alcohol fixative, which contains 50% of 100% ethanol, 10% of 37% formaldehyde solution and 5% glacial acetic acid for 48 hours at room temperature. After fixation, plant tissues were dehydrated with a series of graded ethanol from 70% to 100%, followed by paraffin wax infiltration. Tissues were then embedded in paraffin blocks. When paraffin solidified, blocks were ready to process section using the rotary microtome (RM 2165, Leica). Sections were stained using toluidine blue and observed under stereo microscope (MEIJI EM-5). Photographs were taken using 35 mm SLR camera body (Canon) connected to the microscope. Scale bars were added to photographs using ImageJ.

Example 2. MiR396 is Involved in Plant Response to Vernalization

To investigate the role of miR396 in flower development in perennial species, we generated transgenic creeping bentgrass (*Agrostis stoloniftra* L.) overexpressing a rice miR396 gene, Os-miR396c. In this study, transgenic (TG) plants altered flower development, including anther dehiscence defects and pollen sterility. Interestingly, TG plants overcome vernalization requirement for flowering. To our knowledge, this is the first time to report that miR396 is involved in flowering time control or vernalization pathway. Four GRF genes, which showed repressed expression in TG plants, are identified as potential targets of miR396 in creeping bentgrass. To study the molecular mechanism of miR396-mediated flowering time control, expression profiles of miR396 and its targets were analyzed in the conditions of exposure of plants to SD followed by the transfer to LD (referred hereafter as SD-LD) and exposure of SD grown plants to prolonged cold followed by LD (referred hereafter as SD-cold-LD). In addition, the expression patterns of the closest orthologs of VRN1, VRN2 and FT are characterized in WT and transgenic creeping bentgrass in SD-LD and SD-cold-LD conditions. VRN1 and VRN2 show similar expression patterns as in wheat and barley during vernalization followed by LD conditions. Without vernalization, VRN1 and VRN2 in TG plants show induced and repressed levels respectively under SD-LD conditions compared to WT controls. Further, a global view on impacts of miR396 in reproductive development and vernalization was elucidated through RNA-seq analysis. Our results point to the great potential of controlling flowering time through manipulating miR396 to contribute to the agriculture productivity.

Overexpression of miR396c Bypasses Vernalization Requirement

Figure 11:
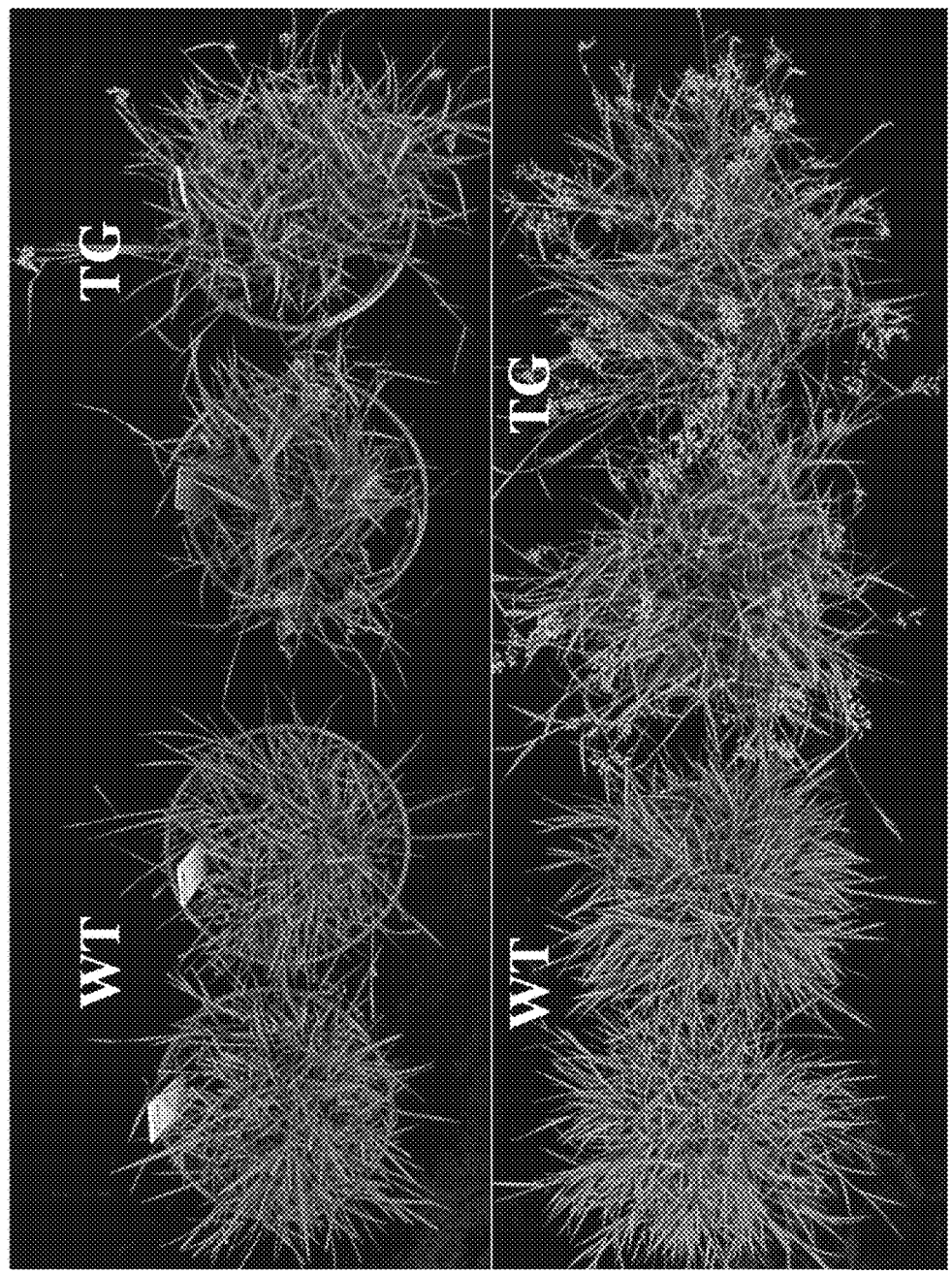
FIG. 11. Osa-miR396c transgenic creeping bentgrass flowers without vernalization. Performance of WT and TG plants under 16 h photoperiod induction for four and six weeks without vernalization.
Figure 12:
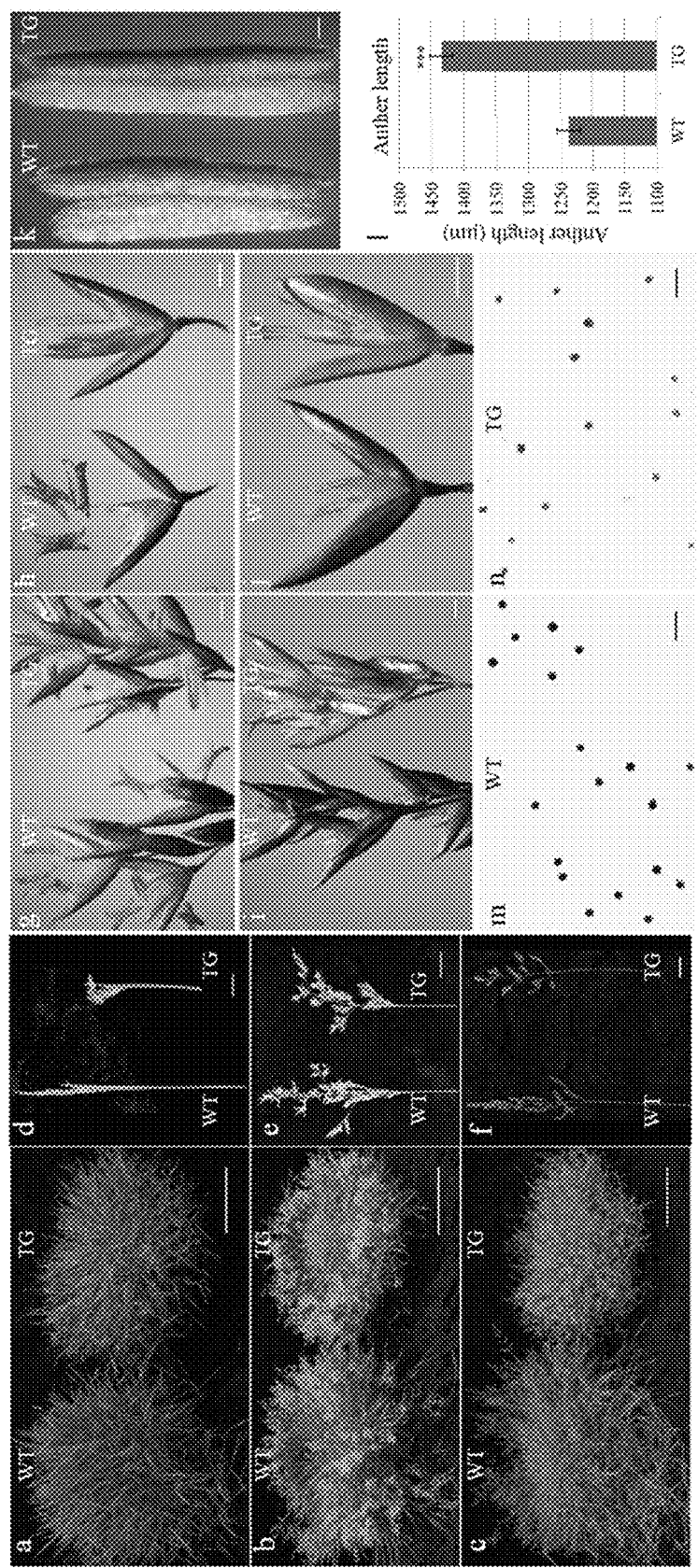
FIG. 12. Flower development between WT and TG plants. Vernalized WT and TG plants under LD conditions for (panel a) four weeks, (panel b) six weeks, and (panel c) eight weeks. Scale bar, 10 cm. WT and TG spikelets after LD induction for (panel d) four weeks, (panel e) six weeks, and (panel f) eight weeks. Scale bar, 1 cm. Close up of WT and TG spikelets at (panel g) six weeks and (panel i) eight weeks after LD induction. Scale bar, 500 μm. Representative WT and TG floralets at (panel h) six weeks and (panel j) eight weeks after LD induction. Scale bar, 500 μm. (panel k) Representative anthers of WT and TG plants. Scale bar, 100 μm. (panel l) Anther lengths of WT & transgenic turfgrass overexpressing os-miR396c were measured at the same stage after flowering. Data are presented as means (n=6), and error bars represent±SE. Asterisks (***) indicate a significant difference between WT and TG anther length at P<0.001 by Student's t-test. (panel m) WT and (panel n) TG pollens were stained with potassium iodide. Scale bar, 100 μm.

Creeping bentgrass is cool season turfgrass which requires a prolonged exposure to the cold of winter for the competence to flower. To investigate the impacts of miR396 on flower development in creeping bentgrass, we need to induce flowering at first. To our knowledge, the length of vernalization period for flowering in creeping bentgrass is unsure. Previous study indicates that colonial bentgrass (*Agrostis capillaris*), which belongs to the same genus as creeping bentgrass, requires 15 weeks of cold treatment (SD, 3-12° C. or LD, 3-6° C.). To evaluate the length of cold requirement to saturate the vernalization response, two replicates of WT and Os-miR396c transgenic creeping bentgrass growth under SD conditions (14-h light, 25° C./10-h dark, 17° C.) were subjected to cold exposure (8-h light/16-h dark, 5° C.) for 0-, 11-, 12-, 13-, 14-, 15-, 16-, 17-, and 18-week followed by LD conditions (16-h light, 25° C./8-h dark, 17° C.). Interestingly, the result indicates that WT plants won't flower in LD conditions until 15-week or longer cold exposure, whereas TG plants flower at all different periods of cold exposure (0-week to 18-week), indicating that TG plants overexpressing Os-miR396c overcome vernalization requirement (FIG. 11). In addition, both vernalized WT controls and TG plants (with or without vernalization) require 4-week of LD (16-h light/8-h dark) induction for inflorescence emergence (FIG. 12, panels a, d). The longer cold treatment (18-week) failed to accelerate flowering in WT plants compared to 15-week cold exposure. Investigation of the relationship between different photoperiods and flowering time shows that at 24-h, 16-h, and 14-h photoperiods, inflorescence emergence was observed in vernalized plants or TG plants without vernalization at the third week, the fourth week, and never flowering, respectively. The result indicates that longer photoperiod leads to more rapid flowering.

Overexpression of miR396c Alters Flower Development

After understanding the flowering requirement for creeping bentgrass, floral organ development between WT and TG plants were compared. WT and TG flowers were photographed at the $4^{th}$, $6^{th}$, and $8^{th}$ week of LD conditions following 15-week vernalization. During florescence emergence (4-week in LD) and anthesis (6-week in LD), the spikes of transgenic plant are curly in comparison with WT controls (FIG. 12, panels a, b, d, e). Two weeks later, WT plants display reddish to purple panicles, while transgenics still keep green (FIG. 12, panels c, f).

During anthesis, the floralets of WT and TG plants were compared via microscopic analysis. At the $6^{th}$ and the $8^{th}$ week of LD conditions, transgenic plants exhibit defects in fully sticking out anther and dehiscence (FIG. 12, panels g-j). In addition, statistical analysis indicates that transgenic anthers are significantly longer than that of WT controls (FIG. 12, panels k, l). Further, we examined the pollen fertility of WT controls and transgenics. Since pollens cannot be released by TG plants, we manually opened the fully developed WT and TG anthers before dehiscence and stained pollens with 2% (w/v) potassium iodide. WT pollens are circular and darkly stained (FIG. 12, panel n), whereas transgenic pollens have varied shapes and are lightly stained (FIG. 12, panel n), which indicates that pollens of transgenic plants are sterile.

MiR396c Impacts Floral Organ Development Through Targeting GRFs

Increasing evidence indicates that miR396 play an important role in floral organ development by post-transcriptionally repressing the expression of GRFs. In *Arabidopsis*, seven of nine GRF family members have miR396 target sites; while 10 of 12 GRFs in rice have miR396 target sites. In creeping bentgrass, we identified four GRF orthologs of rice with miR396 binding sites, which are AsGRF3, AsGRF4, AsGRF5, and AsGRF6 (not shown). Their expression levels are repressed in TG plants compare to WT controls (not shown). Therefore, we conclude that the altered flower development results from the repressed GRFs in TG plants.

MiR396 is Induced in LD Photoperiod and Vernalization

Figure 13:
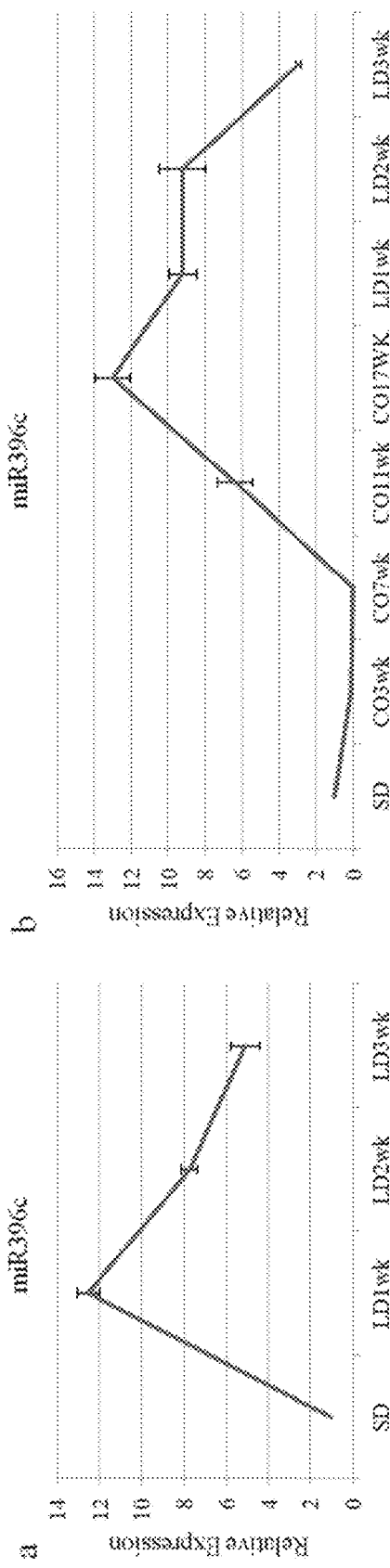
FIG. 13. Expression profiles of miR396c under SD-LD, and SD-cold-LD conditions. (panel a) Stem-loop RT-qPCR analysis of miR396 expression in WT plants under SD and LD 1-, 2-, 3-week without vernalization. (panel b) Stem-loop RT-qPCR analysis of miR396 expression in WT plants under SD, cold 17-week, and LD conditions. The relative changes in gene expression were calculated based on $2^{-\Delta\Delta CT}$ method. AsUBQ was used as an endogenous control. Data are presented as means of three technical replicates, and error bars represent ±SE.

To detect how miR396 is regulated in different photoperiods and temperatures, we analyzed the expression levels of miR396 in WT plants under SD-LD and SD-cold-LD conditions. When switching the WT plants from SD (14-h photoperiod) to LD (16-h photoperiod), the abundance of miR396 was elevated dramatically at LD one-week, and then gradually decreased but still kept high compared to SD conditions (FIG. 13, panel a); when switching the WT plants from SD to cold conditions, levels of miR396 were decreased at 3- and 7-week, and then significantly induced at 11- and 17-week cold conditions (FIG. 13, panel b); when shifting to LD (25° C. at daytime/17° C. at night), levels of miR396 were gradually declined but were still significantly high compared to SD conditions (FIG. 13, panel b). The result suggests that miR396 is response to the environmental cues including LD light regime and low temperature, both of which upregulate the levels of miR396.

Identification of VRN1, VRN2, and VRN3 Orthologs in Creeping Bentgrass

In winter cereals, VRN1, VRN2, and VRN3 are key genes in the vernalization process for accelerating flowering. Currently, the vernalization response at molecular level is elusive in creeping bentgrass. To study if it is also regulated by VRNs in this cool-season perennial turfgrass as in wheat, barley, or *Brachypodium*, we cloned the full length orthologs of VRN1, VRN2 and VRN3/FT from winter cereals by 5' and 3' RACE (Rapid Amplification of cDNA Ends).

Figure 14:
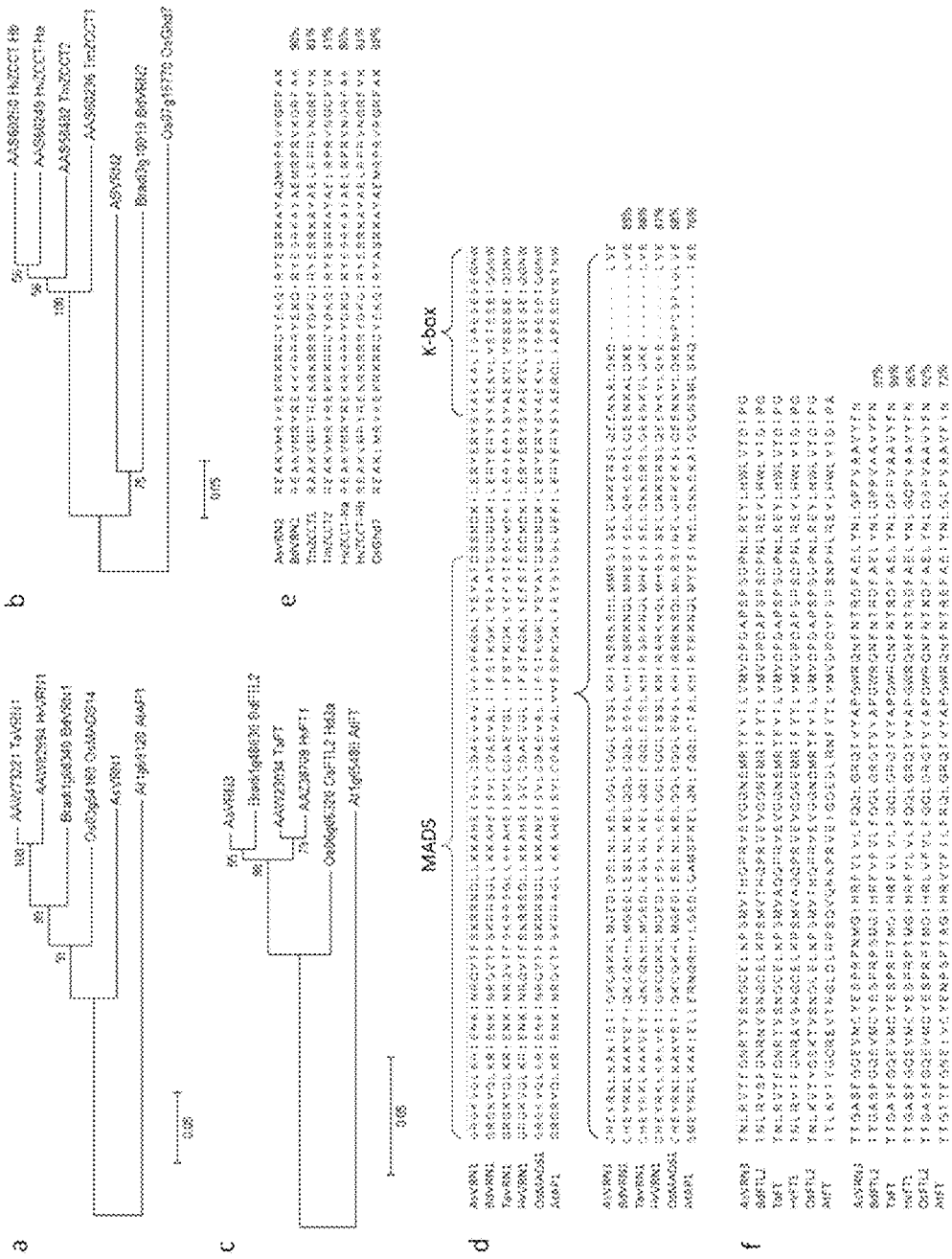
FIG. 14. Phylogenetic analysis of VRN1, VRN2, and VRN3 proteins and sequence alignment of their conserved domains. Phylogenetic trees of (panel a) VRN1, (panel b)

AsVRN1 encodes a 262 aa protein, which shares a high identity with its orthologs from wheat (72%), barley (68%), *Brachypodium* (73%), rice (72%), and *Arabidopsis* (68%). A neighbor-joining phylogenetic analysis of full length amino acid sequences from these species divides VRN1 orthologs into monocot clade and dicot clade (FIG. 14, panel a). AsVRN1 is placed in the monocot clade as shown in FIG. 14, panel a. VRN1 from grass is related to APETALA1 (AP1)/CAULIFLOWER (CAL)/FRUITFUL (FUL), a subgroup of MADS-box transcription factors controlling the initiation of the vegetative to reproductive transition. Sequence alignment revealed conserved type-II MADS domain and K-box (FIG. 14, panel d), which are characteristic of AP1/CAL/FUL clade. The high sequence similarity of the conserved MADS domain and K-box between AsVRN1 and each VRN1 ortholog suggests that AsVRN1 is the VRN1 putative ortholog in creeping bentgrass (FIG. 14, panel d).

The flowering repressor VRN2 in cereal behaves similarly to the MADS-box gene FLC in *Arabidopsis*, while they are unrelated. VRN2 orthologs from wheat (TmZCCT1 and TmZCCT2), barley (HvZCCT-Ha and HvZCCT-Hb), *Brachypodium* (BdVRN2), and rice (OsGhd7) are members of a CONSTANS-like superfamily containing a conserved CCT domain. Currently, the ortholog of VRN2 in *Arabidopsis* is unknown. In creeping bentgrass, we successfully cloned the full length of AsVRN2, which encodes a 213 aa protein Amino acid sequence alignment among AsVRN2 and other VRN2 orthologs indicates that AsVRN2 carries a CCT domain (FIG. 14, panel e). Phylogenetic analysis of the complete protein sequences of VRN2 orthologs placed AsVRN2 and BdVRN2 into the same clade, suggesting that AsVRN2 is the VRN2 putative ortholog.

The flowering promoter VRN3IFT is a member of a phosphatidylethanolamine-binding protein (PEBP) gene family. VRN3 cloned in creeping bentgrass encodes a 177 aa protein Amino acid sequence alignment among VRN3/FT orthologs shows that AsVRN3 carries a conserved PEBP domain with the length of 139 aa (FIG. 14, panel f). A phylogenetic tree was built with the complete amino acid sequence of VRN3/FT from creeping bentgrass, wheat, barley, *Brachypodium*, rice, and *Arabidopsis*. As FIG. 14, panel c shows, VRN3/FT from the grass subfamily Pooideae are grouped into one clade, while *Brachypodium* ortholog (BdFTL2) and AsVRN3 reside in the same subclade, suggesting that AsVRN3 is in fact a VRN3IFT ortholog in creeping bentgrass.

Effects of Vernalization and Different Photoperiod Regimes on VRNs in WT and TG Creeping Bentgrass After cloning VRNs in creeping bentgrass, we seek to answer several questions. How are VRNs regulated in creeping bentgrass when exposing to prolonged cold and different light regimes? Do VRNs have the similar responses as in wheat, barley, or *Brachypodium*? What is the impact of miR396 on VRNs? What causes the elimination of vernalization requirement in TG plants? To answer these questions, we compared the expression profiles of VRN1, VRN2, and VRN3 in SD-LD and SD-cold-LD conditions in WT and TG creeping bentgrass.

Without vernalization, levels of AsVRN1 in WT plants are low under SD, and dramatically upregulated when shifting to LD at first two weeks, then decreased at LD 3-week but remain elevated compared to SD (FIG. 15, panel a, c), which is in consistent with the expression profile of VRN1 in wheat. In miR396 transgenic creeping bentgrass, AsVRN1 is induced in LD and remains elevated at LD 3-week (FIG. 15, panel a, c). Interestingly, levels of AsVRN1 are higher in TG plants versus WT controls under both SD and LD conditions (FIG. 15, panel a, c), implying that VRN1 is affected by miR396. During prolonged cold treatment, levels of AsVRN1 are gradually increased and remain elevated following cold in LD (FIG. 15, panel b, d), which is in agreement with previous study in cereals wheat, barley, and *Brachypodium*. AsVRN1 in TG plants has the similar expression profile as WT controls, though its levels are higher under SD and LD than that in WT plants, but not at the saturated cold (cold 17-week; FIG. 15, panel b, d).

In barley, levels of HvVRN2 (HvZCCT-Ha and HvZCCT-Hb) expression are higher when the plants are grown in LD versus SD. Similarly, levels of AsVRN2 expression in WT plants are dramatically upregulated during LD induction for two weeks and then are declined at LD 3-week (FIG. 15, panel a, c). In contrast, levels of AsVRN2 in transgenic plants are increased gradually when switching from SD to LD (FIG. 15, panel a, c). It should be noted that AsVRN2 is repressed in TG plants under both SD and LD conditions compared with WT controls (FIG. 15, panel a, c), which suggests that levels of AsVRN2 expression are affected by miR396. During vernalization, VRN2 transcript levels in wheat and barley leaves decreases significantly. Consistent with this, AsVRN2 in both WT and TG plants is gradually declined and then is elevated in LD conditions (FIG. 15, panel b, d).

In wheat and barley, VRN3 transcript levels are very low in SD and are induced when plants are grown in LD. In WT creeping bentgrass, VRN3 exhibits similar expression trend as in wheat and barley (FIG. 15, panel a, c). In comparison to WT controls, TG plants overexpressing miR396 is upregulated dramatically at LD 2-week and then is declined at LD 3-week (FIG. 15, panel a, c). The dramatic upregulation of the flowering promoter VRN3 suggests the vegetative to reproductive transition in TG plants at LD 2-week. Besides day length, vernalization also upregulates the transcript levels VRN3 in barley, wheat, and *Brachypodium*. In accordance with this, AsVRN3 mRNA levels are elevated during prolonged cold and the following LD conditions in both WT and TG plants, which indicates that AsVRN3 plays a role analogous to VRN3/FT in wheat, barley, and *Brachypodium*.

Impacts of miR396 on Histone Methylation

Different regulations of VRNs under SD-LD conditions between WT and TG plants indicate that miR396 plays a role in the vernalization pathway. Since VRN1 is an upstream regulator which represses the levels of VRN2 to promote the expression of VRN3 during and following vernalization, we speculate that VRIV1 is directly or indirectly regulated by miR396. The upregulation of HvVRN1 during vernalization is associated with an increase of active histone marks H3K4 trimethylation (H3K4me3) and a decrease of silent marks H3K27me3 at HvVRN1 chromatin, while levels of VRN2 and VRN3 in barley are not altered by histone modifications. In winter wheat, TaVRN1 is upregulated during vernalization through an increased level of H3K4me3 but no change in the level of H3K27me3. Therefore, it is hypothesized that AsVRN1 is also regulated by histone modifications during vernalization. In this study, higher levels of AsVRN1 has been observed in TG plants versus WT controls under SD and LD without vernalization, which prompts us to detect if the levels of active and silent histone marks are different in WT and TG plants. Transcript levels of methyltransferases are compared between WT and three transgenic lines through quantitative RT-PCR analysis (FIG. 16). AsATX2 and AsTrx1, which mediate methylation at H3K4, are down- and up-regulated in three transgenic lines, respectively. AsEZ1a, which encodes a SET-domain containing methyltransferase mediating methylation at H3K27, is repressed in TG plants. The results imply that miR396 might regulate genes' transcriptional activity by altering the methylation status.

Effects of Day Length and Vernalization on GRFs in WT and TG Plants

In addition to the key genes in the vernalization pathway, transcript levels of miR396 putative targets were also analyzed under SD-LD and SD-cold-LD conditions in both WT and TG plants. MiR396 is significantly induced and remain elevated when transferring plants from SD to LD (FIG. 13, panel a). In contrast, levels of its targets AsGRF3 and AsGRF4 are dramatically downregulated when switching to LD conditions in both WT and TG turfgrass (FIG. 17, panels a, c). Interestingly, expression profiles of AsGRF5 and AsGRF6 in WT plants don't show negative correlation with the levels of miR396 in SD-LD, suggesting that AsGRF5 and AsGRF6 are regulated by light-related factors besides their direct repressor miR396. In addition, levels of AsGRF5 plants are higher in transgenics versus WT plants under LD induction. It is possible that AsGRF5 is regulated by other factors which are impacted by miR396. When exposing WT and TG plants to SD-cold-LD conditions, levels of AsGRF3 and AsGRF4 show negative correlation with miR396 levels, whereas the negative correlation isn't observed in the expression profiles of AsGRF5 and AsGRF6 presumably due to the impacts of other factors during cold and LD conditions.

Genome-Wide Expression Analysis in miR396 TG Plants

To understand further how miR396 is involved in floral organ development and flowering time control, we performed RNA-seq analysis to study the differences of gene expression at genome level between WT controls and TG plants. Equal mixtures of RNA isolated from LD 3-week (without vernalization) leaf and shoot apical meristem (SAM) of WT and TG plants were used for cDNA library preparation. Illumina sequencing generated 4,444,691 contigs which were further assembled into 82,819 unigenes with an average size of 995.5 bp. The reliability of RNA-seq analysis was confirmed by multidimensional scaling (MDS) plot (FIG. 18, panel a), which shows the consistent between two biological replicates of WT and TG samples, respectively. A volcano plot shows the distribution of $Log_2$ fold changes (FC) of 17,338 unigenes at false discovery rate (FDR)<0.05 (FIG. 18, panels b, c). Among the differentially expressed transcripts ($Log_2$ FC>2 or <−2), 584 are upregulated and 1027 are downregulated in TG plants versus WT controls.

Gene Ontology Enrichment Analysis

To identify the major functional categories which are represented in transgenics versus WT controls, we performed gene ontology (GO) enrichment analysis. FIG. 19 shows that 21 GO terms were significantly enriched in upregulated and downregulated gene sets, respectively. Among others, the GO terms 'electron transport chain', 'carbohydrate metabolism', 'chloroplast thylakoid membrane', and 'ATP binding' are enriched in the upregulated genes. Under LD 3-week induction without vernalization, TG plants are in the flower development stage while WT plants are still in the vegetative growth. The enriched GO terms are related to energy generation and metabolism, which is fundamental for energy supply, carbon storage, and cell wall formation during flower development. The result is in close agreement with the study in other plant species during flower development. The enriched GO terms in the downregulated genes include 'cell division', 'DNA replication', 'regulation of transcription', 'nucleus', and 'DNA binding', which indicates that the processes of DNA replication and cell division are strongly repressed in TG plants overexpressing miR396. The result is in consistent with the miR396-GRF system, which shows the decreased cell number in miR396 transgenic leaves through repressing levels of GRFs.

Differential Expression of Transcription Factor Genes

MiRNAs are involved in various plant physiological processes through regulating their targets, the majority of which are transcription factors (TFs). In addition, TFs are key regulators implicated in flowering time control and flower development. Thus, we performed differential expression analysis of genes encoding for TFs. As heatmap shows in FIG. 20, 77 genes from 9 TF families are differentially expressed in TG versus WT plants, including NAC, MYB, MADS, GATA, E2F, bHLH, AP2, homeobox, and bZIP. Among them, MADS-box TF family, which consists of 10 upregulated and 8 downregulated members, is most represented. The second highest represented is GATA family (5 upregulated and 11 downregulated) followed by MYB TF genes (5 upregulated and 7 downregulated). MADS-box TFs play an essential role during plant flowering, which includes transition to flowering, petal and stamen specification, carpel and ovule development, pollen maturation and tube growth, sepal and petal longevity. Many GATA family members play a predominant role in floral development. For example, GNC and GNL from GATAs are flowering repressors through regulating the expression of florigen SOC1, while HAN serves as a floral morphology regulator through controlling the homeobox TF WUSCHEL. MYB TFs are critical for floral asymmetry. Other TF families, which exhibit significant differential expression, are also largely implicated in floral development.

Differential Expression of Flower Development and Chromatin Modification Genes

Besides identifying the major functional categories overrepresented in transgenics, we are also interested in the flower development and chromatin modification-related genes in TG versus WT data sets. Therefore, we determined the significantly enriched GO terms which related to flower development and chromatin modifications by GO enrichment analysis ($\log_2$ FC>1 or $\log_2$ FC<−1, FDR<0.05). The corresponding differentially expressed genes (DEGs) from each GO term were selected to generate a heatmap (FIG. 21). As shown in FIG. 21, 84 genes were categorized into the flower development group, which includes processes of SAM specification, vegetative to reproductive transition, flower organ formation, anther dehiscence, and starch biosynthesis and metabolism; 69 genes are categorized into the chromatin modification group, including the processes of histone acetylation and methylation. The results provide evidence at molecular level for the differences we observed in TG plants versus WT controls, such as altered flowering time, anther dehiscence defect, pollen sterility, and relatively high level of VRN1.

MiR396-GRF Module-Mediated Flower Development

Various studies shown that miR396 regulates plant leaf growth and floral organ development in both monocot and dicot species through targeting GRFs. High levels of miR396 or grf loss-of-function mutants always lead to the similar leaf phenotype, which is smaller leaf areas due to the smaller cell size or fewer cells. In contrast, overexpression of miR396 causes distinct floral organ defects in different plant species. For example, overexpression of OsmiR396d displays open husks and long sterile lemmas in rice through repressing OsGRF6, which targets OsJMJ706 and OsCR4; miR396-overexpressing *Arabidopsis* exhibits abnormal pistils via the regulation; transgenic tobacco overexpressing miR396 shows lack of SAM, altered anther and carpel morphology. In this study, the anthers of miR396c TG plants displayed abnormal stamen development, which includes barely sticking out of pelea, dehiscent defects and pollen sterility.

Generation of Transgenics Overexpressing miR396

A 510 bp DNA fragment of Os-miR396c gene (GenBank: AK062523.1) containing pre-miR396c stem-loop structure was amplified from rice cDNA. The forward and reverse primer set was 5'-TCTAGATTTTAACCCATCCAATGCCC-3' (SEQ ID NO:26) containing an XbaI recognition site and 5'-GTCGACCTCTCTCTCTCTCTGCCTG-3' (SEQ ID NO:27) containing a SalI recognition site. The cDNA were gel extracted and cloned into the pGEM-T Easy vector (Promega, Madison, Wis.). T Easy-cDNA with the correct sequence was digested and recombined into the binary vector pZH01 generating an overexpression gene construct, p35S-Os-miR396c/p35S-hyg. The construct contains a cauliflower mosaic virus 35S (CaMV 35S) promoter driving Os-miR396c followed by another CaMV 35S promoter driving a hyg gene for hygromycin resistance. The construct was transferred into *Agrobacterium tumefaciens* strain LBA4404. Creeping bentgrass cultivar 'Penn A-4' (supplied by HybriGene) was the host plant for *Agrobacterium*-mediated transformation. The embryonic callus transformation for creeping bentgrass was described previously.

Plant Growth

WT and the regenerated TG creeping bentgrass were clonally propagated from tillers and were grown in plastic pots (15×10.5 cm, Dillen Products) filled with commercial nutrient-rich soil (3-B Mix, Fafard). The plants were fertilized weekly with 0.2 g/L 20:10:20 water-soluble fertilizer (Peat-Lite Special; The Scotts Company) and were maintained in a growth room with SD light regime (14-h of light/10-h of dark). Temperatures in the SD growth room were 25° C. during the light period and 17° C. during the dark period with 350-400 μmol m$^{-2}$ s$^{-1}$ light intensity provided by AgroSun Gold 1000 W sodium/halide lamps (Maryland Hydroponics). The conditions for the LD growth room were the same as the SD growth room, except that the light regime is 16-h of light/8-h of dark. The vernalization treatment was performed in a cold room at 5° C. in an 8-h-ligh/16-h-dark photoperiod. Plants were grown under fluorescent bulbs and the light intensity was 100-150 μmol m$^{-2}$ s$^{-1}$ at plant level. WT and TG plants were propagated at the same time and from the same amount of tillers to make sure that they were at the same developmental stage before LD induction and vernalization treatment. We rotated plants every other day to minimize the difference of light intensities on plant growth within each growth room.

Microscopic Observations

Spikelets, floralets, anthers, and pollens of WT and TG plants were observed under stereo microscope (MEIJI EM-5). Photographs were taken using 35 mm SLR camera body (Canon) connected to the microscope. Scale bars were added to photographs using ImageJ. Spikelets and florets of vernalized WT and TG plants at 6$^{th}$ and 8$^{th}$ week after LD induction were detached for observation (FIG. 12, panels g-j). WT and TG anthers were detached and observed one-day before dehiscence (FIG. 12, panel k). To compare WT and TG pollen viability (FIG. 12, panels m, n), pollens were taken out of WT and TG anthers during the highest pollen viability rate of creeping bentgrass (9:00 AM) and stained with 2% (m/v) potassium iodide for microscopic observation.

Phylogenetic Analysis

The sequence alignments were performed by using the amino acid sequences of complete proteins AsVRN1, AsVRN2, and AsVRN3 found in this study and their orthologs in rice, *Arabidopsis*, wheat, barley, and *Brachypodium* based on previous study. Phylogenetic trees were generated from the aligned sequences by using the neighbor jointing method in the MEGA 6. The confidence values for the nodes were derived from 1,000 bootstrap replicates. The conserved domains of VRN1, VRN2, and VRN3 were aligned by using BioEdit sequence alignment editor.

Plant RNA Isolation and Expression Analysis

Plant total RNA was isolated from 100 mg of the 1$^{st}$ and 2$_{nd}$ topmost fully expanded leaves of each tiller. RNA isolation, semi-quantitative RT-PCR, real-time RT-PCR, and stem-loop RT-qPCR analyses were performed according to previous protocol. AsUBQ5 (JX570760) was used as an endogenous control. The miR396c stem-loop RT primer, PCR forward and reverse primers are 5'-GTCTCCTCTG-GTGCAGGGTCCGAGGTATTCGCAC CAGAGGAGA-CAAGTTC-3' (SEQ ID NO:28), 5'-GCGGTTCCACA- GCTTTCTT-3', and 5'-TGGTGCAGG GTCCGAGGTATT-3' (SEQ ID NO:29), respectively.

cDNA Library Preparation and Illumina Sequencing

Total RNA of LD 3-week leaves and SAMs from non-vernalized WT and TG plants were isolated and purified by using RNeasy Plant Mini Kit (Qiagen, Germantown, Md.). RNA quality was evaluated by the measurement of A260/A280 and A260/A230 ratios. Only RNA samples with A260/A280 ratio greater than 1.8 and A260/A230 ratio greater than 2.0 were used. For complete gene expression information, an equal mixture of RNA samples from leaves and SAMs was used for the construction of cDNA libraries using TruSeq RNA sample preparation v2 (Illumina Inc., San Diego, Calif.) according to the manufacturer's protocol. Single-end sequencing of each library was performed using Genome Analyzer IIx (Illumina Technologies) platform following the manufacturer's instructions. The raw reads coming from Illumina pipelines were first subjected to quality control checks by using FastQC, and then were trimmed using Trimmomatic. The trimmed reads from four cDNA libraries (two replicates for WT and TG) were used to generate a preliminary assembly by de novo assembly using In silico Read normalization followed by Trinity (version: trinityrnaseq_r2014-04-13) with default k-mer length of 25. Following a preliminary assembly, Trinity output contained 4,444,691 contigs. To verify de novo assembly quality, putative open reading frames were identified within transcripts by TransDecoder, which is integrated into Trinity, at minimum protein length of 50. Then the Trinity contigs of four libraries were clustered into a comprehensive transcriptome using CD-HIT-EST software with a sequence identity cut-off of 0.9 and comparison of both strands. A final reference unigene set containing 82,819 sequences were used for further data analysis.

Differential Expression Analysis

To estimate the expression levels, unigenes from each sample were aligned to build reference by using Bowtie2 and Tophat programs. A maximum of two mismatches were allowed for the alignments. The normalized gene expression level was calculated as $\log_2$-transformed count by Feature count software. The differential gene expression analysis was performed using EdgeR software with FDR corrected p-value cut-off of <0.05. An MDS plot was generated by using EdgeR to show the similarities between WT and TG samples and consistency between replicates. A volcano plot was created using the devtools package in R to plot $\log_2$ FC and the $-\log_{10}$ p-value of WT and TG data. The heatmaps showing expression profiles between WT and TG samples were generated based on the log 2-transformed count values using pHeatmap.2 package in R 3.2.0.

GO Enrichment Analysis

To gain information on the over-represented functional categories, GO enrichment analysis was performed. Since there is no GO annotation available for creeping bentgrass transcripts, putative GO terms were assigned using NCBI-blast and Blast2GO. GO enrichment of WT and TG data sets was performed using R-GOseq package with FDR corrected p-value cut-off of <0.05. The scatterplot of GO enrichment analysis in FIG. 19 was generated by RVIGO web server.

Example 3. Identification and Comparison of Putative MiR396c Target Sequences in Creeping Bentgrass Semi-quantitative RT-PCR analysis of AsGRF3, AsGRF4, AsGRF5, and AsGRF6 expression in WT and TG plants was performed and is depicted in FIG. 25, panel a, using AsUBQ5 as an endogenous control. A comparison was made of miR396c target sites in the putative targets AsGRF3, AsGRF4, AsGRF5, and AsGRF6 between rice and creeping bentgrass (FIG. 25, panel b). Asterisks indicate the identical RNA sequences.

Example 4. Overexpression of a Rice microRNA396 Gene Enhances Abiotic Tolerance in Transgenic Creeping Bentgrass FIG. 26 shows that miR396 expression increases under salt stress. FIGS. 27 and 28 show that overexpression of rice miR396 leads to enhanced salt tolerance in transgenic turfgrass plants. FIG. 29 shows a comparison of leaf RWC, leaf electrolyte leakage, total chlorophyll content, and proline content of two TG lines with wild-type creeping bentgrass. FIG. 30 shows the sodium and potassium content in wild-type and transgenic creeping bentgrass under normal conditions and under salt stress.

```
miR396c of Oryza (GenBank® Accession No. AK062523)
                                                              (SEQ ID NO: 1)
    1 cttttaacc catccaatgc cccttgttgc tgcaacctca tttagatctc atccttctct 61 tcatatatac atgcatactg ctataagtct actgtacgtc taccacagct tgcagccata 121 aagctcttcg tcctctctct ttctacggct gtggagctga agcatggcct agctgagcta 181 gcagctggtt cttggttata taaagagaga tagctaggat caagagagag gcagatggca 241 tggagaggtg ttgcaatgtg cattggatgt gtagatagag cctgcagatc tcgatcgatc 301 tcttcaagtc catgccatgc ctttccacag ctttcttgaa cttctcttgt gcctcactca 361 ctttcattac tggagagata tgcatcatca gtggaagctt atagggagag gagtgcaaga 421 agagggtcaa gaaagctgtg ggaagaaatg gcattacaag gactttgaat tcagttagca 481 atgccatgag acaggcagag agagagagag agagagagag agagagagag agagatgtga 541 tgctaatttt ccatttcatg taagttagct tttcataatt agatcaagtt ttctct
```

What is claimed is:

1. A transgenic plant having increased cold tolerance, flowering bypassing vernalization requirement and/or male sterility, comprising a recombinant nucleic acid molecule, said recombinant nucleic acid molecule comprising a nucleotide sequence encoding miR396c operatively associated with a heterologous promoter, wherein overexpression of the nucleotide sequence encoding miR396c confers increased cold tolerance, flowering bypassing vernalization requirement and/or male sterility as compared with a plant that does not comprise said recombinant nucleic acid molecule, wherein the nucleotide sequence encoding miR396c is the nucleotide sequence of SEQ ID NO:1 and wherein the transgenic plant is wheat, barley or turf grass.

2. The transgenic plant of claim 1, wherein the promoter is an actin promoter, a CaMV35S promoter, or a ubiquitin promoter.

3. A method of producing the transgenic plant of claim 1, having increased cold tolerance, flowering bypassing vernalization requirement and/or male sterility, comprising:
 a) transforming a plant cell with a recombinant nucleic acid molecule, said recombinant nucleic acid molecule comprising a nucleotide sequence encoding miR396c operatively associated with a heterologous promoter, wherein the nucleotide sequence encoding miR396c is the nucleotide sequence of SEQ ID NO:1, under conditions wherein the nucleotide sequence is overexpressed in the plant cell; and
 b) regenerating a transgenic plant from the transformed plant cell, thereby producing a transgenic plant having increased cold tolerance, flowering bypassing vernalization requirement and/or male sterility as compared with a plant that is not transformed with said recombinant nucleic acid molecule.

4. The method of claim 3, wherein the promoter is an actin promoter, a CaMV35S promoter or a ubiquitin promoter.

5. A transgenic plant having increased cold tolerance, flowering bypassing vernalization requirement and/or male sterility, produced by a method comprising the steps of:
 a) transforming a plant cell with a recombinant nucleic acid molecule, said recombinant nucleic acid molecule comprising a nucleotide sequence encoding miR396c operatively associated with a heterologous promoter, wherein the nucleotide sequence encoding miR396c is the nucleotide sequence of SEQ ID NO:1, under conditions wherein the nucleotide sequence is overexpressed in the plant cell; and
 b) regenerating a transgenic plant from the transformed plant cell, thereby producing a transgenic plant having increased cold tolerance, flowering bypassing vernalization requirement and/or male sterility as compared with a plant that is not transformed with said recombinant nucleic acid molecule, wherein the transgenic plant is wheat, barley or turf grass.

6. A crop comprising a plurality of transgenic plants of claim 1, planted together in an agricultural field, a golf course, a residential lawn, a road side, an athletic field, and/or a recreational field.

7. A transgenic plant having increased cold tolerance, flowering bypassing vernalization requirement and/or male sterility, produced by a method comprising the steps of:
 a) transforming a plant cell with a nucleic acid construct comprising, in the following order from 5' to 3':
  i) a first promoter;
  ii) a nucleotide sequence encoding miR396c, operably associated with the promoter of i), wherein the nucleotide sequence is heterologous to the promoter and wherein the nucleotide sequence encoding miR396c is the nucleotide sequence of SEQ ID NO:1;
  iii) a first termination sequence;
  iv) a second promoter;
  v) a nucleotide sequence encoding a selectable marker operably associated with the promoter of iv); and
  vi) a second termination sequence,
 under conditions wherein the nucleotide sequence is overexpressed in the plant cell; and
 b) regenerating the transgenic plant from the transformed plant cell, wherein the plant has increased cold tolerance, flowering bypassing vernalization requirement and/or male sterility, as compared with a plant that is not transformed with said nucleic acid construct and wherein the plant is wheat, barley or turf grass.

8. A crop comprising a plurality of plants according to claim 7, planted together in an agricultural field, a gold course, a residential lawn, a road side, an athletic field and/or a recreational field.

* * * * *

UNITED STATES PATENT AND TRADEMARK OFFICE
CERTIFICATE OF CORRECTION

PATENT NO. : 10,023,873 B2
APPLICATION NO. : 14/883350
DATED : July 17, 2018
INVENTOR(S) : Luo et al.

Page 1 of 1

It is certified that error appears in the above-identified patent and that said Letters Patent is hereby corrected as shown below:

On the Title Page

Item (56) References Cited, OTHER PUBLICATIONS, Page 2, Column 2, Maathius et al.: Please correct "$K^{+/Na+}$" to read -- $K^+/Na^+$ --

In the Specification

Column 6, Line 1: Please correct "$log_e$" to read -- $log_2$ --

Column 27, Line 25: Please correct "pri-miR396c" to read -- primary miR396c --

Column 31, Line 4: Please correct "12.54" to read -- 12.5μL --

Column 31, Line 5: Please correct "254" to read -- 25μL --

Column 34, Line 12: Please correct "VRN3IFT" to read -- VRN3/FT --

Column 34, Line 24: Please correct "VRN3IFT" to read -- VRN3/FT --

Column 38, Line 60: Please correct "$2_{nd}$" to read -- $2^{nd}$ --

Signed and Sealed this
Thirteenth Day of November, 2018

Andrei Iancu
*Director of the United States Patent and Trademark Office*

SEQUENCE LISTING

<160> NUMBER OF SEQ ID NOS: 29

<210> SEQ ID NO 1
<211> LENGTH: 596
<212> TYPE: DNA
<213> ORGANISM: Oryza sativa

<400> SEQUENCE: 1

```
cttttaacc catccaatgc cccttgttgc tgcaacctca tttagatctc atccttctct      60
tcatatatac atgcatactg ctataagtct actgtacgtc taccacagct tgcagccata    120
aagctcttcg tcctctctct ttctacggct gtggagctga agcatggcct agctgagcta    180
gcagctggtt cttggttata taaagagaga tagctaggat caagagagag gcagatggca    240
tggagaggtg ttgcaatgtg cattggatgt gtagatagag cctgcagatc tcgatcgatc    300
tcttcaagtc catgccatgc ctttccacag ctttcttgaa cttctcttgt gcctcactca    360
ctttcattac tggagagata tgcatcatca gtggaagctt ataggagag gagtgcaaga     420 agagggtcaa gaaagctgtg ggaagaaatg gcattacaag gactttgaat tcagttagca    480
atgccatgag acaggcagag agagagagag agagagagag agagagagag agagatgtga    540
tgctaatttt ccatttcatg taagttagct tttcataatt agatcaagtt ttctct        596
```

<210> SEQ ID NO 2
<211> LENGTH: 173
<212> TYPE: PRT
<213> ORGANISM: Agrostis stolonifera

<400> SEQUENCE: 2

```
Gly Arg Gly Lys Val Gln Tyr Lys Arg Ile Glu Asn Lys Ile Asn Arg
 1               5                  10                  15

Gln Val Thr Phe Ser Lys Arg Arg Asn Gly Leu Leu Lys Lys Ala His
            20                  25                  30

Glu Ile Ser Val Leu Cys Asp Ala Glu Val Ala Val Ile Val Phe Ser
        35                  40                  45

Pro Lys Gly Lys Leu Tyr Glu Tyr Ala Thr Asp Ser Ser Met Asp Lys
    50                  55                  60

Ile Leu Glu Arg Tyr Glu Arg Tyr Ser Tyr Ala Glu Lys Ala Leu Ile
65                  70                  75                  80

Ser Ala Glu Ser Glu Ser Glu Gly Asn Trp Cys His Glu Tyr Arg Lys
                85                  90                  95

Leu Lys Ala Lys Ile Glu Thr Ile Gln Lys Cys His Lys His Leu Met
            100                 105                 110

Gly Glu Asp Leu Asp Ser Leu Asn Leu Lys Glu Leu Gln Gln Leu Glu
        115                 120                 125

Gln Gln Leu Glu Ser Ser Leu Lys His Ile Arg Ser Arg Lys Ser His
    130                 135                 140

Leu Met Met Glu Ser Ile Ser Glu Leu Gln Lys Lys Glu Arg Ser Leu
145                 150                 155                 160

Gln Glu Glu Asn Lys Ala Leu Gln Lys Asp Leu Val Glu
                165                 170
```

<210> SEQ ID NO 3
<211> LENGTH: 173
<212> TYPE: PRT
<213> ORGANISM: Brachypodium distachyon

<400> SEQUENCE: 3

```
Gly Arg Gly Lys Val Gln Tyr Lys Arg Ile Glu Asn Lys Ile Asn Arg
1               5                   10                  15

Gln Val Thr Phe Ser Lys Arg Arg Ser Gly Leu Leu Lys Ala His
            20                  25                  30

Glu Ile Ser Val Leu Cys Asp Ala Glu Val Ala Val Ile Ile Phe Ser
            35                  40                  45

Thr Lys Gly Lys Leu Tyr Glu Phe Ala Thr Asp Ser Cys Met Asp Lys
        50                  55                  60

Ile Leu Glu Arg Tyr Glu Arg Tyr Ser Tyr Ala Glu Lys Val Leu Val
65                  70                  75                  80

Ser Thr Glu Ser Glu Ile Gln Gly Asn Trp Cys His Glu Tyr Arg Lys
                85                  90                  95

Leu Lys Ala Lys Val Glu Thr Ile Gln Lys Cys Gln Lys His Leu Met
                100                 105                 110

Gly Glu Asp Leu Glu Ser Leu Asn Leu Lys Glu Leu Gln Gln Leu Glu
                115                 120                 125

Gln Gln Leu Glu Ser Ser Leu Lys His Ile Arg Ser Arg Lys Asn Gln
        130                 135                 140

Leu Met His Glu Ser Ile Ser Glu Leu Gln Arg Lys Glu Arg Ser Leu
145                 150                 155                 160

Gln Glu Glu Asn Lys Ala Leu Gln Lys Glu Leu Val Glu
                165                 170
```

<210> SEQ ID NO 4
<211> LENGTH: 173
<212> TYPE: PRT
<213> ORGANISM: Triticum aestivum

<400> SEQUENCE: 4

```
Gly Arg Gly Lys Val Gln Tyr Lys Arg Ile Glu Asn Lys Ile Asn Arg
1               5                   10                  15

Gln Val Thr Phe Ser Lys Arg Arg Ser Gly Leu Leu Lys Ala His
            20                  25                  30

Glu Ile Ser Val Leu Cys Asp Ala Glu Val Gly Leu Ile Ile Phe Ser
            35                  40                  45

Thr Lys Gly Lys Leu Tyr Glu Phe Ser Thr Glu Ser Cys Met Asp Lys
        50                  55                  60

Ile Leu Glu Arg Tyr Glu Arg Tyr Ser Tyr Ala Glu Lys Val Leu Val
65                  70                  75                  80

Ser Ser Glu Ser Glu Ile Gln Gly Asn Trp Cys His Glu Tyr Arg Lys
                85                  90                  95

Leu Lys Ala Lys Val Glu Thr Ile Gln Lys Cys Gln Lys His Leu Met
                100                 105                 110

Gly Glu Asp Leu Glu Ser Leu Asn Leu Lys Glu Leu Gln Gln Leu Glu
                115                 120                 125

Gln Gln Leu Glu Ser Ser Leu Lys His Ile Arg Ser Arg Lys Asn Gln
        130                 135                 140

Leu Met His Glu Ser Ile Ser Glu Leu Gln Lys Lys Glu Arg Ser Leu
145                 150                 155                 160

Gln Glu Glu Asn Lys Val Leu Gln Lys Glu Leu Val Glu
                165                 170
```

<210> SEQ ID NO 5
<211> LENGTH: 173
<212> TYPE: PRT
<213> ORGANISM: Hordeum vulgare

<400> SEQUENCE: 5

```
Gly Arg Gly Lys Val Gln Tyr Lys Arg Ile Glu Asn Lys Ile Asn Arg
1               5                   10                  15

Gln Val Thr Phe Ser Lys Arg Arg Ser Gly Leu Leu Lys Lys Ala His
            20                  25                  30

Glu Ile Ser Val Leu Cys Asp Ala Glu Val Gly Leu Ile Ile Phe Ser
        35                  40                  45

Thr Lys Gly Lys Leu Tyr Glu Phe Ser Thr Glu Ser Cys Met Asp Lys
    50                  55                  60

Ile Leu Glu Arg Tyr Glu Arg Tyr Ser Tyr Ala Glu Lys Val Leu Val
65                  70                  75                  80

Ser Ser Glu Ser Glu Ile Gln Gly Asn Trp Cys His Glu Tyr Arg Lys
                85                  90                  95

Leu Lys Ala Lys Val Glu Thr Ile Gln Lys Cys Gln Lys His Leu Met
            100                 105                 110

Gly Glu Asp Leu Glu Ser Leu Asn Leu Lys Glu Leu Gln Gln Leu Glu
        115                 120                 125

Gln Gln Leu Glu Ser Ser Leu Lys His Ile Arg Ala Arg Lys Asn Gln
    130                 135                 140

Leu Met His Glu Ser Ile Ser Glu Leu Gln Lys Lys Glu Arg Ser Leu
145                 150                 155                 160

Gln Glu Glu Asn Lys Val Leu Gln Lys Glu Leu Val Glu
                165                 170
```

<210> SEQ ID NO 6
<211> LENGTH: 180
<212> TYPE: PRT
<213> ORGANISM: Oryza sativa

<400> SEQUENCE: 6

```
Gly Arg Gly Lys Val Gln Tyr Lys Arg Ile Glu Asn Lys Ile Asn Arg
1               5                   10                  15

Gln Val Thr Phe Ser Lys Arg Arg Ser Gly Leu Leu Lys Lys Ala Asn
            20                  25                  30

Glu Ile Ser Val Leu Cys Asp Ala Glu Val Ala Leu Ile Ile Phe Ser
        35                  40                  45

Thr Lys Gly Lys Leu Tyr Glu Tyr Ala Thr Asp Ser Cys Met Asp Lys
    50                  55                  60

Ile Leu Glu Arg Tyr Glu Arg Tyr Ser Tyr Ala Glu Lys Val Leu Ile
65                  70                  75                  80

Ser Ala Glu Ser Asp Thr Gln Gly Asn Trp Cys His Glu Tyr Arg Lys
                85                  90                  95

Leu Lys Ala Lys Val Glu Thr Ile Gln Lys Cys Gln Lys His Leu Met
            100                 105                 110

Gly Glu Asp Leu Glu Ser Leu Asn Leu Lys Glu Leu Gln Gln Leu Glu
        115                 120                 125

Gln Gln Leu Glu Asn Ser Leu Lys His Ile Arg Ser Arg Lys Ser Gln
    130                 135                 140

Leu Met Leu Glu Ser Ile Asn Glu Leu Gln Arg Lys Glu Lys Ser Leu
145                 150                 155                 160

Gln Glu Glu Asn Lys Val Leu Gln Lys Glu Asn Pro Cys Ser Phe Leu
                165                 170                 175

Gln Leu Val Glu
            180
```

<210> SEQ ID NO 7
<211> LENGTH: 173
<212> TYPE: PRT
<213> ORGANISM: Arabidopsis thaliana

<400> SEQUENCE: 7

Gly Thr Gly Arg Val Gln Tyr Lys Arg Ile Glu Asn Lys Ile Asn Arg
1               5                   10                  15

Gln Val Thr Phe Ser Lys Arg Arg Ala Gly Leu Leu Lys Lys Ala His
            20                  25                  30

Glu Ile Ser Val Leu Cys Asp Ala Glu Val Ala Leu Val Val Phe Ser
        35                  40                  45

His Lys Gly Lys Leu Phe Glu Tyr Ser Thr Asp Ser Cys Met Glu Lys
    50                  55                  60

Ile Leu Glu Arg Tyr Glu Arg Tyr Ser Tyr Ala Glu Arg Gln Leu Ile
65                  70                  75                  80

Ala Pro Glu Ser Asp Val Asn Thr Asn Trp Ser Met Glu Tyr Asn Arg
                85                  90                  95

Leu Lys Ala Lys Ile Glu Leu Leu Glu Arg Asn Gln Arg His Tyr Leu
            100                 105                 110

Gly Glu Asp Leu Gln Ala Met Ser Pro Lys Glu Leu Gln Asn Leu Glu
        115                 120                 125

Gln Gln Leu Asp Thr Ala Leu Lys His Ile Arg Thr Arg Lys Asn Gln
    130                 135                 140

Leu Met Tyr Glu Ser Ile Asn Glu Leu Gln Lys Lys Gly Lys Ala Ile
145                 150                 155                 160

Gln Glu Gln Asn Ser Met Leu Ser Lys Gln Ile Val Glu
                165                 170

<210> SEQ ID NO 8
<211> LENGTH: 42
<212> TYPE: PRT
<213> ORGANISM: Agrostis stolonifera

<400> SEQUENCE: 8

Arg Glu Ala Lys Val Met Arg Tyr Lys Glu Lys Arg Lys Arg Arg Cys
1               5                   10                  15

Tyr Glu Lys Gln Ile Arg Tyr Glu Ser Arg Lys Ala Tyr Ala Gln Met
            20                  25                  30

Arg Pro Arg Val Lys Gly Arg Phe Ala Lys
        35                  40

<210> SEQ ID NO 9
<211> LENGTH: 42
<212> TYPE: PRT
<213> ORGANISM: Brachypodium distachyon

<400> SEQUENCE: 9

Arg Glu Ala Lys Val Met Arg Tyr Arg Glu Lys Lys Lys Arg Arg Arg
1               5                   10                  15

Tyr Glu Lys Gln Ile Arg Tyr Glu Ser Arg Lys Ala Tyr Ala Glu Met
            20                  25                  30

Arg Pro Arg Val Lys Gly Arg Phe Ala Lys
        35                  40

<210> SEQ ID NO 10
<211> LENGTH: 42

```
<212> TYPE: PRT
<213> ORGANISM: Triticum monococcum

<400> SEQUENCE: 10

Arg Ala Ala Lys Val Met Arg Tyr Arg Glu Lys Arg Lys Arg Arg
1               5                   10                  15

Tyr Asp Lys Gln Ile Arg Tyr Glu Ser Arg Lys Ala Tyr Ala Glu Leu
            20                  25                  30

Arg Pro Arg Val Asn Gly Arg Phe Val Lys
        35                  40

<210> SEQ ID NO 11
<211> LENGTH: 42
<212> TYPE: PRT
<213> ORGANISM: Triticum monococcum

<400> SEQUENCE: 11

Arg Glu Ala Lys Val Met Arg Tyr Arg Glu Lys Arg Lys Arg Arg
1               5                   10                  15

Tyr Asp Lys Gln Ile Arg Tyr Glu Ser Arg Lys Ala Tyr Ala Glu Leu
            20                  25                  30

Arg Pro Arg Val Asn Gly Cys Phe Val Lys
        35                  40

<210> SEQ ID NO 12
<211> LENGTH: 42
<212> TYPE: PRT
<213> ORGANISM: Hordeum vulgare

<400> SEQUENCE: 12

Arg Glu Ala Lys Val Met Arg Tyr Arg Glu Lys Arg Lys Arg Arg
1               5                   10                  15

Tyr Asp Lys Gln Ile Arg Tyr Glu Ser Arg Lys Ala Tyr Ala Glu Leu
            20                  25                  30

Arg Pro Arg Val Asn Gly Arg Phe Ala Lys
        35                  40

<210> SEQ ID NO 13
<211> LENGTH: 42
<212> TYPE: PRT
<213> ORGANISM: Hordeum vulgare

<400> SEQUENCE: 13

Arg Glu Ala Lys Val Met Arg Tyr Arg Glu Lys Arg Lys Lys Arg
1               5                   10                  15

Tyr Asp Lys Gln Ile Arg Tyr Glu Ser Arg Lys Ala Tyr Ala Glu Leu
            20                  25                  30

Arg Pro Arg Val Asn Gly Arg Phe Val Lys
        35                  40

<210> SEQ ID NO 14
<211> LENGTH: 42
<212> TYPE: PRT
<213> ORGANISM: Oryza sativa

<400> SEQUENCE: 14

Arg Glu Ala Lys Leu Met Arg Tyr Lys Glu Lys Arg Lys Lys Arg Cys
1               5                   10                  15

Tyr Glu Lys Gln Ile Arg Tyr Ala Ser Arg Lys Ala Tyr Ala Glu Met
            20                  25                  30
```

Arg Pro Arg Val Arg Gly Arg Phe Ala Lys
        35                  40

<210> SEQ ID NO 15
<211> LENGTH: 138
<212> TYPE: PRT
<213> ORGANISM: Agrostis stolonifera

<400> SEQUENCE: 15

Thr Asn Leu Arg Val Thr Phe Gly Asn Arg Val Ser Asn Gly Cys
1               5                   10                  15

Glu Leu Lys Pro Ser Met Val Thr His Gln Pro Arg Val Glu Val Gly
            20                  25                  30

Gly Asn Glu Met Arg Thr Phe Tyr Thr Leu Val Met Val Asp Pro Asp
        35                  40                  45

Ala Pro Ser Pro Ser Asp Pro Asn Leu Arg Glu Tyr Leu His Trp Leu
    50                  55                  60

Val Thr Asp Ile Pro Gly Thr Thr Gly Ala Ser Phe Gly Gln Glu Val
65                  70                  75                  80

Met Cys Tyr Glu Ser Pro Arg Pro Asn Met Gly Ile His Arg Phe Val
                85                  90                  95

Leu Val Leu Phe Gln Gln Leu Gly Arg Gln Thr Val Tyr Ala Pro Gly
                100                 105                 110

Trp Arg Gln Asn Phe Asn Thr Arg Asp Phe Ala Glu Leu Tyr Asn Leu
            115                 120                 125

Gly Pro Pro Val Ala Ala Val Tyr Phe Asn
        130                 135

<210> SEQ ID NO 16
<211> LENGTH: 138
<212> TYPE: PRT
<213> ORGANISM: Brachypodium distachyon

<400> SEQUENCE: 16

Thr Asn Leu Arg Val Ser Phe Gly Asn Arg Asn Val Ser Asn Gly Cys
1               5                   10                  15

Glu Leu Lys Pro Ser Met Val Thr His Gln Pro Arg Val Glu Val Gly
            20                  25                  30

Gly Asn Glu Met Arg Thr Phe Tyr Thr Leu Val Met Val Asp Pro Asp
        35                  40                  45

Ala Pro Ser Pro Ser Asp Pro Asn Leu Arg Glu Tyr Leu His Trp Leu
    50                  55                  60

Val Thr Asp Ile Pro Gly Thr Thr Gly Ala Ser Phe Gly Gln Glu Val
65                  70                  75                  80

Met Cys Tyr Glu Ser Pro Arg Pro Ser Met Gly Ile His Arg Phe Val
                85                  90                  95

Leu Val Leu Phe Gln Gln Leu Gly Arg Gln Thr Val Tyr Ala Pro Gly
                100                 105                 110

Trp Arg Gln Asn Phe Asn Thr Arg Asp Phe Ala Glu Leu Tyr Asn Leu
            115                 120                 125

Gly Pro Pro Val Ala Ala Val Tyr Phe Asn
        130                 135

<210> SEQ ID NO 17
<211> LENGTH: 138
<212> TYPE: PRT
<213> ORGANISM: Triticum aestivum

<400> SEQUENCE: 17

Thr Asn Leu Arg Val Thr Phe Gly Asn Arg Thr Val Ser Asn Gly Cys
1               5                   10                  15

Glu Leu Lys Pro Ser Met Val Ala Gln Gln Pro Arg Val Glu Val Gly
            20                  25                  30

Gly Asn Glu Met Arg Thr Phe Tyr Thr Leu Val Met Val Asp Pro Asp
        35                  40                  45

Ala Pro Ser Pro Ser Asp Pro Asn Leu Arg Glu Tyr Leu His Trp Leu
    50                  55                  60

Val Thr Asp Ile Pro Gly Thr Thr Gly Ala Ser Phe Gly Gln Glu Val
65                  70                  75                  80

Met Cys Tyr Glu Ser Pro Arg Pro Thr Met Gly Ile His Arg Phe Val
                85                  90                  95

Leu Val Leu Phe Gln Gln Leu Gly Arg Gln Thr Val Tyr Ala Pro Gly
                100                 105                 110

Trp Arg Gln Asn Phe Asn Thr Arg Asp Phe Ala Glu Leu Tyr Asn Leu
                115                 120                 125

Gly Pro Pro Val Ala Ala Val Tyr Phe Asn
            130                 135

<210> SEQ ID NO 18
<211> LENGTH: 138
<212> TYPE: PRT
<213> ORGANISM: Hordeum vulgare

<400> SEQUENCE: 18

Thr Asn Leu Arg Val Thr Phe Gly Asn Arg Ala Val Ser Asn Gly Cys
1               5                   10                  15

Glu Leu Lys Pro Ser Met Val Ala Gln Gln Pro Arg Val Glu Val Gly
            20                  25                  30

Gly Asn Glu Met Arg Thr Phe Tyr Thr Leu Val Met Val Asp Pro Asp
        35                  40                  45

Ala Pro Ser Pro Ser Asp Pro Asn Leu Arg Glu Tyr Leu His Trp Leu
    50                  55                  60

Val Thr Asp Ile Pro Gly Thr Thr Gly Ala Ser Phe Gly Gln Glu Val
65                  70                  75                  80

Met Cys Tyr Glu Ser Pro Arg Pro Thr Met Gly Ile His Arg Phe Val
                85                  90                  95

Leu Val Leu Phe Gln Gln Leu Gly Arg Gln Thr Val Tyr Ala Pro Gly
                100                 105                 110

Trp Arg Gln Asn Phe Asn Thr Arg Asp Phe Ala Glu Leu Tyr Asn Leu
                115                 120                 125

Gly Gln Pro Val Ala Ala Val Tyr Phe Asn
            130                 135

<210> SEQ ID NO 19
<211> LENGTH: 138
<212> TYPE: PRT
<213> ORGANISM: Oryza sativa

<400> SEQUENCE: 19

Thr Asn Leu Lys Val Thr Tyr Gly Ser Lys Thr Val Ser Asn Gly Cys
1               5                   10                  15

Glu Leu Lys Pro Ser Met Val Thr His Gln Pro Arg Val Glu Val Gly
            20                  25                  30

Gly Asn Asp Met Arg Thr Phe Tyr Thr Leu Val Met Val Asp Pro Asp

```
            35                  40                  45
Ala Pro Ser Pro Ser Asp Pro Asn Leu Arg Glu Tyr Leu His Trp Leu
         50                  55                  60

Val Thr Asp Ile Pro Gly Thr Thr Ala Ala Ser Phe Gly Gln Glu Val
 65                  70                  75                  80

Met Cys Tyr Glu Ser Pro Arg Pro Thr Met Gly Ile His Arg Leu Val
                 85                  90                  95

Phe Val Leu Phe Gln Gln Leu Gly Arg Gln Thr Val Tyr Ala Pro Gly
            100                 105                 110

Trp Arg Gln Asn Phe Asn Thr Lys Asp Phe Ala Glu Leu Tyr Asn Leu
        115                 120                 125

Gly Ser Pro Val Ala Ala Val Tyr Phe Asn
    130                 135
```

```
<210> SEQ ID NO 20
<211> LENGTH: 138
<212> TYPE: PRT
<213> ORGANISM: Arabidopsis thaliana

<400> SEQUENCE: 20
```

```
Thr Thr Leu Lys Val Thr Tyr Gly Gln Arg Glu Val Thr Asn Gly Leu
 1               5                  10                  15

Asp Leu Arg Pro Ser Gln Val Gln Asn Lys Pro Arg Val Glu Ile Gly
            20                  25                  30

Gly Glu Asp Leu Arg Asn Phe Tyr Thr Leu Val Met Val Asp Pro Asp
        35                  40                  45

Val Pro Ser Pro Ser Asn Pro His Leu Arg Glu Tyr Leu His Trp Leu
 50                  55                  60

Val Thr Asp Ile Pro Ala Thr Thr Gly Thr Thr Phe Gly Asn Glu Ile
 65                  70                  75                  80

Val Cys Tyr Glu Asn Pro Ser Pro Thr Ala Gly Ile His Arg Val Val
                 85                  90                  95

Phe Ile Leu Phe Arg Gln Leu Gly Arg Gln Thr Val Tyr Ala Pro Gly
            100                 105                 110

Trp Arg Gln Asn Phe Asn Thr Arg Glu Phe Ala Glu Ile Tyr Asn Leu
        115                 120                 125

Gly Leu Pro Val Ala Ala Val Phe Tyr Asn
    130                 135
```

```
<210> SEQ ID NO 21
<211> LENGTH: 21
<212> TYPE: DNA
<213> ORGANISM: Oryza sativa

<400> SEQUENCE: 21
aagttcaaga aagctgtgga a                                            21

<210> SEQ ID NO 22
<211> LENGTH: 22
<212> TYPE: DNA
<213> ORGANISM: Oryza sativa

<400> SEQUENCE: 22
ccgttcaaga aagcctgtgg aa                                           22

<210> SEQ ID NO 23
<211> LENGTH: 22
<212> TYPE: DNA
```

```
<213> ORGANISM: Agrostis stolonifera

<400> SEQUENCE: 23
ccgttcaaga aagcctgtgg aa                                              22

<210> SEQ ID NO 24
<211> LENGTH: 22
<212> TYPE: DNA
<213> ORGANISM: Oryza sativa

<400> SEQUENCE: 24
ccgttcaaga aagcatgtgg aa                                              22

<210> SEQ ID NO 25
<211> LENGTH: 22
<212> TYPE: DNA
<213> ORGANISM: Agrostis stolonifera

<400> SEQUENCE: 25
tcgttcaaga aagcatgtgg aa                                              22

<210> SEQ ID NO 26
<211> LENGTH: 26
<212> TYPE: DNA
<213> ORGANISM: Artificial
<220> FEATURE:
<223> OTHER INFORMATION: PCR primer

<400> SEQUENCE: 26
tctagatttt aacccatcca atgccc                                          26

<210> SEQ ID NO 27
<211> LENGTH: 27
<212> TYPE: DNA
<213> ORGANISM: Artificial
<220> FEATURE:
<223> OTHER INFORMATION: PCR primer

<400> SEQUENCE: 27
gtcgacctct ctctctctct ctgcctg                                         27

<210> SEQ ID NO 28
<211> LENGTH: 50
<212> TYPE: DNA
<213> ORGANISM: Artificial
<220> FEATURE:
<223> OTHER INFORMATION: RT - PCR primer

<400> SEQUENCE: 28
gtctcctctg gtgcagggtc cgaggtattc gcaccagagg agacaagttc                50

<210> SEQ ID NO 29
<211> LENGTH: 21
<212> TYPE: DNA
<213> ORGANISM: Artificial
<220> FEATURE:
<223> OTHER INFORMATION: RT-PCR primer

<400> SEQUENCE: 29
tggtgcaggg tccgaggtat t                                               21
```